United States Patent
Shimoju et al.

(10) Patent No.: US 10,254,456 B2
(45) Date of Patent: Apr. 9, 2019

(54) POLARIZING PLATE COMPOSITION, POLARIZING PLATE PROTECTIVE FILM, POLARIZER, POLARIZING PLATE, AND LIQUID CRYSTAL DISPLAY DEVICE

(71) Applicant: FUJIFILM Corporation, Tokyo (JP)

(72) Inventors: Naoya Shimoju, Kanagawa (JP); Aiko Yoshida, Kanagawa (JP); Mayumi Nojiri, Kanagawa (JP); Yu Naito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 161 days.

(21) Appl. No.: 15/254,644

(22) Filed: Sep. 1, 2016

(65) Prior Publication Data

US 2016/0370523 A1     Dec. 22, 2016

Related U.S. Application Data

(63) Continuation of application No. PCT/JP2015/056235, filed on Mar. 3, 2015.

(30) Foreign Application Priority Data

Mar. 5, 2014  (JP) .................................. 2014-043364
Aug. 25, 2014  (JP) .................................. 2014-171034

(51) Int. Cl.
*G02B 5/30* (2006.01)
*C09J 201/00* (2006.01)
(Continued)

(52) U.S. Cl.
CPC .............. *G02B 5/3033* (2013.01); *B32B 7/12* (2013.01); *B32B 23/04* (2013.01); *C09J 201/00* (2013.01);
(Continued)

(58) Field of Classification Search
CPC ...... G02B 5/3033; G02B 5/3083; G02B 1/14; G02F 1/133528; G02F 1/133305;
(Continued)

(56) References Cited

U.S. PATENT DOCUMENTS

| 2011/0193260 | A1* | 8/2011 | Takeda | ..................... B29C 33/60 264/213 |
| 2014/0319436 | A1* | 10/2014 | Harada | ................ G02B 5/3083 252/582 |
| 2016/0341860 | A1* | 11/2016 | Nojiri | ................. G02B 5/3033 |

FOREIGN PATENT DOCUMENTS

CN       103135158 A       6/2013
JP       H08-199131        8/1996
(Continued)

OTHER PUBLICATIONS

International Search Report issued in PCT/JP2015/056235 dated May 26, 2015.
(Continued)

*Primary Examiner* — Ruiyun Zhang
(74) *Attorney, Agent, or Firm* — Edwards Neils, LLC; Jean C. Edwards, Esq.

(57) ABSTRACT

A polarizing plate composition, a polarizing plate protective film, a polarizer, a polarizing plate, and a liquid crystal display device contain a compound represented by the following Formula (I).

Formula (I)

(Continued)

In Formula (I), R represents a specific substituent, and each of $EWG^1$ and $EWG^2$ represents an electron-withdrawing group. $EWG^1$ and $EWG^2$ may form a ring by being bonded to each other. Here, there is no such case where $EWG^1$ and $EWG^2$ become the following group by being bonded to each other and form a ring by being bonded to a carbon atom substituted with R.

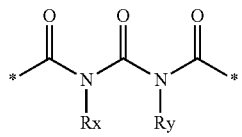

Each of Rx and Ry represents a hydrogen atom or a substituent. * represents a position of bonding to a carbon atom substituted with R.

18 Claims, 2 Drawing Sheets

(51) Int. Cl.
  *G02F 1/1335* (2006.01)
  *G02B 1/14* (2015.01)
  *B32B 7/12* (2006.01)
  *B32B 23/04* (2006.01)
(52) U.S. Cl.
  CPC ............... *G02B 1/14* (2015.01); *G02B 5/30* (2013.01); *G02F 1/133528* (2013.01); *B32B 2255/10* (2013.01); *B32B 2307/42* (2013.01); *B32B 2457/202* (2013.01); *Y10T 428/10* (2015.01); *Y10T 428/1036* (2015.01); *Y10T 428/1041* (2015.01)

(58) Field of Classification Search
  CPC ............... B32B 23/04; B32B 2307/42; B32B 2457/202; Y10T 428/1036; Y10T 428/1041; Y10T 428/10
  USPC ............... 428/1.1, 1.3, 1.31; 349/96, 117; 106/170.39, 170.48; 560/57.6, 57, 60; 568/331
  See application file for complete search history.

(56) References Cited

FOREIGN PATENT DOCUMENTS

| | | |
|---|---|---|
| JP | 2002-121459 A | 4/2002 |
| JP | 2004-315613 A | 11/2004 |
| JP | 2011-118135 A | 6/2011 |
| JP | 2013-109152 A | 6/2013 |
| JP | 2014-205801 A | 10/2014 |
| WO | 2006/115015 A1 | 11/2006 |
| WO | WO-2013073533 A1 * | 5/2013 ........... G02B 5/3083 |

OTHER PUBLICATIONS

Notification of First Office Action Issued by the State Intellectual Property Office dated Mar. 9, 2018, in connection with Chinese Patent Application No. 201580011948.X.

* cited by examiner

POLARIZING PLATE COMPOSITION, POLARIZING PLATE PROTECTIVE FILM, POLARIZER, POLARIZING PLATE, AND LIQUID CRYSTAL DISPLAY DEVICE

CROSS-REFERENCE TO RELATED APPLICATIONS

This application is a Continuation of PCT International Application No. PCT/JP2015/056235 filed on Mar. 3, 2015, which was published under PCT Article 21(2) in Japanese, and which claims priority under 35 U.S.C. § 119 (a) to Japanese Patent Application No. JP2014-043364 filed in Japan on Mar. 5, 2014 and Japanese Patent Application No. JP2014-171034 filed in Japan on Aug. 25, 2014. The above applications are hereby expressly incorporated by reference, in their entirety, into the present application.

BACKGROUND OF THE INVENTION

1. Field of the Invention

The present invention relates to a polarizing plate composition, a polarizing plate protective film, a polarizer, a polarizing plate, and a liquid crystal display device.

2. Description of the Related Art

A polarizing plate consisting of at least a polarizer and a polarizing plate protective film is used as an optical member in various liquid crystal display devices.

In addition to a chance of using the liquid crystal display devices indoors in TV and the like, a chance of using them outdoor mainly in a portable device and the like is increasing. Therefore, the development of liquid crystal display devices usable at a higher temperature and humidity than those of the related art is being required.

Furthermore, liquid crystal display devices are increasingly required to be usable for more diversified purposes and be able to withstand severe service conditions. Accordingly, every year, the liquid crystal display devices are increasingly required to have durability higher than that of the related art.

In recent years, as the liquid crystal display devices used mainly in TVs have become bigger and thinner, a polarizing plate including a polarizing plate protective film that is a constituent member has also been required to become thinner. From the viewpoint of workability, an appropriate hardness and excellent cutting properties have been emphasized for the polarizing plate protective film, and further improvement of those properties is required for the thin polarizing plate protective film.

Regarding a polarizing plate protective film using a cellulose acylate film, as a solution to various issues relating to the further improvement of the performance and the properties or manufacturing of the polarizing plate protective film, a method of causing the film to contain a specific compound is known.

For example, in order to inhibit an environmental humidity-dependent variation of retardation of the polarizing plate protective film, an organic acid compound having a pKa value of 2 to 7 is suggested (see JP2011-118135A).

Meanwhile, in order to improve a transverse variation of retardation, a method of using a deterioration preventive agent having hindered phenol and hindered amine in the same molecule is suggested (see JP2002-121459A). Furthermore, for color filters, a method of using a specific pigment dispersant is suggested (see WO2006/115015A).

SUMMARY OF THE INVENTION

Objects of the present invention are to provide a polarizing plate composition that can be generally used for each member in a polarizing plate, such as a polarizing plate protective film which makes a polarizer exhibit durability at a high temperature and high humidity, particularly maintains an effect of inhibiting a change of an orthogonal transmittance over a long period of time, and exhibits improved light-fast adhesiveness, an adhesive which maintains an effect of suppressing the deterioration of the durability of a polarizer at a high temperature and high humidity over a long period of time and is inhibited from undergoing bleed out occurring as a result of the deterioration of compatibility and the exposure to moist heat, and a polarizer, and to provide a polarizer, a polarizing plate, and a liquid crystal display device that are prepared using the polarizing plate composition.

As a result of conducting intensive investigation, the present inventors obtained knowledge that not only the method of causing the polarizing plate protective film to contain the compound as in the related art, but also the method of causing the adhesive layer or the polarizer layer to contain the compound is effective means for improving the durability of a polarizer. Based on the knowledge, the inventors accomplished the present invention.

That is, the objects described above are achieved by the following means.

<1> A polarizing plate composition comprising a compound represented by the following Formula (I).

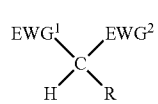

Formula (I)

In Formula (I), R represents a substituent, but the substituent is not a group containing a phenolic hydroxyl group or an aromatic amino group. Each of $EWG^1$ and $EWG^2$ independently represents an electron-withdrawing group. $EWG^1$ and $EWG^2$ may form a ring by being bonded to each other. Here, there is no such case where $EWG^1$ and $EWG^2$ become the following linking group by being bonded to each other and form a ring by being bonded to a carbon atom substituted with R.

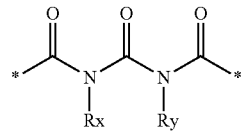

Herein, each of Rx and Ry independently represents a hydrogen atom or a substituent. * represents a position of bonding to a carbon atom substituted with R.

<2> The polarizing plate composition described in <1>, in which each of $EWG^1$ and $EWG^2$ is a substituent having a Hammett's σp value of equal to or greater than 0.20.

<3> The polarizing plate composition described in <1> or <2>, in which each of $EWG^1$ and $EWG^2$ is an acyl group, an alkoxycarbonyl group, an aryloxycarbonyl group, a thiocarbamoyl group in which at least one of hydrogen atoms is substituted with a group independently selected from an alkyl group or an aryl group, a sulfamoyl group in which at least one of hydrogen atoms is substituted with a group independently selected from an alkyl group or an aryl group, an alkylsulfonyl or arylsulfonyl group, an alkylsulfonyl or arylsulfinyl group, a cyano group, a nitro group, or a phosphono group.

<4> The polarizing plate composition described in any one of <1> to <3>, in which the compound represented by Formula (I) is represented by the following Formula (II).

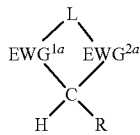

Formula (II)

In Formula (II), R has the same definition as R in Formula (I). Each of $EWG^{1a}$ and $EWG^{2a}$ independently represents a divalent electron-withdrawing group. L represents a single bond or a divalent linking group.

<5> The polarizing plate composition described in any one of <1> to <4>, in which an atom of L bonded to $EWG^{1a}$ and $EWG^{2a}$ is —C($R^{x1}$)($R^{x2}$)—, —N(Ra)—, —O—, or —S—, each of $R^{x1}$ and $R^{x2}$ is independently a hydrogen atom or a substituent, and Ra is a hydrogen atom or a substituent.

<6> The polarizing plate composition described in any one of <1> to <5>, in which the compound represented by Formula (I) is represented by the following Formula (III).

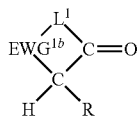

Formula (III)

In Formula (III), R has the same definition as R in Formula (I). $EWG^{1b}$ represents —C(=O)—, —$SO_2$—, —SO—, or *—P(=O)(ORb)O—. Herein, * represents a position of bonding to a carbon atom substituted with R, and Rb represents a substituent. $L^1$ represents a divalent linking group.

<7> The polarizing plate composition described in any one of <1> to <6>, in which R is an alkyl group, an alkenyl group, a cycloalkyl group, a cycloalkenyl group, an aryl group, or a heterocyclic group.

<8> The polarizing plate composition described in any one of <1> to <7>, in which the compound represented by Formula (I) is represented by the following Formula (IV).

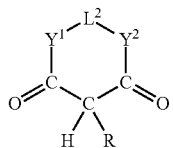

Formula (IV)

In Formula (IV), R has the same definition as R in Formula (I). Each of $Y^1$ and $Y^2$ independently represents —C($R^{x1}$)($R^{x2}$)—, —N(Ra)—, —O—, or —S—. Herein, each of $R^{x1}$ and $R^{x2}$ independently represents a hydrogen atom or a substituent, and Ra represents a hydrogen atom or a substituent. $L^2$ represents a single bond or a divalent linking group bonding $Y^1$ and $Y^2$ to each other through 1 to 3 atoms. $Y^1$ and $Y^2$, $Y^1$ and $L^2$, or $Y^2$ and $L^2$ may form a ring by being bonded to each other.

<9> The polarizing plate composition described in any one of <1> to <8>, further comprising cellulose acylate, polyvinyl alcohol, or acylated or ketalized polyvinyl alcohol.

<10> The polarizing plate composition described in <9>, in which provided that the total degree of acyl substitution of the cellulose acylate is denoted by A, A of the cellulose acylate satisfies the following expression.

$$1.5 \leq A \leq 3.0$$

<11> The polarizing plate composition described in <9> or <10>, in which provided that an acyl group of the cellulose acylate is an acetyl group, and the total degree of acetyl substitution of the cellulose acylate is denoted by B, B of the cellulose acylate satisfies the following expression.

$$2.0 \leq B \leq 3.0$$

<12> The polarizing plate composition described in any one of <1> to <11>, further comprising polyvinyl alcohol or acylated or ketalized polyvinyl alcohol and a metal compound colloid.

<13> The polarizing plate composition described in any one of <1> to <11>, further comprising polyvinyl alcohol or acylated or ketalized polyvinyl alcohol and a dichroic colorant.

<14> A polarizing plate protective film composed of the polarizing plate composition described in any one of <1> to <11>.

<15> A polarizer composed of the polarizing plate composition described in any one of <1> to <9> and <13>.

<16> A polarizing plate comprising an adhesive layer or a pressure sensitive adhesive layer composed of the polarizing plate composition described in any one of <1> to <9> and <12>.

<17> A polarizing plate comprising the polarizing plate protective film described in <14>.

<18> A polarizing plate comprising the polarizer described in <15>.

<19> A liquid crystal display device comprising the polarizing plate described in any one of <16> to <18>.

In the present specification, a range of numerical values represented using "to" means a range that includes numerical values listed before and after "to" as a lower limit and an upper limit respectively.

In the present specification, unless otherwise specified, a group (for example, a group having an alkyl moiety, an aryl moiety, or a heterocyclic moiety) which can have a substituent may have a substituent. For example, an alkyl group is an alkyl group which may have a substituent, and an aryl group or an aromatic group is an aryl group or an aromatic group which may have a substituent.

In a case where a single atom has at least two substituents, or each of neighboring atoms bonded to each other has a substituent, these substituents may form a ring by being bonded to each other.

Furthermore, in a case where there is a plurality of groups denoted by the same reference, or a plurality of groups repeats and in turn there is a plurality of groups denoted by the same reference, the groups may be the same as or different from each other.

In the present specification, when a plurality of substituents or linking groups (hereinafter, referred to as substituents and the like) is collectively or selectively specified, each of the substituents and the like may be the same as or different from each other.

According to the present invention, it is possible to provide a polarizing plate composition that can be generally used for each member in a polarizing plate, such as a polarizing plate protective film which makes a polarizer exhibit durability at a high temperature and high humidity, particularly maintains an effect of inhibiting a change of an orthogonal transmittance over a long period of time, and exhibits improved light-fast adhesiveness, an adhesive which maintains an effect of suppressing the deterioration of the durability of a polarizer at a high temperature and high humidity over a long period of time and is inhibited from undergoing bleed out occurring as a result of the deterioration of compatibility and the exposure to moist heat, and a polarizer, and to provide a polarizer, a polarizing plate, and a liquid crystal display device that are prepared using the polarizing plate composition.

The aforementioned characteristics, other characteristics, and advantages of the present invention will be further clarified by the following description with reference to the accompanying drawing as appropriate.

DESCRIPTION OF THE PREFERRED EMBODIMENTS

Figure 1:
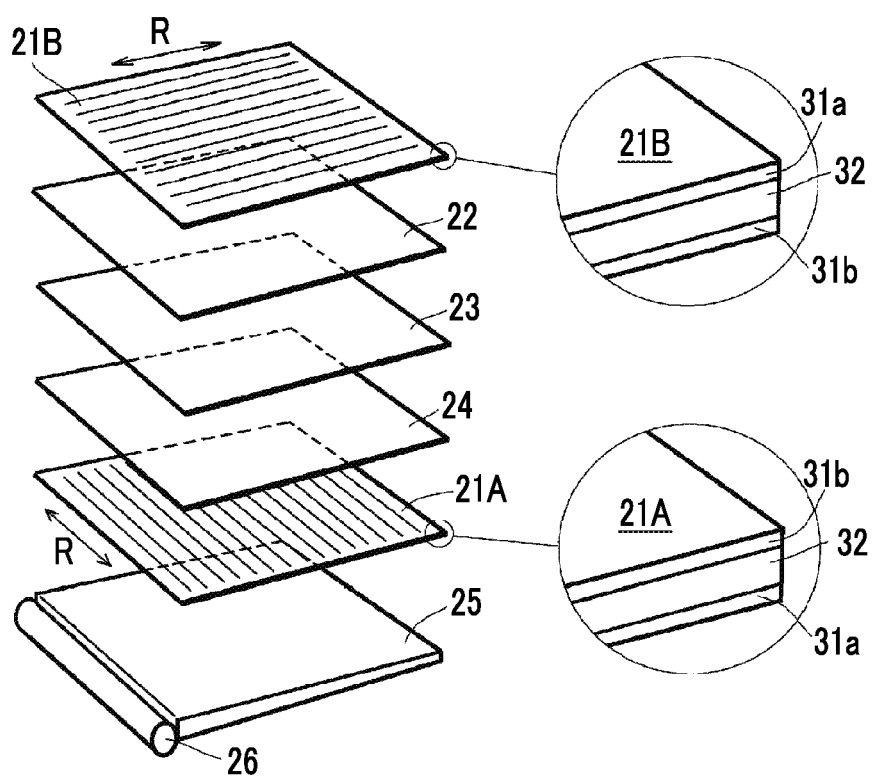
FIG. 1 is a view schematically showing an example of an internal structure of a liquid crystal display device of the present invention.

Hereinafter, the present invention will be specifically described based on embodiments.

The polarizing plate composition of the present invention may be used in any film or layer as long as the composition is used in or constitutes a polarizing plate.

Examples of the film or layer include a polarizing plate protective film, a polarizer, an adhesive layer, an antiglare layer, a clear hardcoat layer, an antireflection layer, an antistatic layer, an antifouling layer, and the like.

In the present invention, it is preferable to use the polarizing plate composition of the present invention in a polarizing plate protective film, a polarizer, and an adhesive layer.

Hereinafter, the polarizing plate composition will be described.

<<Polarizing Plate Composition>>
<Compound Represented by Formula (I)>
The polarizing plate composition of the present invention contains at least one or more kinds of compound represented by Formula (I).

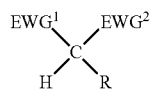

Formula (I)

In Formula (I), R represents a substituent, but the substituent is not a group containing a phenolic hydroxyl group or an aromatic amino group. Each of $EWG^1$ and $EWG^2$ independently represents an electron-withdrawing group. $EWG^1$ and $EWG^2$ may form a ring by being bonded to each other. Here, there is no such case where $EWG^1$ and $EWG^2$ become the following linking group by being bonded to each other and form a ring by being bonded to a carbon atom substituted with R.

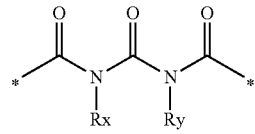

Herein, each of Rx and Ry independently represents a hydrogen atom or a substituent. * represents a position of bonding to a carbon atom substituted with R.

The electron-withdrawing group represented by $EWG^1$ and $EWG^2$ is preferably a group having a Hammett's σp value of equal to or greater than 0. Examples of the substituent having a positive σp value include a halogen atom such as fluorine (0.06), chlorine (0.30), bromine (0.27), or iodine (0.30), a group having a carbonyl group such as —CHO (0.22), —COCH$_3$ (0.50), —COC$_6$H$_5$ (0.46), —CONH$_2$ (0.36), —COO$^-$ (0.30), —COOH (0.41), —COOCH$_3$ (0.39), or —COOC$_2$H$_5$ (0.45), a group having sulfonyl or sulfinyl such as —SOCH$_3$ (0.49), —SO$_2$CH$_3$ (0.72), —SO$_2$C$_6$H$_5$ (0.68), —SO$_2$CF$_3$ (0.93), —SO$_2$NH$_2$ (0.57), —SO$_2$OC$_6$H$_5$ (0.23), —SO$_3^-$ (0.09), or —SO$_3$H (0.50), a nitrogen-containing substituent such as —CN (0.66), —NO$_2$ (0.78), —N(CH$_3$)$_3^+$ (0.82), or —N(CF$_3$)$_2$ (0.53), and a halogen atom-substituted alkyl group such as —CCl$_3$ (0.46), —CH$_2$Cl (0.18), —CHCl$_2$ (0.32), or —CF$_3$ (0.54). Herein, the numerical value in the bracket is a σp value.

The Hammett's σp value is also described in, for example, C. Harsch et al., J. Med. Chem., 16, 1207 (1973), C. Harsch et al., J. Med. Chem., 20, 304 (1977), Chem. Rev. 91, 165 (1991), and the like.

In the present invention, the Hammett's σp value is preferably equal to or greater than 0.20.

Specifically, preferred examples of the group having a Hammett's σp value of equal to or greater than 0.20 include an acyl group, an alkoxycarbonyl group, an aryloxycarbonyl group, a carbamoyl group (for example, —CONHCH$_3$ (0.32)) in which at least one of hydrogen atoms is alkyl or aryl, a thioacyl group, an alkoxythiocarbonyl group, an aryloxythiocarbonyl group, a thiocarbamoyl group (for example, —CSNHCH$_3$ (0.34)) in which at least one of hydrogen atoms is alkyl or aryl, a sulfamoyl group (for example, —SO$_2$N(CH$_3$)$_2$ (0.65)) in which at least one of hydrogen atoms is alkyl or aryl, an alkylsulfonyl or arylsulfonyl group (for example, —SO$_2$CH$_3$ (0.72) and —SO$_2$C$_6$H$_5$ (0.68)), an alkylsulfinyl or arylsulfinyl group (for example, —SOCH$_3$ (0.49)), a cyano group, a nitro group, and a phosphono group. Among these, an acyl group, an alkoxycarbonyl group, an aryloxycarbonyl group, an alkylcarbamoyl or arylcarbamoyl group, an alkylsulfamoyl or arylsulfamoyl group, an alkylsulfonyl or arylsulfonyl group, an alkylsulfinyl or arylsulfinyl group, a cyano group, a nitro group, and a phosphono group are more preferable.

The acyl group may be an aromatic or aliphatic acyl group and includes a formyl group. The number of carbon atoms of the acyl group is preferably 1 to 20 and more preferably 2 to 10.

Examples of the acyl group include formyl, acetyl, propionyl, isobutyryl, pivaloyl, lauroyl, myristoyl, acryloyl, methacryloyl, benzoyl, and naphthoyl.

Among the acyl groups, an acyl group (for example, pivaloyl) of branched alkyl (preferably a tert-alkylcarbonyl group) or a phenylcarbonyl group having a substituent in an ortho-position is preferable.

The number of carbon atoms of the alkoxycarbonyl group is preferably 2 to 20 and more preferably 2 to 10. The alkoxycarbonyl group is preferably a branched alkoxycarbonyl group, and more preferably a tert-alkyloxycarbonyl group. Examples of the alkoxycarbonyl group include methoxycarbonyl, ethoxycarbonyl, isopropoxycarbonyl, tert-butyloxycarbonyl, n-octyloxycarbonyl, and dodecyloxycarbonyl.

The number of carbon atoms of the aryloxycarbonyl group is preferably 7 to 20 and more preferably 7 to 16. Examples of the aryloxycarbonyl group include phenyloxycarbonyl and naphthyloxycarbonyl.

Herein, the alkoxycarbonyl group is more preferable than the aryloxycarbonyl group.

The number of carbon atoms of the carbamoyl group, in which at least one of hydrogen atoms is substituted with a group independently selected from an alkyl group or an aryl group, is preferably 1 to 20 and more preferably 1 to 10.

Examples of the carbamoyl group include carbamoyl, N-methylcarbamoyl, N,N-dimethylcarbamoyl, N-phenylcarbamoyl, N,N-diphenylcarbamoyl, and N-methyl-N-phenylcarbamoyl.

The number of carbon atoms of the alkyl or arylsulfonyl group is preferably 1 to 20 and more preferably 1 to 10.

Examples of the alkylsulfonyl group include methylsulfonyl, isopropylsulfonyl, tert-butylsulfonyl, and tert-octylsulfonyl, and examples of the arylsulfonyl group include phenylsulfonyl.

The number of carbon atoms of the alkyl or arylsulfinyl group is preferably 1 to 20 and more preferably 1 to 10.

Examples of the alkylsulfinyl group include methylsulfinyl, isopropylsulfinyl, tert-butylsulfinyl, and tert-octylsulfinyl, and examples of the arylsulfinyl group include phenylsulfinyl.

The phosphono group is represented by $-P(=O)(ORb)_2$. Rb represents a substituent, and substituents preferred as Rb will be described later.

Preferred ranges and specific examples of the thioacyl group, the alkoxythiocarbonyl group, the aryloxythiocarbonyl group, and the thiocarbamoyl group, in which at least one of hydrogen atoms is substituted with a group independently selected from an alkyl group or an aryl group, include those obtained by substituting only the C(=O) portion of the corresponding acyl group, alkoxycarbonyl group, aryloxycarbonyl group, and thiocarbamoyl group, in which at least one of hydrogen atoms is substituted with a group independently selected from an alkyl group or an aryl group, with (C=S).

In a case where $EWG^1$ and $EWG^2$ form a ring by being bonded to each other, as the portion bonded to a carbon atom to which R is bonded, —C(=O)—, —C(=S)—, —SO$_2$—, —SO—, or *—P(=O)(ORb)O— is preferable. Herein, * represents a position of bonding to a carbon atom to which R is bonded, and Rb represents a substituent. In this case, —C(=O)—, —C(=S)—, or —SO$_2$— is more preferable, —C(=O)— or —C(=S)— is even more preferable, and —C(=O)— is particularly preferable.

Examples of the substituent represented by R, Rx, and Ry include the following substituent S.

Here, R is neither a substituent containing a phenolic hydroxyl group or an aromatic amino group nor a group containing —NH$_2$.

[Substituent S]

Examples of the substituent S include an alkyl group (preferably having 1 to 20 carbon atoms, for example, methyl, ethyl, isopropyl, tert-butyl, pentyl, heptyl, 1-ethylpentyl, 2-ethylhexyl, benzyl, 2-ethoxyethyl, or 1-carboxymethyl), an alkenyl group (preferably having 2 to 20 carbon atoms, for example, vinyl, allyl, or oleyl), an alkynyl group (preferably having 2 to 20 carbon atoms, for example, ethynyl, 2-propynyl, 2-butynyl, or phenylethynyl), a cycloalkyl group (preferably having 3 to 20 carbon atoms, for example, cyclopropyl, cyclopentyl, cyclohexyl, or 4-methylcyclohexyl), an aryl group (preferably having 6 to 20 carbon atoms, for example, phenyl, 1-naphthyl, 4-methoxyphenyl, 2-chlorophenyl, or 3-methylphenyl), a heterocyclic group (preferably a heterocyclic group having 0 to 20 carbon atoms, in which a heteroatom constituting a ring is preferably an oxygen atom, a nitrogen atom, or a sulfur atom, the heterocyclic group may be fused with a benzene ring or a heterocyclic ring in the form of a 5-membered or 6-membered ring, and the ring may be a saturated ring, an unsaturated ring, or an aromatic ring, for example, 2-pyridyl, 4-pyridyl, 2-imidazolyl, 2-benzimidazolyl, 2-thiazolyl, or 2-oxazolyl), an alkoxy group (preferably having 1 to 20 carbon atoms, for example, methoxy, ethoxy, isopropyloxy, or benzyloxy), an aryloxy group (preferably having 6 to 20 carbon atoms, for example, phenoxy, 1-naphthyloxy, 3-methylphenoxy, or 4-methoxyphenoxy), an alkylthio group (preferably having 1 to 20 carbon atoms, for example, methylthio, ethylthio, isopropylthio, or benzylthio), an arylthio group (preferably having 6 to 20 carbon atoms, for example, phenylthio, 1-naphthylthio, 3-methylphenylthio, or 4-methoxyphenylthio), an acyl group (including an alkylcarbonyl group, an alkenylcarbonyl group, an arylcarbonyl group, and a heterocyclic carbonyl group and preferably having 20 or less carbon atoms, for example, acetyl, pivaloyl, acryloyl, methacryloyl, benzoyl, or nicotinoyl), an alkoxycarbonyl group (preferably having 2 to 20 carbon atoms, for example, ethoxycarbonyl or 2-ethylhexyloxycarbonyl), an aryloxycarbonyl group (preferably having 7 to 20 carbon atoms, for example, phenyloxycarbonyl or naphthyloxycarbonyl), an amino group (including an amino group, an alkylamino group, an arylamino group, and a heterocyclic amino group and preferably having 0 to 20 carbon atoms, for example, amino, N,N-dimethylamino, N,N-diethylamino. N-ethylamino, anilino, 1-pyrrolidinyl, piperidino, or morpholinyl), an alkylsulfonamide or arylsulfonamide group (preferably having 0 to 20 carbon atoms, for example, N,N-dimethylsulfonamide or N-phenylsulfonamide), an alkylsulfamoyl or arylsulfamoyl group (preferably having 0 to 20 carbon atoms, for example, N,N-dimethylsulfamoyl or N-phenylsulfamoyl), an acyloxy group (preferably having 1 to 20 carbon atoms, for example, acetyloxy or benzoyloxy), an alkylcarbamoyl or arylcarbamoyl group (preferably having 1 to 20 carbon atoms, for example, N,N-dimethylcarbamoyl or N-phenylcarbamoyl), an acylamino group (preferably having 1 to 20 carbon atoms, for example, acetylamino, acryloylamino, benzoylamino, or nicotinamide), a cyano group, a hydroxy group, a mercapto group, a sulfo group or a salt thereof, a carboxy group or a salt thereof, a phosphoric acid group or a salt thereof, an onio group (for example, a sulfonio group of a sulfonium salt, an ammonio group of an ammonium salt, an iodonio group of an iodonium salt, or a phosphonio group of a phosphonium salt), a thioacyl group, an alkoxythiocarbonyl group, an aryloxythiocarbonyl group, an alkylthiocarbamoyl or arylthiocarbamoyl group (preferred ranges and specific examples of these include those obtained by substituting only the C(=O) portion of the corresponding acyl group, alkoxycarbonyl group, aryloxycarbonyl group, and alkyl or arylcarbamoyl group with (C=S)), and a halogen atom (for example, a fluorine atom, a chlorine atom, a bromine atom, or an iodine atom).

The above substituents may be further substituted with a substituent, and examples of the substituent include the substituent S described above.

Examples thereof include an aralkyl group obtained by the substitution of an aryl group with an alkyl group, a group obtained by the substitution of an alkoxycarbonyl group or a cyano group with an alkyl group, and the like.

R is preferably an alkyl group, an alkenyl group, a cycloalkyl group, a cycloalkenyl group, an aryl group, a nitro group, a heterocyclic group, or a halogen atom, more preferably an alkyl group, an alkenyl group, a cycloalkyl group, a cycloalkenyl group, an aryl group, a nitro group, or a halogen atom, and even more preferably an alkyl group, an alkenyl group, a cycloalkyl group, a cycloalkenyl group, or an aryl group.

The number of carbon atoms of the alkyl group represented by R is preferably 1 to 20, more preferably 1 to 10, and even more preferably 1 to 5.

Examples of the alkyl group include methyl, ethyl, isopropyl, n-butyl, tert-butyl, 2-ethylhexyl, n-octyl, n-decyl, n-octadecyl, and isooctadecyl.

The number of carbon atoms of the alkenyl group represented by R is preferably 2 to 20, more preferably 2 to 10, and even more preferably 2 to 5.

Examples of the alkenyl group include vinyl, allyl, isopropenyl, 2-pentenyl, and oleyl.

The number of carbon atoms of the cycloalkyl group represented by R is preferably 3 to 20, more preferably 5 to 10, and even more preferably 5 or 6.

Examples of the cycloalkyl group include cyclopropyl, cyclopentyl, and cyclohexyl.

The number of carbon atoms of the cycloalkenyl group represented by R is preferably 5 to 20, more preferably 5 to 10, and even more preferably 5 or 6.

Examples of the cycloalkenyl group include cyclopentenyl and cyclohexenyl.

The number of carbon atoms of the aryl group represented by R is preferably 6 to 20, more preferably 6 to 10, and even more preferably 6 to 8.

Examples of the aryl group include phenyl and naphthyl.

The number of carbon atoms of the heterocyclic group represented by R is preferably 0 to 20, more preferably 1 to 10, even more preferably 2 to 10, and particularly preferably 2 to 5.

As the heterocyclic ring in the heterocyclic group, a 5-membered or 6-membered heterocyclic ring is preferable. The heterocyclic ring may be substituted with a substituent and may be fused with a benzene ring, or a heterocyclic ring. Herein, examples of the substituent include the substituent S described above.

Examples of the heteroatom constituting the heterocyclic ring in the heterocyclic group include a nitrogen atom, an oxygen atom, and a sulfur atom. The heterocyclic ring may be a heterocyclic aromatic ring or a heterocyclic ring which is not an aromatic ring.

Examples of the heterocyclic ring of the heterocyclic group include a thiophene ring, a furan ring, a pyrrole ring, a pyrazole ring, an imidazole ring, a thiazole ring, an oxazole ring, a triazole ring, a tetrazole ring, a pyridine ring, a pyrazine ring, a pyrrolidine ring, a pyrroline ring, a pyrazolidine ring, piperidine ring, a piperazine ring, a morpholine ring, a thiomorpholine ring, and rings formed by the fusion of these rings with a benzene ring (for example, an indole ring and a benzimidazole ring).

Examples of the halogen atom represented by R include a fluorine atom, a chlorine atom, and a bromine atom.

Any one of $EWG^1$, $EWG^2$, and R in Formula (I) is preferably a group having at least one cyclic structure.

The compound represented by Formula (I) is preferably a compound represented by the following Formula (II).

Formula (II)

In Formula (II), R has the same definition as R in Formula (I), and the preferred range thereof is also the same. Each of $EWG^{1a}$ and $EWG^{2a}$ independently represents a divalent electron-withdrawing group. L represents a single bond or a divalent linking group. Each of these groups may be further substituted with a substituent.

The divalent electron-withdrawing group represented by $EWG^{1a}$ and $EWG^{2a}$ is preferably —C(=O)—, —SO$_2$—, —SO—, or *—P(=O)(ORb)O—. Herein, * represents a position of bonding to a carbon atom to which R is bonded. Rb represents a substituent.

In the divalent linking group represented by L, the atom of L bonded to $EWG^{1a}$ and $EWG^{2a}$ is preferably —C($R^{x1}$)($R^{x2}$)—, —N(Ra)—, —O—, or —S—. Herein, each of $R^{x1}$ and $R^{x2}$ independently represents a hydrogen atom or a substituent, and Ra represents a hydrogen atom or a substituent.

Examples of the substituent represented by Ra, Rb, $R^{x1}$, and $R^{x2}$ include the substituent S described above.

The substituent represented by Ra is preferably an alkyl group, an alkenyl group, a cycloalkyl group, a cycloalkenyl group, an aryl group, or a heterocyclic group, more preferably an alkyl group, a cycloalkyl group, or an aryl group, and even more preferably an alkyl group.

Ra is preferably a hydrogen atom, an alkyl group, a cycloalkyl group, or an aryl group, and more preferably a hydrogen atom or an alkyl group.

Rb is preferably an alkyl group, an alkenyl group, a cycloalkyl group, a cycloalkenyl group, an aryl group, or a heterocyclic group, more preferably an alkyl group, a cycloalkyl group, or an aryl group, even more preferably an alkyl group or an aryl group, and particularly preferably an aryl group.

The substituent represented by $R^{x1}$ and $R^{x2}$ is preferably an alkyl group, an alkenyl group, a cycloalkyl group, a cycloalkenyl group, or an aryl group.

Each of $R^{x1}$ and $R^{x2}$ is preferably a hydrogen atom, an alkyl group, an alkenyl group, a cycloalkyl group, a cycloalkenyl group, or an aryl group.

The ring formed by $EWG^{1a}$, $EWG^{2a}$, and L is preferably a 5- to 8-membered ring, more preferably 5- to 7-membered ring, and even more preferably 5- or 6-membered ring.

The compound represented by Formula (II) is more preferably a compound represented by the following Formula (III).

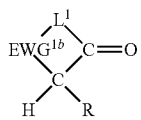

Formula (III)

In Formula (III), R has the same definition as R in Formula (I), and the preferred range thereof is also the same. $EWG^{1b}$ represents —C(=O)—, —SO$_2$—, —SO—, or *—P(=O)(ORb)O—. Herein, * represents a position of bonding to a carbon atom substituted with R, and Rb represents a substituent. $L^1$ represents a divalent linking group. Each of these groups may be further substituted with a substituent.

$EWG^{1b}$ is preferably —C(=O)—, —SO$_2$—, or —SO—, more preferably —C(=O)— or —SO$_2$—, and even more preferably —C(=O)—.

In the divalent linking group represented by $L^1$, the atom of $L^1$ bonded to $EWG^{1b}$ and —C(=O)— is preferably —C($R^{x1}$)($R^{x2}$)—, —N(Ra)—, —O—, or —S—. Herein, each of $R^{x1}$ and $R^{x2}$ independently represents a hydrogen atom or a substituent, and Ra represents a hydrogen atom or a substituent.

$L^1$ has the same definition as the divalent linking group represented by L in Formula (II), and the preferred range thereof is also the same.

As the divalent linking group represented by L and $L^1$, —O—, —S—, —N(Ra)—, —C(=O)—, —C(=S)—, —SO$_2$—, —SO—, an alkylene group, an alkenylene group, a cycloalkylene group, a cycloalkenylene group, an arylene group, or a divalent heterocyclic group is preferable. The number of carbon atoms of the alkylene group is preferably 1 to 3, and examples of the alkylene group include methylene, ethylene, and propylene. The number of carbon atoms of the alkenylene group is preferably 2 or 3, and examples of the alkenylene group include ethenylene. The number of carbon atoms of the cycloalkylene group is preferably 5 to 12, and examples of the cycloalkylene group include cyclopentylene and cyclohexylene. The number of carbon atoms of the cycloalkenylene group is preferably 5 to 12, and examples of the cycloalkenylene group include cyclopentenylene and cyclohexenylene. The number of carbon atoms of the arylene group is preferably 6 to 12, and examples of the arylene group include phenylene and naphthylene. The heteroatom constituting the heterocyclic ring in the divalent heterocyclic group is preferably an oxygen atom, a sulfur atom, or a nitrogen atom. The number of carbon atoms of the divalent heterocyclic group is preferably 1 to 12, more preferably 2 to 12, and even more preferably 3 to 12. Examples of the heterocyclic ring include a furan ring, a thiophene ring, a pyrrole ring, a pyrazole ring, an imidazole ring, an oxazole ring, a thiazole ring, a pyridine ring, a pyrrolidine ring, a piperazine ring, and a morpholine ring.

In a case where the divalent linking group is a cycloalkylene group, a cycloalkenylene group, an arylene group, or a divalent heterocyclic group, two direct bonds preferably have two adjacent atoms, that is, atoms in ortho-positions.

—N(Ra)— has the same definition as —N(Ra)— described above, and the preferred range thereof is also the same.

L is preferably a single bond, —O—, —S—, —N(Ra)—, —C(=O)—, —C(=S)—, —SO$_2$—, —SO—, an alkylene group, an alkenylene group, a cycloalkylene group, a cycloalkenylene group, or an arylene group.

$L^1$ is preferably —O—, —S—, —N(Ra)—, —C(=O)—, —C(=S)—, —SO$_2$—, —SO—, an alkylene group, an alkenylene group, a cycloalkylene group, a cycloalkenylene group, or an arylene group.

The ring formed by $EWG^{1b}$, $L^1$, and a carbon atom substituted with R is preferably a 5- to 8-membered ring, more preferably a 5- to 7-membered ring, and even more preferably a 5- or 6-membered ring.

The compound represented by Formula (I) is particularly preferably a compound represented by the following Formula (IV).

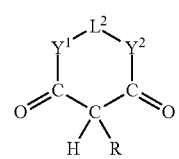

Formula (IV)

In Formula (IV), R has the same definition as R in Formula (I), and the preferred range thereof is also the same. Each of $Y^1$ and $Y^2$ independently represents —C($R^{x1}$)($R^{x2}$)—, —N(Ra)—, —O—, or —S—. Herein, each of $R^{x1}$ and $R^{x2}$ independently represents a hydrogen atom or a substituent, and Ra represents a hydrogen atom or a substituent. $L^2$ represents a single bond or a divalent linking group bonding $Y^1$ and $Y^2$ to each other through 1 to 3 atoms. $Y^1$ and $Y^2$, $Y^1$ and $L^2$, or $Y^2$ and $L^2$ may form a ring by being bonded to each other. Each of these groups may be further substituted with a substituent.

$L^2$ represents a single bond or a divalent linking group bonding $Y^1$ and $Y^2$ to each other through 1 to 3 carbon atoms. Each of $R^{x1}$, $R^{x2}$, and Ra has the same definition as $R^{x1}$, $R^{x2}$, and Ra in Formula (II), and the preferred range thereof is also the same.

Among the linking groups exemplified above as the divalent linking group represented by $L^1$, divalent linking groups bonding $Y^1$ and $Y^2$ to each other through 1 to 3 atoms are exemplified as $L^2$, and as the divalent linking groups bonding $Y^1$ and $Y^2$ to each other as described above, those exemplified above as divalent linking groups preferred as $L^1$ are preferable.

Therefore, the alkylene group or the arylene group represented by $L^2$ has the same definition as the alkylene group or the arylene group represented by $L^1$, and the preferred range thereof is also the same.

$L^2$ is preferably a single bond, an alkylene group, a cycloalkylene group, or an arylene group.

Any one of R, $Y^1$, $Y^2$, and $L^2$ in Formula (IV) is preferably a group having at least one cyclic structure.

The compound represented by Formula (I) of the present invention preferably contains a water-soluble functional group.

The water-soluble functional group means a group having a water-soluble group, such as a hydroxy group, a carboxy group or a salt thereof, a sulfo group or a salt thereof, or a phosphoric acid group or a salt thereof, or a group having an ether bond. These water-soluble functional groups exhibit high solubility in water. Accordingly, in a case where a resin which becomes a main component of the composition is a hydrophilic resin or a water-soluble resin, the water-soluble functional group has excellent compatibility with the resin, and hence the effect of the present invention can be further improved. The resin will be specifically described later.

In order to make the compound localized within the polarizer layer or to prevent bleed out, a functional group that interacts with the component constituting the polarizer may be introduced into the compound such that partial structure is not affected. In a case where the component constituting the polarizer is polyvinyl alcohol, examples of the functional group include a substituent forming a covalent bond, such as an acetal group, a carbonyl group, a formyl group, a ketone group, a boronyl group, an boronic acid ester group, or a trialkoxysilyl group, and a substituent forming a hydrogen bonding group, such as fluorine.

For example, in a case where the layer to which the compound represented by Formula (I) of the present invention is added is changed using a polarizer containing polyvinyl alcohol as a main component, the following aspect is also preferable.

In a case where the compound represented by Formula (I) of the present invention is added to a polarizing plate protective film, the compound preferably has, as a substituent, at least one or more functional groups interacting with the component constituting the polarizer as described above in a single molecule. The substituent is preferably one or more groups selected from a formyl group and a boronyl group, and more preferably two or more groups selected from a formyl group and a boronyl group.

In a case where the compound represented by Formula (I) of the present invention is added to a polarizer and an adhesive layer, the compound preferably has, as substituents, at least one or more water-soluble functional groups described above and one or more functional groups interacting with the component constituting the polarizer in a single molecule. The compound more preferably has at least one water-soluble functional group and two or more functional groups interacting with the component constituting the polarizer in a single molecule. The substituent is preferably a sulfo group as a water-soluble functional group and at least one or more groups selected from a formyl group and a boronyl group as the functional group interacting with the component constituting the polarizer.

From the viewpoint of the compatibility between the compound represented by Formula (I) and a highly hydrophilic layer such as the polarizer, it is preferable that the compound has a high degree of solubility in water. The amount of the compound dissolving in 100 ml of water at 25° C. is preferably equal to or greater than 0.1 g, more preferably equal to or greater than 1.0 g, and even more preferably 1.0 g to 30.0 g.

When the compound represented by Formula (I) is added to the polarizing plate protective film, the compound preferably has a molecular weight of 350 to 1,500 and a C log P value, which is a measure of hydrophilicity, of 1.0 to 9.0.

When the compound represented by Formula (I) is added to the adhesive layer or the polarizer layer, the compound preferably has a molecular weight of 100 to 1,000 and a C log P value, which is a measure of hydrophilicity, of −4.0 to 1.0.

P in the C log P value represents a partition coefficient in a n-octanol/water system and can be measured using n-octanol and water. As the partition coefficient, an estimated value obtained using a C log P value estimation program (C log P program incorporated into PC models from Daylight Chemical Information Systems, Inc.) can also be adopted.

The polarizing plate composition of the present invention preferably contains a resin component. It is preferable that the molecular weight of the compound represented by Formula (I) or the preferred range of the C log P value is changed according to the properties of the resin component, particularly, according to whether the resin component is hydrophilic or hydrophobic.

For example, in a case where the resin component is a hydrophobic resin such as a cellulose ester resin, a polyester resin such as polyethylene terephthalate, or an acrylic resin, the molecular weight of the compound represented by Formula (I) is preferably 350 to 1,500, more preferably 400 to 1,000, and even more preferably 400 to 750. Furthermore, the C log P value thereof is preferably 1.0 to 9.0, more preferably 2.0 to 9.0, and even more preferably 2.0 to 8.0.

In contrast, in a case where the resin component is a hydrophilic resin, such as polyvinyl alcohol or acylated or ketalized polyvinyl alcohol, or a water-soluble resin, the molecular weight of the compound represented by Formula (I) is preferably 100 to 1,000, more preferably 140 to 800, and even more preferably 140 to 600. Furthermore, the C log P value thereof is preferably −4.0 to 1.0, more preferably −4.0 to 0.5, and even more preferably −4.0 to 0.

A characteristic active methylene derivative skeleton contributes to the stabilization of a complex (iodine-PVA complex) of polyvinyl alcohol or acylated or ketalized polyvinyl alcohol (PVA) and iodine, although the detail of the mechanism is unclear.

Therefore, particularly for the purpose of improving long-term durability, it is preferable to add the compound represented by Formula (I) of the present invention to the adhesive layer or the polarizer (layer). By being caused to exist in the vicinity of the polarizer (layer), the compound of the present invention stabilizes the iodine-PVA complex in the polarizer (layer), and hence the durability of the polarizer is more effectively improved.

Furthermore, by suppressing diffusion or the like by introducing the functional group interacting with the component constituting the polarizer into the compound, the concentration distribution of the compound or the localization state thereof can be maintained in a desired region.

Specific examples of the compound represented by Formula (I) of the present invention will be shown below, but the present invention is not limited thereto.

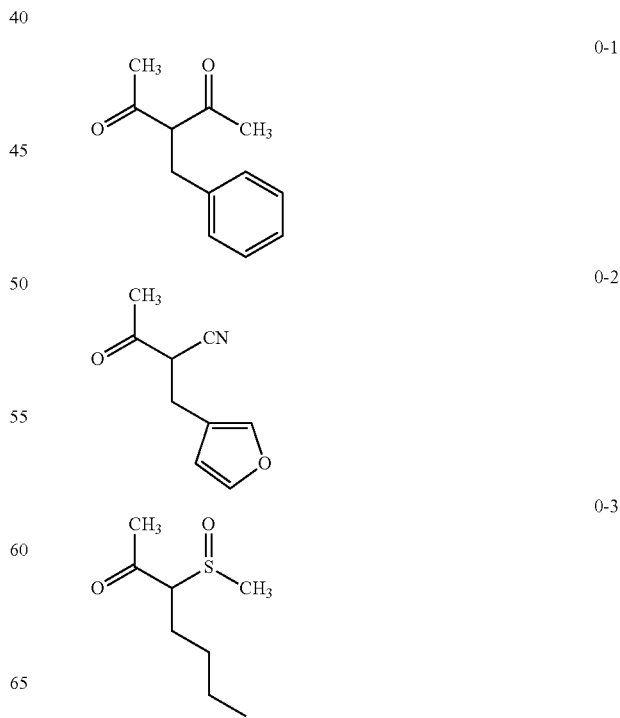

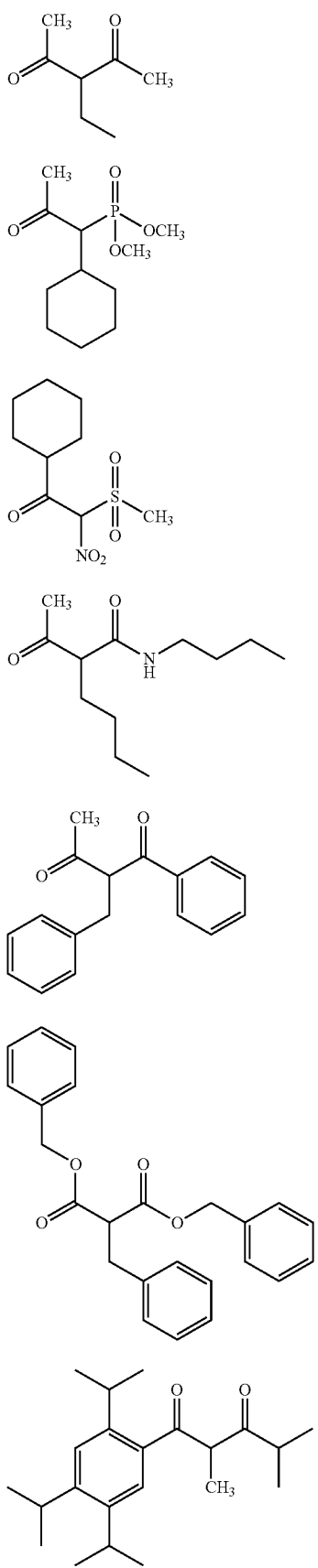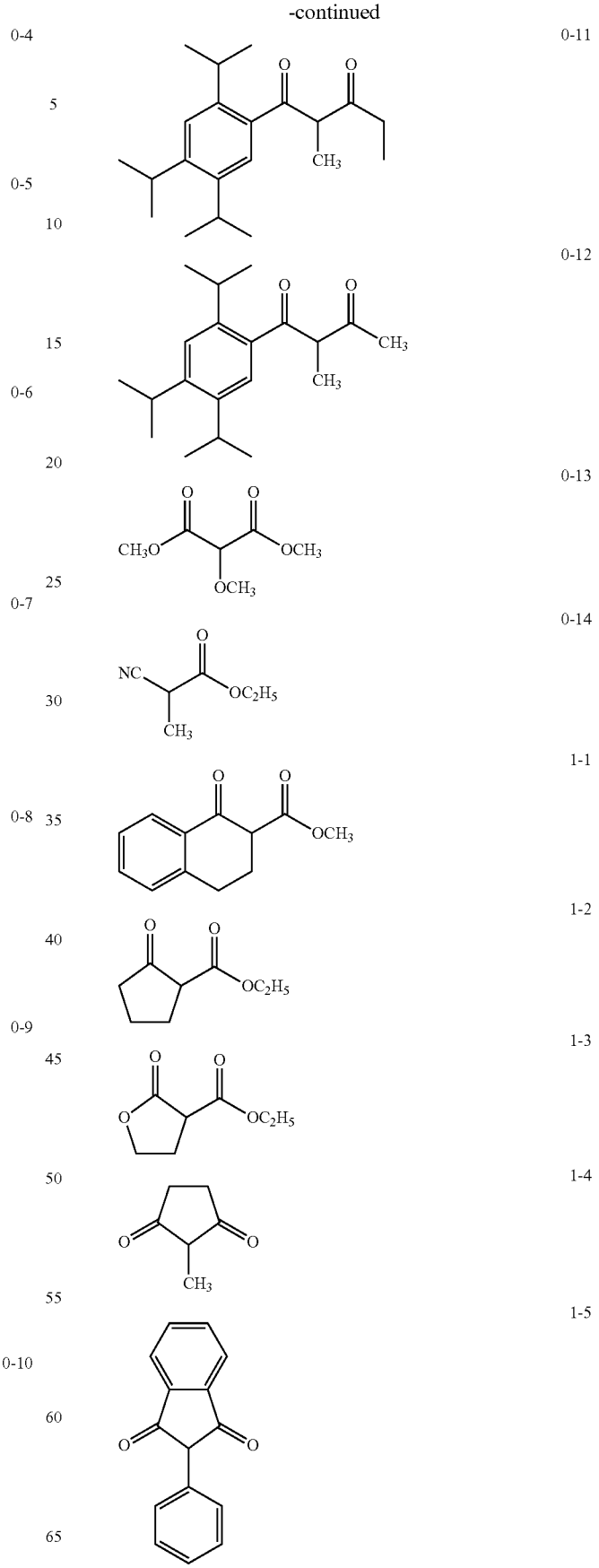

1-6 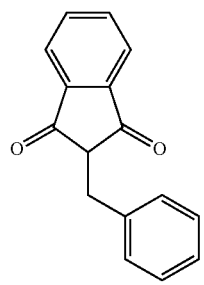
1-7 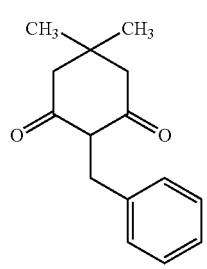
1-8 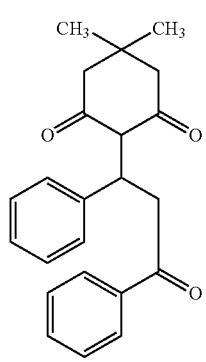
1-9 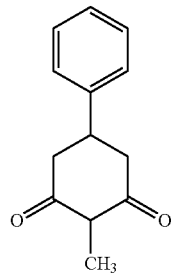
1-10 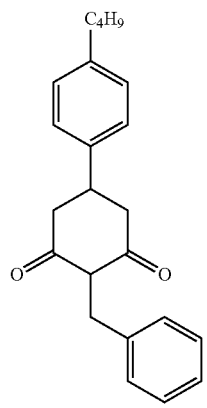
1-11 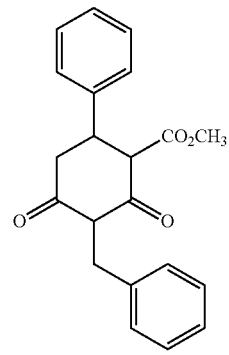
1-12 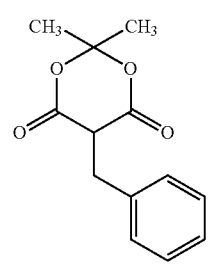
1-13 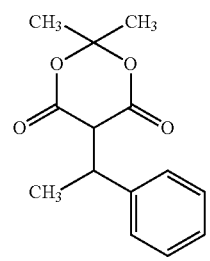
1-14 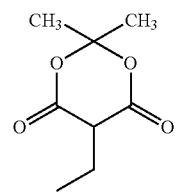
2-1 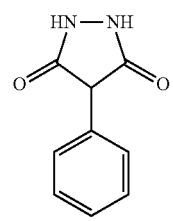
2-2 

-continued
2-3 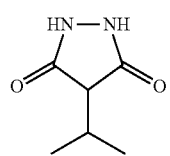
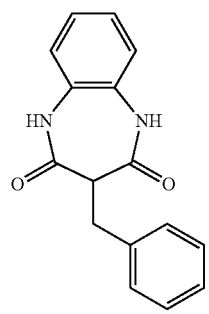
2-8
2-4 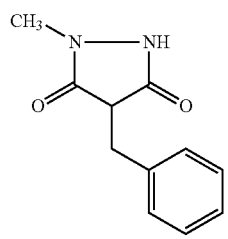
2-5 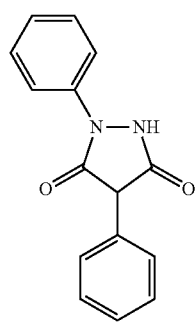
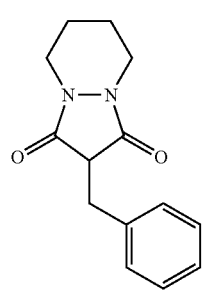
2-9
2-6 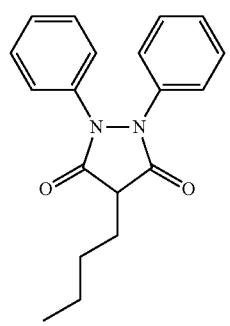
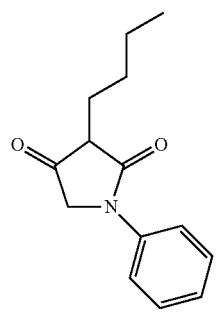
2-10
2-7 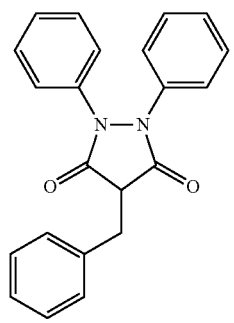
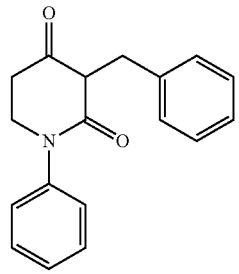
2-11
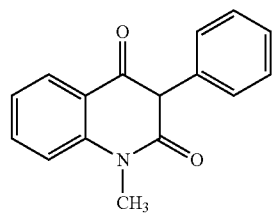
2-12

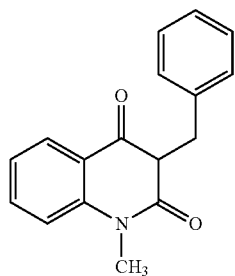
2-13
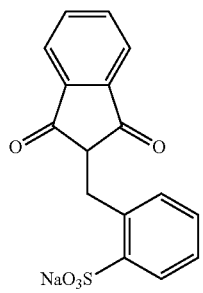
3-4
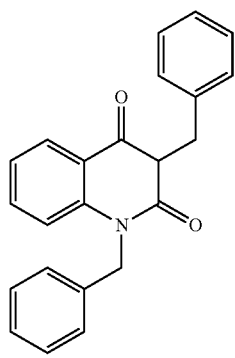
2-14
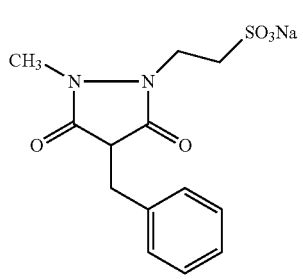
3-5
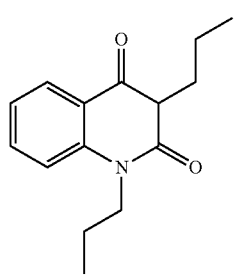
2-15
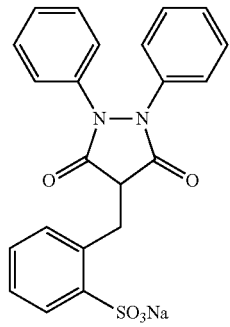
3-6
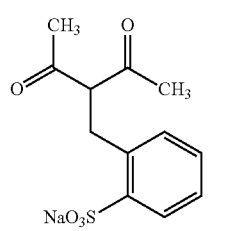
3-1
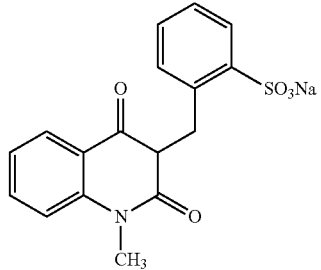
3-7
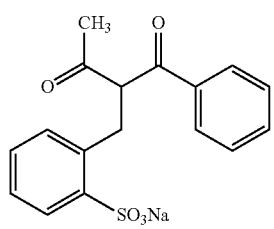
3-2
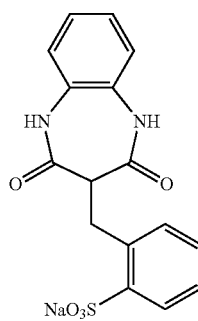
3-8
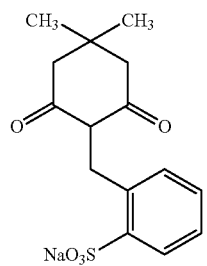
3-3

-continued
3-9
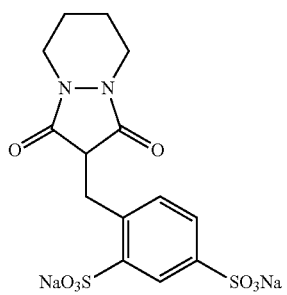
3-10
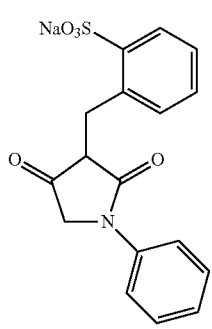
3-11
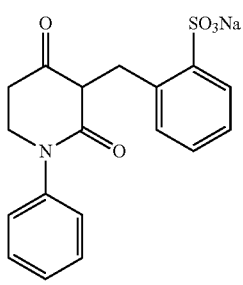
4-1
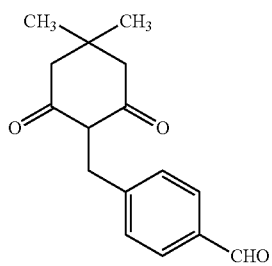
4-2
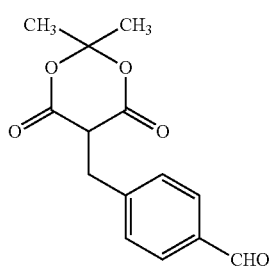
-continued
4-3
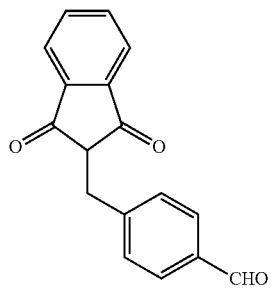
4-4
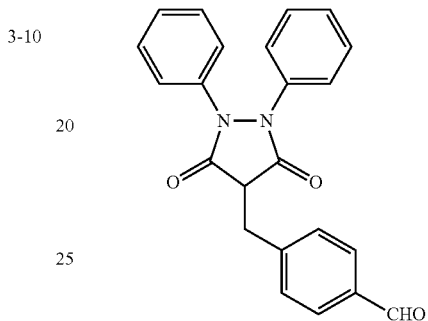
4-5
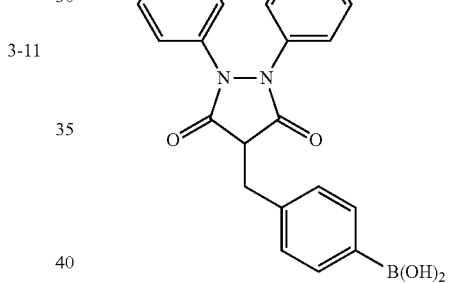
4-6
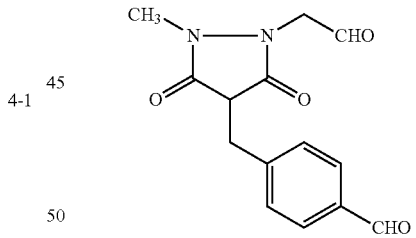
4-7
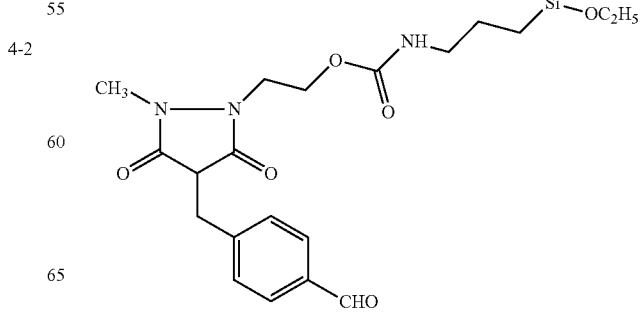

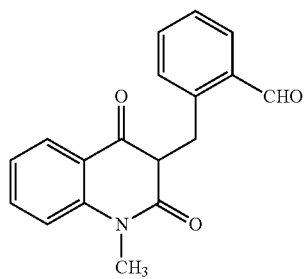
4-8
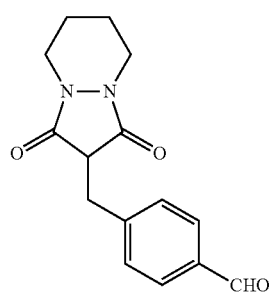
4-9
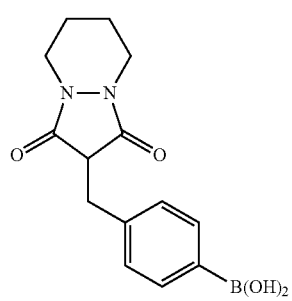
4-10
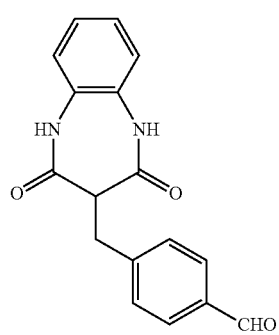
4-11
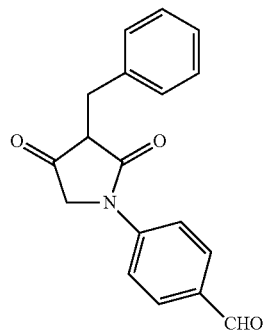
4-12
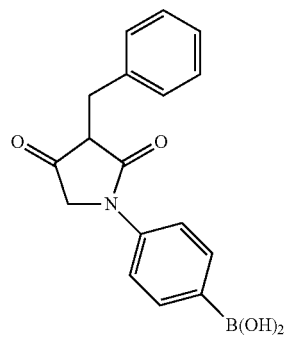
4-13
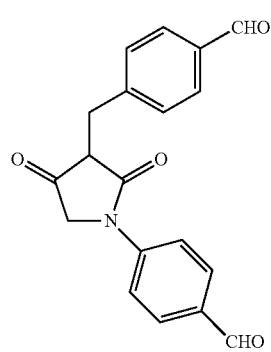
4-14
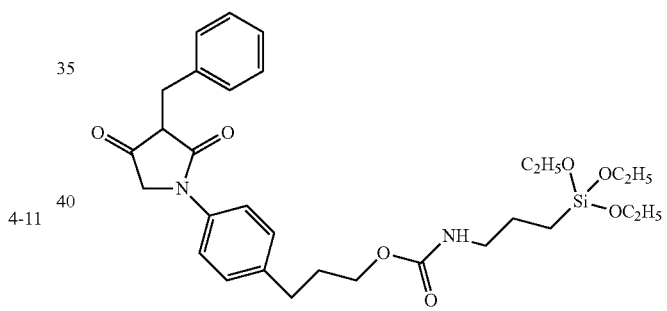
4-15
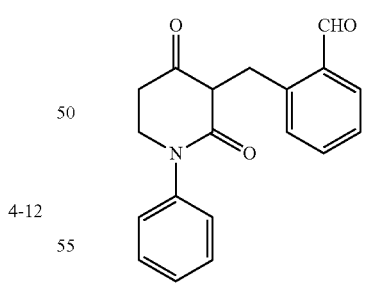
4-16
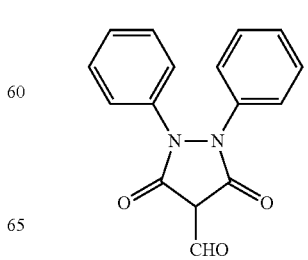
4-17

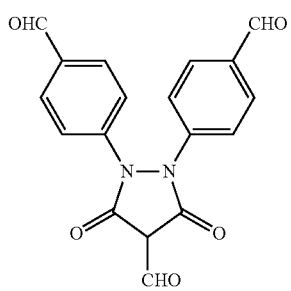

4-18

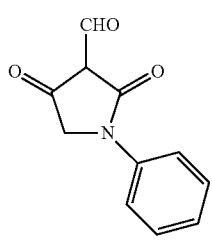

4-19

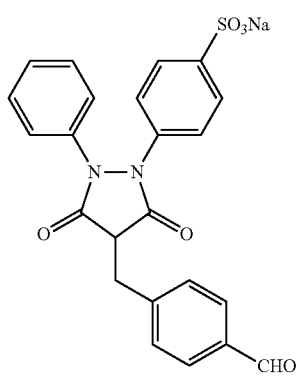

5-1

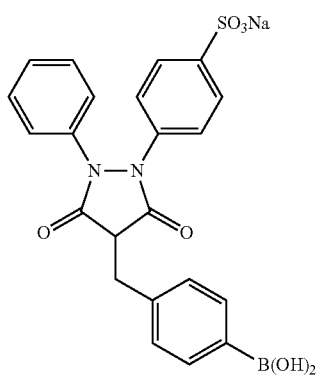

5-2

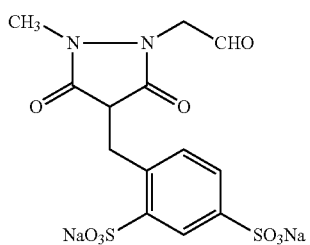

5-3

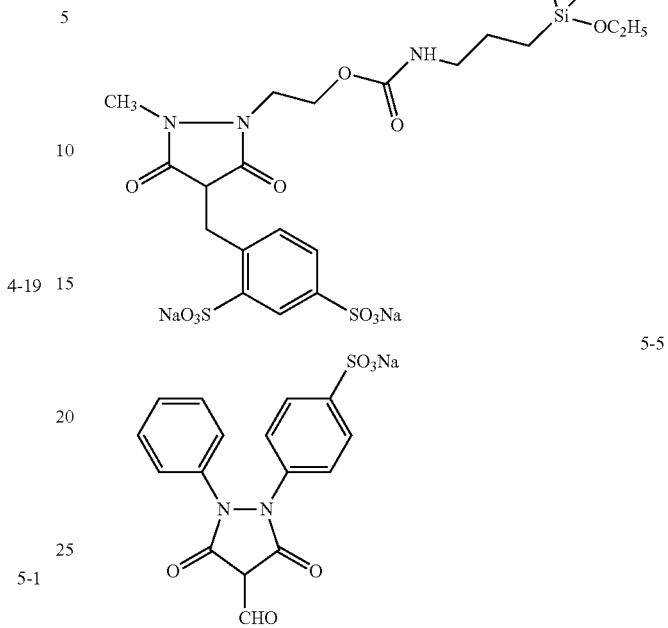

5-4

5-5

The polarizing plate composition of the present invention may contain various materials in addition to the compound represented by Formula (I) of the present invention.

The polarizing plate composition of the present invention preferably further contains a resin, and the content of the compound represented by Formula (I) is preferably 0.01 parts by mass to 30 parts by mass with respect to 100 parts by mass of the resin.

<Resin>

The polarizing plate composition of the present invention is preferably used in a polarizing plate protective film, a polarizer, and an adhesive layer.

The polarizing plate protective film, the polarizer, and the adhesive layer are constituted with a resin component, and the polarizing plate composition of the present invention preferably contains the resin component.

The resin component varies with the use and application of the polarizing plate composition of the present invention.

For example, a hydrophobic resin is used in the polarizing plate protective film, a water-soluble adhesive composed of the resin component is used in the adhesive layer, and a polyvinyl alcohol-based resin (polyvinyl alcohol, acylated or ketalized polyvinyl alcohol, or the like referred to as PVA) is used in the polarizer.

The resin component contained in the polarizing plate composition of the present invention is preferably a cellulose acylate resin, a polycarbonate-based resin, a polyester carbonate-based resin, a polyester-based resin, an acrylic resin such as a polyacrylate-based resin or a polymethacrylate-based resin, a cycloolefin-based resin such as a norbornene-based resin, or a polyvinyl alcohol-based resin including polyvinyl alcohol or acylated or ketalized polyvinyl alcohol, and more preferably a cellulose acylate resin or a polyvinyl alcohol-based resin.

Hereinafter, the polarizing plate composition of the present invention will be described in relation to each of the polarizing plate protective film, the polarizer, and the adhesive layer in which the composition is preferably used. Each of the polarizing plate protective film, the polarizer, and the adhesive layer is formed or manufactured using the polarizing plate composition of the present invention or composed of the polarizing plate composition of the present invention. Accordingly, each of the polarizing plate protective film, the polarizer, and the adhesive layer described below can be substituted with the polarizing plate composition of the present invention (composition of each of the polarizing plate protective film, the polarizer, and the adhesive layer).

[[Polarizing Plate Protective Film]]

The polarizing plate protective film may be in the form of a single-layer film or in the form of a laminate consisting of a plurality of layers.

In a case where the polarizing plate protective film is a laminate consisting of two or more layers, the film preferably has a double or triple layer structure and more preferably has a triple layer structure. In a case where the polarizing plate protective film has a triple layer structure, it is preferable that the film has one core layer (that is, the thickest layer which will be also referred to as a base layer below) and a skin layer A and a skin layer B between which the core layer is interposed. In the present invention, it is preferable that the polarizing plate protective film has a triple layer structure consisting of the skin layer B/core layer/skin layer A. The skin layer A is a layer coming into contact with a metal support, which will be described later, when the polarizing plate protective film is manufactured through a solution film forming process, and the skin layer B is a layer of air interface on the opposite side of the metal support. Herein, the skin layer A and the skin layer B are collectively referred to as a skin layer (or surface layer) as well.

Examples of the resin of the polarizing plate protective film include a cellulose ester-based resin, a polycarbonate-based resin, a polyester carbonate-based resin, a polyester-based resin, an acrylic resin such as polyacrylate-based resin or a polymethacrylate-based resin, a cycloolefin-based resin such as a norbornene-based resin, a polysulfone-based resin, a polyether sulfone-based resin, a polystyrene-based resin, and an imide-based resin such as an olefin maleimide-based resin or a glutarimide-based resin. One kind of these may be used singly, or plural kinds thereof may be used by being mixed together. Among these resins, a cellulose ester-based resin, a polyester-based resin, an acrylic resin, a cycloolefin-based resin, a polystyrene-based resin, and an imide-based resin that have relatively small birefringence induced by molecular alignment and have a relatively small photoelastic coefficient are preferable, a cellulose ester-based resin, a polyester-based resin, an acrylic resin, and a cycloolefin-based resin are more preferable, a cellulose ester-based resin, an acrylic resin, and a cycloolefin-based resin are even more preferable, and a cellulose ester-based resin is particularly preferable.

The content of the compound represented by Formula (I) of the present invention in the polarizing plate protective film or in the composition is not particularly limited, but is preferably 0.01 parts by mass to 30 parts by mass, more preferably 0.01 parts by mass to 10 parts by mass, and particularly preferably 1.0 part by mass to 10 parts by mass, with respect to 100 parts by mass of the resin constituting the polarizing plate protective film. If the content of the compound is as described above, the effect of inhibiting coloring of the film that is an effect of the present invention can be sufficiently exhibited, and the transparency of the film can be maintained.

In a case where the polarizing plate protective film contains two or more kinds of compound represented by Formula (I), the total content thereof is preferably within the range described above.

Hereinafter, as an example of resin which is contained in the polarizing plate composition of the present invention and can become a main component of the polarizing plate protective film, an acrylic resin, a cycloolefin-based resin, a polyester-based resin such as polyethylene terephthalate, and cellulose acylate which is a cellulose ester-based resin will be described.

[Acrylic Resin]

In the present specification, an "acrylic resin" includes not only an acrylic resin but also a methacrylic resin. Therefore, hereinafter, the "acrylic resin" will be also described as a "(meth)acrylic resin".

In one of the preferred aspects of the polarizing plate protective film of the present invention, the film contains the (meth)acrylic resin as a main component.

Herein, the main component means a component whose content in the polarizing plate protective film is the highest in terms of mass ratio among the components contained in the film. The content of the (meth)acrylic resin in the polarizing plate protective film is preferably 10% by mass to 100% by mass, more preferably 20% by mass to 100% by mass, and even more preferably 30/o by mass to 100% by mass.

The (meth)acrylic resin is obtained by polymerizing a (meth)acrylic monomer, and may contain a structural unit obtained from a monomer other than the (meth)acrylic monomer. Particularly, it is preferable that the (meth)acrylic resin is obtained by polymerizing a monomer composition containing an ultraviolet-absorbing monomer and a (meth)acrylic monomer.

The ultraviolet-absorbing monomer is preferably a benzophenone-based ultraviolet-absorbing monomer or a benzotriazole-based ultraviolet-absorbing monomer, and more preferably a benzotriazole-based ultraviolet-absorbing monomer.

One kind of ultraviolet-absorbing monomer may be used singly, or two or more kinds thereof may be used in concurrently.

As the (meth)acrylic monomer, any of appropriate (meth)acrylic monomers can be adopted within a range that does not impair the effects of the present invention. Examples of such a (meth)acrylic monomer include (meth)acrylic acid and a (meth)acrylic acid ester. Among these, a (meth)acrylic acid alkyl ester having 1 to 6 carbon atoms is preferable, and methyl methacrylate is more preferable.

One kind of (meth)acrylic monomer may be used singly, or two or more kinds thereof may be used concurrently.

As the (meth)acrylic resin, a (meth)acrylic resin having a lactone ring structure is preferable because it has high heat resistance, high transparency, and high mechanical strength.

As the (meth)acrylic resin having a lactone ring structure, (meth)acrylic resins are preferable which are described in JP2000-230016A, JP2001-151814A, JP2002-120326A, JP2002-254544A, JP2005-146084A, JP2006-171464A, and the like, and manufactured from a monomer composition obtained by adding the ultraviolet-absorbing monomer described above to a monomer composition used at the time of manufacturing a (meth)acrylic resin having a lactone ring structure.

The weight average molecular weight (Mw) of the (meth)acrylic resin is preferably equal to or greater than 1,000 and equal to or less than 2,000,000, more preferably equal to or greater than 5,000 and equal to or less than 1,000,000, and even more preferably equal to or greater than 10,000 and equal to or less than 1,000,000.

[Cycloolefin-Based Resin]

The cycloolefin-based resin preferably has at least one polar group, and preferably exhibits a certain degree of moist permeability in a case where it is made into the polarizing plate protective film.

If the cycloolefin-based resin has at least one polar group, the solubility of the resin in an organic solvent such as dichloromethane is improved, and hence the solution film forming process can be performed. The solution film forming process is preferable because a film can be formed at a lower temperature in this process than in a melting film forming process, and the decomposition or volatilization of additives does not easily occur.

Examples of the polar group include a hydroxyl group, an alkoxy group having 1 to 10 carbon atoms, an acyloxy group having 1 to 10 carbon atoms, an alkoxycarbonyl group having 2 to 10 carbon atoms, an aryloxycarbonyl group, a cyano group, an amide group, an imide ring-containing group, a triorganosiloxy group, a triorganosilyl group, an amino group, an acyl group, an alkoxysilyl group having 1 to 10 carbon atoms, a sulfonyl-containing group, and a carboxy group. Specific examples of these polar groups include methoxy and ethoxy as the alkoxy group, an alkylcarbonyloxy group such as acetoxy or propionyloxy and an arylcarbonyloxy group such as benzoyloxy as the acyloxy group, methoxycarbonyl and ethoxycarbonyl as the alkoxycarbonyl group, phenoxycarbonyl, naphthyloxycarbonyl, fluorenyloxycarbonyl, and biphenyloxycarbonyl as the aryloxycarbonyl group, trimethylsiloxy and triethylsiloxy as the triorganosiloxy group, trimethylsilyl and triethylsilyl as the triorganosilyl group, a primary amino group as the amino group, and trimethoxysilyl and triethoxysilyl as the alkoxysilyl group.

Among these, an alkoxycarbonyl group is preferable, and a methoxycarbonyl group is more preferable.

The cycloolefin-based resin is preferably a resin represented by the following Formula (RC).

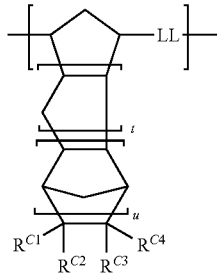

Formula (RC)

In Formula (RC), t represents 0 or 1, and u represents 0 or an integer of equal to or greater than 1. LL represents a vinylene group or an ethylene group, and each of $R^{C1}$ to $R^{C4}$ independently represents a hydrogen atom, a halogen atom, a substituted or unsubstituted hydrocarbon group or polar group having 1 to 30 carbon atoms. The hydrocarbon group may be bonded through a linking group having an oxygen atom, a nitrogen atom, a sulfur atom, or a silicon atom. Herein, two groups such as $R^{C1}$ and $R^{C2}$ or $R^{C3}$ and $R^{C4}$ may form a divalent hydrocarbon group, a carbon ring, or a heterocyclic ring by being bonded to each other. Each of a plurality of LL's, $R^{C1}$'s, $R^{C2}$'s, $R^{C3}$'s, and $R^{C4}$'s may be the same as or different from each other. From the viewpoint of improving suitability for the solution film forming process, at least one of $R^{C1}$ to $R^{C4}$ is preferably a polar group.

u is preferably an integer of 0 to 2, and more preferably 0 or 1.

Examples of the halogen atom represented by $R^{C1}$ to $R^{C4}$ include a fluorine atom, a chlorine atom, and a bromine atom.

Examples of the hydrocarbon group having 1 to 30 carbon atoms represented by $R^{C1}$ to $R^{C4}$ include an alkyl group such as methyl, ethyl, or propyl, a cycloalkyl group such as cyclopentyl or cyclohexyl, an alkenyl group such as vinyl, allyl, or propenyl, and an aryl group such as phenyl, biphenyl, naphthyl, or anthracenyl. These hydrocarbon groups may be substituted, and examples of the substituent include a halogen atom such as a fluorine atom, a chlorine atom, or a bromine atom and a phenylsulfonyl group.

The hydrocarbon group described above may be bonded to a cyclic structure directly or through a linking group (linkage). Examples of the linking group include a divalent hydrocarbon group having 1 to 10 carbon atoms, such as an alkylene group represented by $-(CH_2)_m-$ (m represents an integer of 1 to 10) and a linking group containing an oxygen atom, a nitrogen atom, a sulfur atom, or a silicon atom. Specific examples of the linking group containing an oxygen atom, a nitrogen atom, an iodine atom, or a silicon atom include a carbonyl group [$-C(=O)-$], a carbonyloxy group [$-C(=O)O-$], an oxycarbonyl group [$-OC(=O)-$], a sulfonyl group [$-SO_2-$], an ether bond [$-O-$], a thioether bond [$-S-$], an imino group [$-NH-$], an amide bond [$-NH(=O)-$, $-C(=O)NH-$], a siloxane bond [$-OSi(R^{CA})_2-$ (in the formula, $R^{CA}$ is an alkyl group such as methyl or ethyl)], a group in which two or more kinds of groups described above are linked to each other, and the like.

Two groups such as $R^{C1}$ and $R^{C2}$ or $R^{C3}$ and $R^{C4}$ may form a divalent hydrocarbon group, a carbon ring, or a heterocyclic ring by being bonded to each other. However, it is preferable that they do not form a divalent hydrocarbon group, a carbon ring, or a heterocyclic ring. The carbon ring or the heterocyclic ring may have a monocyclic structure or a polycyclic structure and may be an aromatic ring or a non-aromatic ring. However, it is preferable that the carbon ring or the heterocyclic ring is preferably a non-aromatic ring.

It is preferable that at least one of $R^{C1}$ to $R^{C4}$ is a polar group, and each of the groups other than the polar group represented by $R^{C1}$ to $R^{C4}$ is preferably a hydrogen atom.

The cycloolefin-based resin can be synthesized with reference to the method described in paragraphs "0039" to "0068" of JP2001-114836A.

The glass transition temperature (Tg) of the cycloolefin-based resin measured by a differential scanning calorimeter (DSC) is preferably equal to or higher than 70° C., more preferably 90° C. to 185° C., even more preferably 100° C. to 165° C., and particularly preferably 120° C. to 160° C.

The weight average molecular weight (Mw) of the cycloolefin-based rein is preferably 5,000 to 1,000,000, and more preferably 8,000 to 200,000.

The saturated water absorption rate of the cycloolefin-based resin is preferably equal to or less than 1% by mass, and more preferably equal to or less than 0.8% by mass.

The intrinsic viscosity (ηinh) of the cycloolefin-based resin measured at 30° C. in chloroform is preferably 0.1 dl/g to 1.5 dl/g, and more preferably 0.4 dl/g to 1.2 dl/g. The limiting viscosity [η] of the cycloolefin-based resin measured at 135° C. in decalin is preferably 0.01 dl/g to 20 dl/g, more preferably 0.03 dl/g to 10 dl/g, and even more preferably 0.05 dl/g to 5 dl/g. The melt flow rate (MFR) of the cycloolefin-based resin measured at 260° C. under a load of 2.16 kg based on ASTM D1238 is preferably 0.1 g/10 min to 200 g/10 min, more preferably 1 g/10 min to 100 g/10 min, and even more preferably 5 g/10 min to 50 g/10 min.

The softening point of the cycloolefin-based resin measured using a thermomechanical analyzer (TMA) is preferably equal to or higher than 30° C., more preferably equal to or higher than 70° C., and even more preferably 80° C. to 260° C.

The hydrogenation rate of a hydrogenated polymer of the cycloolefin-based resin that is measured by $^1$H-NMR at 60 MHz is preferably equal to or greater than 50%, more preferably equal to or greater than 90%, and even more preferably equal to or greater than 98%. The higher the hydrogenation rate, the more the obtained cycloolefin-based resin film stable against heat or light. The amount of gel contained in the hydrogenated polymer is preferably equal to or less than 5% by mass and more preferably equal to or less than 1% by mass.

It is preferable that the cycloolefin-based resin has amorphousness or low crystallinity. The degree of crystallization of the resin measured by X-ray diffraction method is preferably equal to or less than 20%, more preferably equal to or less than 10%, and even more preferably equal to or less than 2%.

[Polyester-Based Resin]

As the polyester-based resin, it is possible to use polyethylene terephthalate, polyethylene isophthalate, polybutylene terephthalate, poly(1,4-cyclohexylenedimethylene terephthalate), polyethylene-2,6-naphthalate, and the like. The polyester-based resin may contain other copolymerization components.

In one of the preferred aspects of the polarizing plate protective film of the present invention, the film contains the polyester-based resin as a main component. The content of the polyester-based resin in the polarizing plate protective film is preferably 70% by mass to 100% by mass, more preferably 80% by mass to 100% by mass, and even more preferably 90% by mass to 100% by mass.

The polyester-based resin has high transparency and excellent thermal and mechanical characteristics and enables control of retardation through stretching processing.

Particularly, polyethylene terephthalate is preferable because this resin is highly versatile and easily obtained, has great intrinsic birefringence, and makes it possible to relatively easily obtain great retardation even if the film is thin.

The polyester-based resin can be synthesized through an ester exchange reaction or a polycondensation reaction between dicarboxylic acid and diol by a common method.

The polyester film can be manufactured according to a general polyester film manufacturing method. Examples thereof include a method in which a polyester resin is melted, non-alignment polyester extrusion-molded in a sheet shape is stretched in a vertical direction at a temperature equal to or higher than the glass transition temperature thereof by exploiting a speed difference between rolls, and then the resulting film is stretched in a horizontal direction by using a tenter and then subjected to a thermal treatment.

The polyester film may be a uniaxially stretched film or a biaxially stretched film.

In manufacturing the polyester film, each of the vertical stretching temperature and the horizontal stretching temperature is preferably 80° C. to 130° C., and particularly preferably 90° C. to 120° C. The horizontal stretching ratio is preferably 1.0-fold to 3.5-fold, and particularly preferably 1.0-fold to 3.0-fold. The horizontal stretching ratio is preferably 2.5-fold to 6.0-fold, and particularly preferably 3.0-fold to 5.5-fold. In order to control the retardation to be within a desired range, it is preferable to control a ratio between the vertical stretching ratio and the horizontal stretching ratio. It is not preferable that the difference between the vertical stretching ratio and the horizontal stretching ratio is too small because then the retardation is not easily increased. For increasing the retardation, it is also preferable to set the stretching temperature to be low. In the thermal treatment following the stretching, the treatment temperature is preferably 100° C. to 250° C., and particularly preferably 180° C. to 245° C.

The number average molecular weight of the polyester-based resin is preferably equal to or greater than 5.000, more preferably equal to or greater than 6,000, and even more preferably equal to or greater than 10,000. The glass transition temperature of the polyester-based resin is not particularly limited, but is preferably 20° C. to 90° C. and more preferably 30° C. to 80° C. The intrinsic viscosity of the polyethylene terephthalate resin is 0.62 dl/g.

[Cellulose Acylate]

In the present invention, in a case where cellulose acylate is used as a main component of the polarizing plate protective film, one kind of cellulose acylate may be used, or two or more kinds thereof may be used. For example, as the cellulose acylate, cellulose acetate having only an acetyl group as an acyl substituent or cellulose acylate having a plurality of different acyl substituents may be used. Furthermore, the cellulose acylate may be a mixture of different cellulose acylates.

The cellulose as a material of the cellulose acylate used in the present invention includes cotton linter, wood pulp (broad-leaved tree pulp and needle-leaved tree pulp), and the like. Any type of cellulose obtained from any raw material cellulose can be used, and in some case, a mixture thereof may be used. As the raw material cellulose, it is possible to use cellulose described in, for example, Marusawa, Uda, "Course in Plastic Material (17) Cellulose-based Resin", NIKKAN KOGYO SHIMBUN, LTD (1970) or Japan Institute of Invention and Innovation, Publication of technical report, Technique No. 2001-1745 (pp 7-8).

In the present invention, the cellulose acylate may have only one kind of acyl group, or two or more kinds of acyl group may be contained in a single cellulose compound. The cellulose acylate used in the present invention preferably has an acyl group having two or more carbon atoms as a substituent. The acyl group having two or more carbon atoms may be an aliphatic or aromatic acyl group and is not particularly limited. Examples of the acyl group include an alkylcarbonyl group, an alkenylcarbonyl group, an aromatic carbonyl group, an aromatic alkylcarbonyl group, and the like of cellulose, and each of these may further has a substituted group. Preferred examples thereof include acetyl, propionyl, butanoyl, heptanoyl, hexanoyl, octanoyl, decanoyl, dodecanoyl, tridecanoyl, tetradecanoyl, hexadecanoyl, octadecanoyl, isobutanoyl, tert-butanoyl, cyclohexanecarbonyl, oleoyl, benzoyl, naphthylcarbonyl, cinnamoyl, and the like. Among these, acetyl, propionyl, butanoyl, dodecanoyl, octadecanoyl, tert-butanoyl, oleoyl, benzoyl, naphthylcarbonyl, cinnamoyl, and the like are more preferable, and acetyl, propionyl, and butanoyl are even more preferable.

It is preferable that the cellulose acylate used in the present invention has an acyl group having 2 to 4 carbon atoms as a substituent. In a case where two or more kinds of acyl group is used, one kind of acyl group is preferably an acetyl group, and the other acyl group having 2 to 4 carbon atoms used is preferably a propionyl group or a butyryl group. If the cellulose acylate described above is used, a solution having preferable solubility can be prepared, and particularly, a solution having excellent solubility in a non-chlorine-based organic solvent can be prepared. Furthermore, a solution having low viscosity and excellent filterability can be prepared.

The glucose-$\beta$-1,4-glucose unit constituting cellulose has free hydroxy groups in the 2-position, 3-position, and 6-position. The cellulose acylate is a polymer in which some or all of the hydroxy groups are acylated by an acyl group.

A degree of acyl substitution shows a degree of acylation of the hydroxy groups of the cellulose located in the 2-position, 3-position, and 6-position. In a case where all of the hydroxy groups in the 2-position, 3-position, and 6-position of all of the glucose units are acylated, the total degree of acyl substitution is 3. For example, in a case where acylation occurs only in the 6-position of all of the glucose units, the total degree of acyl substitution is 1. Likewise, in a case where, among all of the hydroxy groups of all of the glucose molecules, the hydroxy group in either the 6-position or the 2-position of each of the glucose units is acylated, the total degree of acyl substitution is 1.

That is, in a case where all of the hydroxy groups in the glucose molecules are acylated, the total degree of acyl substitution becomes 3, showing the extent of acylation.

Specifically, the degree of acyl substitution can be measured based on the method described in Tezuka et al., Carbohydrate. Res., 273, 83-91 (1995) or the method specified by ASTM-D817-96.

Provided that the total degree of acyl substitution of the cellulose acylate used in the present invention is A, A is preferably equal to or greater than 1.5 and equal to or less than 3.0 ($1.5 \leq A \leq 3.0$), more preferably 2.00 to 2.97, even more preferably equal to or greater than 2.50 and less than 2.97, and particularly preferably 2.70 to 2.95.

Regarding cellulose acetate using only an acetyl group as the acyl group of the cellulose acylate, provided that the total degree of acetyl substitution thereof is B, B is preferably equal to or greater than 2.0 and equal to or less than 3.0 ($2.0 \leq B \leq 3.0$), more preferably 2.0 to 2.97, even more preferably equal to or greater than 2.5 and less than 2.97, still more preferably equal to or greater than 2.55 and less than 2.97, particularly preferably 2.60 to 2.96, and most preferably 2.70 to 2.95.

The compound represented by Formula (I) of the present invention is particularly effective for cellulose acylate having the total degree of acyl substitution A of greater than 2.00.

In a case where the cellulose acylate film as an optical film of the present invention is a laminate (constituted with a plurality of layers), within the cellulose acylate film, the total degree of acyl group substitution of cellulose acylate in each layer may be uniform, or a plurality of cellulose acylate compounds having different degrees of acyl group substitution or different acyl groups may be present as a mixture in a single layer.

In a case where acid anhydride or acid chloride is used as an acylation agent for acylating cellulose, as an organic solvent which is a reaction solvent, methylene chloride, an organic acid such as acetic acid, or the like is used.

In a case where the acylation agent is acid anhydride, a protonic catalyst such as sulfuric acid is preferably used as a catalyst. In a case where the acylation agent is acid chloride (for example, $CH_3CH_2COCl$), a basic compound is used as a catalyst.

The most common industrial synthesis method of a mixed fatty acid ester of cellulose is a method of acylating cellulose by using a fatty acid (acetic acid, propionic acid, valeric acid, or the like) corresponding to an acetyl group or other acyl groups or using a mixed organic acid component containing acid anhydride of the fatty acid.

The cellulose acylate can be synthesized by, for example, the method described in JP1998-45804A (JP-H10-45804A).

From the viewpoint of moisture permeability, the polarizing plate protective film of the present invention, particularly, the cellulose acylate film contains cellulose acylate preferably in an amount of 5% by mass to 99% by mass, more preferably in an amount of 20% by mass to 99% by mass, and particularly preferably in an amount of 50% by mass to 95% by mass, with respect to the total solid content.

[Additive]

In addition to the compound represented by Formula (I) of the present invention, additives including a retardation adjuster (a retardation inducer and a retardation reducer), a plasticizer such as a polycondensed ester compound (polymer), polyester of polyol, a phthalic acid ester, a phosphoric acid ester, or a sugar ester, an ultraviolet absorber, an antioxidant, a matting agent, and the like can be added to the polarizing plate protective film of the present invention, particularly, to the cellulose acylate film.

In the present specification, a compound group is described using "-based" as in the "phosphoric acid ester-based compound" in some cases. In these cases, the "phosphoric acid ester-based compound" has the same definition as the "phosphoric acid ester compound".

As the retardation reducer, the retardation inducer, the plasticizer, the polyol ester-based or polycondensed ester-based hydrophobizing agent, the hydrocarbon compound derivative-based plasticizer, the antioxidant, the ultraviolet absorber, and the matting agent, the compounds or materials described in paragraphs "0061" to "0126" of JP2013-28782A are preferable. The entirety of the disclosure of the document including the content of the compounds or materials is preferably incorporated herein as a part of the present specification.

(Radical Scavenger)

The polarizing plate protective film preferably contains a radical scavenger. As the radical scavenger, HALS and reductones are preferably used.

As HALS, compounds having a 2,2,6,6-tetramethyl-pyridine ring are particularly preferable. Among these, the compounds in which a hydrogen atom, an alkyl group, an alkoxy group, a hydroxy group, an oxyradical group (—O.), an acyloxy group, or an acyl group is in the 1-position of piperidine are preferable, and the compounds in which a hydrogen atom, a hydroxy group, an acyloxy group, an amino group that may have a substituent, an alkoxy group, or an aryloxy group is in the 4-position are more preferable. Furthermore, the compounds having 2 to 5 of 2,2,6,6-tetremethyl-piperidine rings in a molecule are also preferable.

Examples of such compounds include SUNLIZER HA-622 (trade name, manufactured by SORT CO., LTD.), CHIMASSORB 2020 FDL, TINUVIN 770 DF, TINUVIN 152, TINUVIN 123, FLAMESTAB NOR 116 FF (trade names, all manufactured by BASF Corporation (former Ciba Specialty Chemicals, Inc.)), CYASORB UV-3346 and CYASORB UV-3529 (trade names, all manufactured by SUN CHEMICAL COMPANY LTD.).

Examples of the reductones include the compounds exemplified in paragraphs "0014" to "0034" of JP1994-27599A (JP-H06-27599A), the compounds exemplified in paragraphs "0012" to "0020" of JP1994-110163A (JP-H06-110163A), and the compounds exemplified in paragraphs "0022" to "0031" of JP1996-114899A (JP-H08-114899A).

Furthermore, ascorbic acid and erythorbic acid substituted with an oil-soluble group (for example, a fatty acid ester of a hydroxy group) can be preferably used, and examples thereof include a stearic acid L-ascorbyl ester, a tetraisopalmitic acid L-ascorbyl ester, a palmitic acid L-ascorbyl ester, a palmitic acid erythorbyl ester, a tetraisopalmitic acid erythorbyl ester, and the like. Among these, those having an ascorbic acid skeleton are preferable, and a myristic acid ester, a palmitic acid ester, and a stearic acid ester of L-ascorbic acid are particularly preferable.

The content of the radical scavenger in the polarizing plate protective film is preferably 0.001 parts by mass to 2.0 parts by mass, and more preferably 0.01 parts by mass to 1.0 part by mass, with respect to 100 parts by mass of the resin constituting the polarizing plate protective film.

(Deterioration Preventive Agent)

A deterioration preventive agent (for example, an antioxidant, a peroxide decomposer, a radical inhibitor, a metal deactivator, an acid trapping agent, or amine) may be added to the polarizing plate protective film. An ultraviolet absorber is one of the deterioration preventive agents. These deterioration preventive agents are described in JP1985-235852A (JP-S60-235852A), JP1991-199201A (JP-H03-199201A), JP1993-197073A (JP-H05-197073A), JP1993-194789A (JP-H05-194789A), JP1993-271471A (JP-H05-271471A), JP1994-107854A (JP-H06-107854A), JP1994-118233A (JP-H06-118233A), JP1994-148430A (JP-H06-148430A), JP1995-11056A (JP-H07-11056A), JP1995-11055A (JP-H07-11055A), JP1996-29619A (JP-H08-29619A), JP1996-239509A (JP-H08-239509A), JP2000-204173A, and JP2006-251746A.

The radical scavenger described above also prevents deterioration, and amines are also known as deterioration preventive agents. Examples thereof include the compounds described in paragraphs "0009" to "0080" of JP1993-194789A (JP-H05-194789A) and aliphatic amine such as tri-n-octylamine, triisooctylamine, tris(2-ethylhexyl)amine, or N,N-dimethyldodecylamine.

It is also preferable to use polyamines having two or more amino groups, and as the polyamines, those having two or more primary or secondary amino groups are preferable. Examples of the compounds having two or more amino groups include a nitrogen-containing heterocyclic compound (a compound having a pyrazolidine ring, a piperazine ring, or the like), a polyamine-based compound (linear or cyclic polyamine such as diethylenetriamine, tetraethylenepentamine, N,N'-bis(aminoethyl)-1,3-propanediamine, N,N,N',N'',N''-pentakis(2-hydroxypropyl)diethylenetriamine, polyethyleneimine, modified polyethyleneimine, or a compound containing cyclam as a basic skeleton), and the like.

The content of the deterioration preventive agent in the polarizing plate protective film is preferably 1 ppm to 10%, more preferably 1 ppm to 5.0%, and even more preferably 10 ppm to 1.0%, based on mass.

(Peeling Accelerator)

Any peeling accelerator may be added to the polarizing plate protective film.

The peeling accelerator is preferably an organic acid, a polycarboxylic acid derivative, a surfactant, or a chelating agent. For example, it is possible to preferably use the compounds described in paragraphs "0048" to "0081" of JP2006-45497A, the compounds described in paragraphs "0077" to "0086" of JP2002-322294A, the compounds described in paragraphs "0030" to "0056" of JP2012-72348A, and the like. The content of the peeling accelerator in the polarizing plate protective film is preferably 1 ppm to 5.0%, and more preferably 1 ppm to 2.0%, based on mass.

Hereinafter, preferred physical properties of the polarizing plate protective film will be described using a cellulose acylate film as a representative example, but the polarizing plate protective film is not limited to cellulose acylate.

[Modulus of Elasticity (Tensile Modulus of Elasticity)]

The cellulose acylate film exhibits a modulus of elasticity (tensile modulus of elasticity) sufficient for practical use. The range of the modulus of elasticity is not particularly limited. However, from the viewpoint of manufacturing suitability and handleability, the modulus of elasticity is preferably 1.0 GPa to 7.0 GPa, and more preferably 2.0 GPa to 6.5 GPa. By being added to the cellulose acylate film, the compound represented by Formula (I) of the present invention improves the modulus of elasticity by making the cellulose acylate film hydrophobic. From this standpoint, the present invention is also advantageous.

(Photoelastic Coefficient)

The absolute value of a photoelastic coefficient of the cellulose acylate film is preferably equal to or less than $8.0 \times 10^{-12}$ m$^2$/N, more preferably equal to or less than $6 \times 10^{-12}$ m$^2$/N, and even more preferably equal to or less than $5 \times 10^{-12}$ m$^2$/N. Reduction of the photoelastic coefficient of the cellulose acylate film makes it possible to inhibit the occurrence of unevenness at high temperature and high humidity when the cellulose acylate film is incorporated as a polarizing plate protective film into a liquid crystal display device. Unless otherwise specified, the photoelastic coefficient is measured and calculated by the following method.

The lower limit of the photoelastic coefficient is not particularly limited but is substantially equal to or greater than $0.1 \times 10^{-12}$ m$^2$/N.

The cellulose acylate film is cut in 3.5 cm×12 cm, the retardation (Re) is measured under a load of 0 g, 250 g, 500 g, 1,000 g, and 1,500 g respectively by using an ellipsometer (M150 [trade name], manufactured by JASCO Corporation), and the photoelastic coefficient is calculated from the slope of a line showing the change in Re according to stress.

(Moisture Content)

The moisture content of the cellulose acylate film can be evaluated by measuring equilibrium moisture content at a certain temperature and humidity. The equilibrium moisture content is determined in a manner in which a sample is left for 24 hours at a certain temperature and humidity, the amount of moisture in the sample in equilibrium is then measured by a Karl Fischer method, and the amount of moisture (g) is divided by the mass of the sample (g).

The moisture content of the cellulose acylate film at 25° C. and a relative humidity of 80% is preferably equal to or less than 5% by mass, more preferably equal to or less than 4% by mass, and even more preferably less than 3% by mass. The reduction of the moisture content of the cellulose acylate film makes it possible to inhibit the occurrence of display unevenness of a liquid crystal display device at high temperature and high humidity when the optical film of the present invention including the cellulose acylate film is incorporated as a polarizing plate protective film into the liquid crystal display device. The lower limit of the moisture content is not particularly limited but is substantially equal to or greater than 0.1% by mass.

(Moisture Permeability)

The moisture permeability of the cellulose acylate film can be evaluated in a manner in which the mass of water vapor passing through a sample for 24 hours is measured in an atmosphere with a temperature of 40° C. and a relative humidity of 90% based on the test for moisture permeability (cup method) of JIS Z0208, and the result is expressed in terms of the mass of water vapor passing through the sample for 24 hours per area of 1 $m^2$.

The moisture permeability of the cellulose acylate film is preferably 500 $g/m^2 \cdot day$ to 2,000 $g/m^2 \cdot day$, and more preferably 900 $g/m^2 \cdot day$ to 1,300 $g/m^2 \cdot day$.

(Haze)

The haze of the cellulose acylate film is preferably equal to or less than 1%, more preferably equal to or less than 0.7%, and particularly preferably equal to or less than 0.5%. If the haze is kept to be equal to or less than the upper limit described above, the transparency of the cellulose acylate film is further improved, and this leads to an advantage that the cellulose acylate film can be more easily used as an optical film. Unless otherwise specified, the haze is measured and calculated by the following method. The lower limit of the haze is not particularly limited but is substantially equal to or greater than 0.001%.

By using a haze meter (trade name "HGM-2DP", manufactured by Suga Test Instruments Co., Ltd.), a 40 mm×80 mm cellulose acylate film is measured according to JIS K7136 in an environment with a temperature of 25° C. and a relative humidity of 60%.

(Film Thickness)

The average film thickness of the cellulose acylate film is preferably 10 μm to 100 μm, more preferably 15 μm to 80 μm, and even more preferably 15 μm to 70 μm. It is preferable that the film thickness is equal to or greater than 15 μm because then the handleability at the time of preparing a web-like film is improved. Furthermore, if the film thickness is equal to or less than 70 μm, the film can easily adapt to a change in humidity and maintain optical characteristics.

In a case where the cellulose acylate film has a laminated structure consisting of three or more layers, the film thickness of the core layer is preferably 3 μm to 70 μm and more preferably 5 μm to 60 μm, and the film thickness of each of the skin layer A and the skin layer B is more preferably 0.5 μm to 20 μm, particularly preferably 0.5 μm to 10 μm, and most preferably 0.5 μm to 3 μm.

(Width)

The width of the cellulose acylate film is preferably 700 mm to 3.000 mm, more preferably 1.000 mm to 2,800 mm, and particularly preferably 1,300 mm to 2,500 mm.

[Method for Manufacturing Polarizing Plate Protective Film]

The method for manufacturing the polarizing plate protective film, particularly, the method for manufacturing the cellulose acylate film is not particularly limited. The film is manufactured preferably by a melting film forming method or a solution film forming method and more preferably by a solution film forming method (solvent casting method). Regarding the examples of the manufacturing of a cellulose acylate film using the solvent casting method, it is possible to refer to publications such as U.S. Pat. Nos. 2,336,310A, 2,367,603A, 2,492,078A, 2,492,977A, 2,492,978A, 2,607, 704A, 2,739,069A, 2,739,070A, GB640731B, GB736892A, JP1970-4554B (JP-S45-4554B), JP1974-5614B (JP-S49-5614B), JP1985-176834A (JP-S60-176834A), JP1985-203430A (JP-S60-203430A), and JP1987-115035A (JP-S62-115035A). Furthermore, the cellulose acylate film may be subjected to a stretching treatment. Regarding the method and condition of the stretching treatment, for example, it is possible to refer to the publications such as JP1987-115035A (JP-S62-115035A), JP1992-152125A (JP-H04-152125A), JP1992-284211A (JP-H04-284211A), JP1992-298310A (JP-H04-298310A), and JP1999-48271A (JP-H11-48271A).

(Casting Method)

As the solution casting method, there is a method of uniformly extruding a prepared dope onto a metal support from a pressurized die, a doctor blade method of controlling the film thickness of a dope cast onto a metal support by using a blade, a reverse roll coater method of controlling the film thickness by using rolls performing reverse rotation, or the like. Among these, the method using a pressurized die is preferable. As the pressurized die, there is a coating hanger type, a T-die type, or the like, and any of these can be used. In addition to the method exemplified herein, various known methods for forming a film by casting a cellulose acylate solution can be performed. By setting the conditions in consideration of the difference in boiling point or the like between the used solvents, the same effect as described in each of the above publications can be obtained.

Co-Casting

For forming the polarizing plate protective film, particularly, for forming the cellulose acylate film, it is preferable to use a lamination casting method such as a co-casting method, a sequential casting method, or a coating method. From the viewpoint of stabilized manufacturing and reducing production costs, it is particularly preferable to use a simultaneous co-casting method.

In a case where the film is manufactured by a co-casting method and a sequential casting method, first, a solution (dope) as a composition containing the resin used in the polarizing plate protective film for each layer and the compound represented by Formula (I) of the present invention is prepared. The co-casting method (simultaneous multilayer casting) is a casting method in which a casting dope is extruded onto a casting support (a band or a drum) from a casting geeser that simultaneously extrudes casting dopes for the respective layers (which may be three or more layers) from different slits or the like such that the respective layers are simultaneously formed by casting, and the layers are peeled off from the support at an appropriate time and dried to form a film.

The sequential casting method is a casting method in which a casting dope for a first layer is extruded and casted onto a casting support from a casting geeser; a casting dope for a second layer is extruded onto the first layer, which has been dried or not been dried, from the casting geeser; a dope is then sequentially casted/laminated for forming a third layer or additional layers if necessary in the same manner as described above; and the layers are peeled off from the support at an appropriate time and dried to form a polarizing plate protective film. The coating method is generally a method in which a core layer having a film shape is formed by the solution film forming method; a coating solution with which the surface layer thereof will be coated is prepared; and either or both of the surfaces of the core layer are coated with the coating solution by using an appropriate coating machine and dried to form a polarizing plate protective film having a laminated structure.

As the metal support that is used for manufacturing the polarizing plate protective film and runs endlessly, a drum with surface mirror-finished through chromium plating or a stainless steel belt (which may be referred to as a band as well) mirror-finished through surface polishing is used. As the pressurized die used, a single die or two or more dies may be installed above the metal support. The number of the pressurized dies is preferably 1 or 2. In a case where two or more pressurized dies are installed, the amount of dope to be cast may be divided for the dies at various ratios, or the dope may be fed into the dies at each ratio from a plurality of micro metering gear pumps. The temperature of the dope (resin solution) used for casting is preferably −10° C. to 55° C., and more preferably 25° C. to 50° C. In this case, the solution temperature may be kept constant throughout the entire process or varied from step to step during the process. In a case where the temperature is varied, it should be set as desired immediately before casting.

The material of the metal support is not particularly limited, but the metal support is more preferably made of SUS (for example, SUS316).

(Peeling)

The method for manufacturing the polarizing plate protective film, particularly, the method for manufacturing the cellulose acylate film preferably includes a step of peeling off the aforementioned dope film from the metal support. The peeling method in the method for manufacturing the polarizing plate protective film is not particularly limited, and the peeling properties can be improved in a case where a certain method such as the addition of the peeling accelerator described above is used.

(Stretching Treatment)

The method for manufacturing the polarizing plate protective film, particularly, the method for manufacturing the cellulose acylate film can include a step of stretching the polarizing plate protective film formed to adjusting mechanical properties or imparting a phase difference. The polarizing plate protective film may is preferably stretched in either a transport direction (MD direction) of the polarizing plate protective film or a direction (TD direction) orthogonal to the transport direction. From the viewpoint of a polarizing plate processing process which follows the stretching treatment and uses the polarizing plate protective film, the direction (TD direction) orthogonal to the transport direction of the polarizing plate protective film is particularly preferable.

The method of stretching the film in the TD direction is described in, for example, JP1987-115035A (JP-S62-115035A), JP1992-152125A (JP-H04-152125A), JP1992-284211A (JP-H04-284211A), JP1992-298310A (JP-H04-298310A), and JP1999-48271A (JP-H11-48271A). In a case where the film is stretched in the MD direction, for example, if the speed of a transport roller of the polarizing plate protective film is adjusted such that the winding speed of the polarizing plate protective film becomes higher than the peeling speed of the polarizing plate protective film, the polarizing plate protective film is stretched. In a case where the film is stretched in the TD direction, by transporting the polarizing plate protective film that is being held by a tenter in a width direction and slowly widening the width of the tenter, the polarizing plate protective film can be stretched. The polarizing plate protective film can also be stretched using a stretching machine (preferably uniaxial stretching using a long stretching machine) after the film is dried.

In a case where the polarizing plate protective film is used as a protective film for a polarizer, in order to inhibit light leakage that occurs at the time when the polarizing plate is seen from an oblique viewpoint, the transmission axis of the polarizer and the in-plane slow axis of the polarizing plate protective film need to be arranged such that they are parallel to each other. Generally, the transmission axis of a continuously manufactured roll film-like polarizer is parallel to the width direction of the roll film. Therefore, in order to bond the roll film-like polarizer and the protective film composed of the roll film-like polarizing plate protective film together, the in-plane slow axis of the roll film-like protective film needs to be parallel to the width direction of the polarizing plate protective film. Accordingly, the polarizing plate protective film is preferably stretched further in the TD direction. The stretching treatment may be performed in the middle of the film forming step or performed on the original film wound up after being formed.

The stretching ratio at which the film is stretched in the TD direction is preferably 5% to 100%, more preferably 5% to 80%, and particularly preferably 5% to 40%. Herein, "unstretched" means that the stretching ratio is 0%. The stretching treatment may be performed in the middle of the film forming step or performed on the original film wound up after being formed. If the former is the case, the film may be stretched in a state of containing residual solvent. In a case where the amount of residual solvent=(mass of residual volatile components/mass of film having undergone heating treatment)×100% is 0.05% to 50%, the film can be preferably stretched. It is particularly preferable to stretch the film 5% to 80% in a state where the amount of residual solvent is 0.05% to 5%.

(Drying)

From the viewpoint of inducing retardation, it is preferable that the method for manufacturing the polarizing plate protective film, particularly, the method for manufacturing the cellulose acylate film includes a step of drying the polarizing plate protective film and a step of stretching the dried polarizing plate protective film at a temperature of equal to or higher than a glass transition temperature (Tg)–10° C.

As the method for drying the dope on the metal support, generally, there is a method in which the front surface side of the metal support (a drum or a belt), that is, the front surface of the web on the metal support is exposed to hot air, a method in which the rear surface of the drum or belt is exposed to hot air, a rear surface liquid heat transmission method in which a temperature-controlled liquid is brought into contact with the rear surface of the belt or drum that is on the opposite side of the dope casting surface and the drum or belt is heated by heat transmission so as to control the surface temperature, or the like. Among these, the rear surface liquid heat transmission method is preferable. The surface temperature of the metal support having not yet been subjected to casting is not limited as long as it is equal to or lower than the boiling point of a solvent used in the dope. However, in order to accelerate drying or to eliminate fluidity on the metal support, the surface temperature is more preferably set to be a temperature 1° C. to 10° C. lower than the boiling point of a solvent having the lowest boiling point among the used solvents. In a case where the film is peeled off without the step of cooling and drying the cast dope, the above limitation is not imposed.

The thickness of the polarizing plate protective film should be adjusted by controlling the concentration of solid content contained in the dope, the gap between slits of mouthpieces of the die, the pressure at which the dope is extruded from the die, the speed of the metal support, and the like such that a desired thickness is obtained.

The polarizing plate protective film obtained as above is wound up such that the length thereof becomes preferably 100 m to 10,000 m, more preferably 500 m to 7,000 m, and even more preferably 1,000 m to 6,000 m per single roll. At the time of winding, it is preferable to form knurls on at least one end of the film. The width of knurls is preferably 3 mm to 50 mm and more preferably 5 mm to 30 mm, and the height thereof is preferably 0.5 μm to 500 μm and more preferably 1 μm to 200 μm. The knurls may be formed by single-action pressing or double-action pressing.

In a case where the polarizing plate protective film is used as an optical compensation film for a large-screen liquid crystal display device, for example, the film is preferably molded such that it has a film width of equal to or greater than 1,470 mm. The polarizing plate protective film of the present invention includes not only a film taking an aspect in which it is a film piece cut in a size that enables the film to be incorporated as it is into a liquid crystal display device but also a film taking an aspect in which it is prepared as a long film through continuous production and wound up in the form of a roll. The polarizing plate protective film taking the later aspect is stored and transported as it is and then used by being cut in a desired size at the time of being actually incorporated into a liquid crystal display device or being bonded to a polarizer or the like. Furthermore, when the polarizing plate protective film is actually incorporated into a liquid crystal display device after being directly bonded as a long film to a polarizer or the like composed of a polyvinyl alcohol film prepared as a long film just like the polarizing plate protective film, the polarizing plate protective film is used by being cut in a desired size. As one of the aspects of the optical compensation film wound up in the form of a roll, an aspect is exemplified in which the film is wound up in the form of a roll having a length of equal to or greater than 2,500 m.

<<Functional Layer>>

On the polarizing plate protective film of the present invention, a functional layer can be disposed as desired according to the purpose.

Examples of the functional layer include a hardcoat layer, an antireflection layer, a light scattering layer, an antifouling layer, an antistatic layer, and the like, and a single functional layer may perform a plurality of functions.

For example, the hard coat layer is a layer for imparting hardness or scratch resistance to the polarizing plate protective film. For instance, by coating the polarizing plate protective film with a coating composition and curing the composition, it is possible to form a hardcoat layer which is compatible with the compound represented by Formula (I) and exhibits high adhesiveness with respect to the polarizing plate protective film, particularly, to the cellulose acylate film. By adding a filler or an additive to the hardcoat layer, it is possible to impart physical performance such as mechanical, electrical, and optical performances or chemical performances such as water/oil repellency to the hardcoat layer. The thickness of the hardcoat layer is preferably 0.1 μm to 6 μm, and more preferably 3 μm to 6 μm. If a thin hardcoat layer having a thickness within the above range is used, it is possible to obtain a hardcoat layer-containing polarizing plate protective film in which physical properties such as brittleness or curling is improved or suppressed, weight lightening is achieved, and manufacturing costs are reduced.

The hardcoat layer is preferably formed by curing a curable composition, and the curable composition is preferably prepared as a liquid coating composition. For example, the coating composition contains a binder monomer or oligomer forming matrix, polymers, and an organic solvent. By curing the coating composition after coating, the hardcoat layer can be formed. For curing, a cross-linking reaction or a polymerization reaction can be used.

[[Polarizer]]

[Resin]

For the polarizer of the present invention, a polyvinyl alcohol-based resin is preferably used. In the polarizer of the present invention, the polyvinyl alcohol resin becomes a main component and generally accounts for 80% by mass or more of the polarizer. Usually, polyvinyl alcohol is obtained by the saponification of polyvinyl acetate, and may contain components that can be copolymerized with vinyl acetate, such as unsaturated carboxylic acid, unsaturated sulfonic acid, olefins, and vinyl ethers. Furthermore, it is also possible to use a modified polyvinyl alcohol-based resin containing an acetoacetyl group, a sulfonic acid group, a carboxy group, an oxyalkylene group, or the like.

The degree of saponification of the polyvinyl alcohol-based resin is not particularly limited, but is preferably 80 mol % to 100 mol % and particularly preferably 90 mol % to 100 mol % from the viewpoint of solubility and the like. In addition, the degree of polymerization of the polyvinyl alcohol-based resin is not particularly limited, but is preferably 1,000 to 10,000 and particularly preferably 1,500 to 5,000.

The modulus of elasticity of the unstretched polyvinyl alcohol-based resin that is represented by a Young's modulus is preferably equal to or greater than 0.1 MPa and equal to or less than 500 MPa, and even more preferably equal to or greater than 1 MPa and equal to or less than 100 MPa.

If the modulus of elasticity is within the above range, it is possible to manufacture a polyvinyl alcohol-based resin film which exhibits an excellent wrinkling inhibition effect after stretching and has sufficient strength.

The thickness of the unstretched polyvinyl alcohol-based resin film is not particularly limited. However, from the viewpoint of stably retaining and uniformly stretching the film, the thickness of the film is preferably 1 μm to 1 mm, and particularly preferably 20 μm to 200 μm. Furthermore, the film thickness of the stretched polyvinyl alcohol-based resin film is preferably 2 μm to 100 μm. From the viewpoint of improving light leakage, the film thickness is preferably 7 μm to 25 μm. The film thickness of the polarizer is determined by the thickness of the polarizing plate protective film described above.

The content of the compound represented by Formula (I) of the present invention in the polarizer or the amount of the compound added to the composition is not particularly limited, but is preferably 0.01 parts by mass to 30 parts by mass, more preferably 0.01 parts by mass to 10 parts by mass, and particularly preferably 1.0 part by mass to 10 parts by mass, with respect to 100 parts by mass of the resin constituting the polarizer.

In a case where the polarizer contains two or more kinds of compound represented by Formula (I), the total amount thereof is preferably within the above range.

<<Dichroic Colorant>>

The polarizer of the present invention preferably contains a dichroic colorant. In the present specification, the dichroic colorant refers to a colorant whose absorbance varies with direction and includes iodine ions, a diazo-based colorant, a quinone-based colorant, any of other dichroic dyes, and the like. As the dichroic colorant, it is possible to use higher iodine ions such as $I_3^-$ or $I_5^-$ or a dichroic dye.

In the present invention, the higher iodine ions are particularly preferably used. As described in Ryo Nagata, "Application of Polarizing Plate", CMC Publishing CO., LTD. and "Industrial Material", Vol. 28, No. 7, pp 39-45, by dipping polyvinyl alcohol in an aqueous boric acid solution and/or a liquid obtained by dissolving iodine in an aqueous potassium iodide solution, the higher iodine ions can be generated in a state of being adsorbed/aligned onto polyvinyl alcohol.

The content of the dichroic colorant is preferably 0.1 parts by mass to 50 parts by mass, more preferably 0.5 parts by mass to 20 parts by mass, and even more preferably 1.0 part by mass to 5.0 parts by mass, with respect to 100 parts by mass of the polyvinyl alcohol-based resin.

If necessary, in addition to the polyvinyl alcohol-based resin, the dichroic colorant, and the compound represented by Formula (I) of the present invention, a plasticizer and a surfactant may be added to the polarizer of the present invention.

<Method for Manufacturing Polarizer>

The method for manufacturing the polarizer of the present invention includes a step of forming a polyvinyl alcohol-based resin solution, which contains a polyvinyl alcohol-based resin and the compound represented by Formula (I) of the present invention in an amount of 1.0 part by mass to 10 parts by mass with respect to 100 parts by mass of the polyvinyl alcohol-based resin, into a film, a step of stretching the polyvinyl alcohol-based resin film, and a step of dying the stretched polyvinyl alcohol-based resin film with a dichroic colorant.

In the method for manufacturing the polarizer of the present invention, for example, it is preferable that the polyvinyl alcohol-based resin is formed into a film and then iodine is introduced into the film so as to constitute the polarizer. The polyvinyl alcohol-based resin film can be manufactured with reference to the method described in paragraphs "0213" to "0237" of JP2007-86748A, JP3342516B, JP1997-328593A (JP-H09-328593A), JP2001-302817A, JP2002-144401A, and the like. Furthermore, the timing the compound represented by Formula (I) is added to the polyvinyl alcohol-based resin is not particularly limited.

In the step of forming the polyvinyl alcohol-based resin solution into a film, it is preferable that the polyvinyl alcohol-based resin solution is added to water with stirring so as to prepare a stock solution in which the polyvinyl alcohol-based resin is dissolved in water or an organic solvent. The concentration of the polyvinyl alcohol-based resin in the stock solution is preferably 5% by mass to 20% by mass. Furthermore, by dehydrating the obtained slurry, a polyvinyl alcohol-based resin wet cake having a moisture content of about 40% may be prepared once. In a case where an additive is then added thereto, for example, it is preferable to use a method in which the wet cake of polyvinyl alcohol is put into a dissolution tank, a plasticizer and water are added thereto, and the resultant is stirred in a state where water vapor is being injected from the bottom of the tank. It is preferable to heat the resultant such that the temperature of the resin in the tank becomes 50° C. to 150° C., or the internal pressure of the system may be increased.

From the viewpoint of uniformly dispersing the compound represented by Formula (I) in the polarizer, it is preferable to add the compound represented by Formula (I) of the present invention to the polarizer in this step. In addition, in a case where the compound represented by Formula (I) of the present invention is added, it is preferable to use a method in which the wet cake of polyvinyl alcohol is put into a dissolution tank and then stirred in a state where water vapor is being injected from the bottom of the tank.

Furthermore, in the present invention, it is preferable to manufacture the polarizer by bonding the polarizer and the polarizing plate protective film together by using an adhesive containing the compound represented by Formula (I) of the present invention or by bonding the polarizer and a substrate (liquid crystal cell) together by using an adhesive containing the compound represented by Formula (I) of the present invention. It is preferable that the polarizer is prepared by the aforementioned method because then the compound represented by Formula (I) of the present invention can be contained in the layer obtained by bonding, and the compound of the present invention can be brought into contact with the polarizer (layer).

In the present invention, it is preferable that the polarizer containing the compound represented by Formula (I) of the present invention is manufactured through following steps.

The steps include a step of forming a polyvinyl alcohol-based resin solution containing the polyvinyl alcohol-based resin and the compound represented by Formula (I) into a film, a step of stretching the polyvinyl alcohol-based resin film, a step of dying the stretched polyvinyl alcohol-based resin film with a dichroic colorant, and a step of crosslinking the dyed polyvinyl alcohol-based resin film by using boric acid.

In the present invention, generally, a method of forming a film by casting the polyvinyl alcohol-based resin stock solution prepared as above is preferably used. The casting method is not particularly limited. However, it is preferable to use a method in which the heated polyvinyl alcohol-based resin stock solution is supplied into a double-screw extruder and formed into a film by being cast onto a support from discharge means (preferably a die and more preferably a T-shaped slit die) by a gear pump. The temperature of the resin solution discharged from the die is not particularly limited.

As the support, a casting drum is preferable, and the diameter, width, rotation speed, and surface temperature of the drum are not particularly limited. The diameter of the casting drum is preferably 2,000 mm to 5,000 mm, more preferably 2,500 mm to 4,500 mm, and particularly preferably 3,000 mm to 3,500 mm.

The width of the casting drum is preferably 2 m to 6 m, more preferably 3 m to 5 m, and particularly preferably 4 m to 5 m.

The rotation speed of the casting drum is preferably 2 m/min to 20 m/min, more preferably 4 m/min to 12 m/min, and particularly preferably 5 m/min to 10 m/min.

The surface temperature of the casting drum is preferably 40° C. to 140° C., more preferably 60° C. to 120° C., and particularly preferably 80° C. to 100° C.

The resin temperature at the outlet of the T-shaped slit die is preferably 40° C. to 140° C., more preferably 60° C. to 120° C., and particularly preferably 80° C. to 100° C.

Then, it is preferable to dry the obtained roll by causing the rear surface and front surface thereof to alternately pass through a drying roll. The diameter, width, rotation speed, and surface temperature of the drying roll are not particularly limited. The diameter of the drying drum is preferably 200 mm to 450 mm, more preferably 250 mm to 400 mm, and particularly preferably 300 mm to 350 mm.

The length of the obtained film is not particularly limited, and the film can be a long film having a length of equal to or greater than 2,000 m and preferably equal to or greater than 4,000 m. The width of the film is not particularly limited but is preferably 2 m to 6 m and more preferably 3 m to 5 m.

After the polyvinyl alcohol-based resin solution is formed into a film, the film is stretched. For stretching, it is possible to use the vertical uniaxial stretching method described in U.S. Pat. No. 2,454,515A or the like or the tenter method described in JP2002-86554A. The stretching ratio is preferably 2-fold to 12-fold, and more preferably 3-fold to 10-fold. Furthermore, the stretching ratio, the thickness of the original film, and the thickness of the polarizer can preferably have a relationship of (film thickness of polarizer bonded to polarizing plate protective film/thickness of original film)× (total stretching ratio)>0.17 as described in JP2002-

040256A, or the width of the polarizer at the time of being taken out of the final bath and the width of the polarizer at the time of bonding to the polarizing plate protective film can preferably have a relationship of 0.80≤(width of polarizer at the time of bonding to polarizing plate protective film/width of polarizer at the time of being taken out of the final bath)≤0.95 as described in JP2002-040247A.

After being stretched, the polyvinyl alcohol-based resin film is dyed with a dichroic colorant through gas phase adsorption or liquid phase adsorption. For example, in a case where dying is performed in a liquid phase by using iodine as a dichroic colorant, a polymer film for a polarizer (for example, the polyvinyl alcohol-based resin film) is dyed by being dipped into an aqueous solution of iodine/potassium iodide. The amount of iodine is preferably 0.1 g/l to 20 g/l, the amount of potassium iodide is preferably 1 g to 200 g, and a mass ratio of potassium iodide to iodine is preferably 1 to 200. The dying time is preferably 10 seconds to 5,000 seconds, and the solution temperature is preferably 5° C. to 60° C. As the dying method, in addition to dipping, any means such as coating or spraying of iodine or a dye solution can be used. The dying step may be performed before or after the stretching step of the present invention. However, it is particularly preferable to dye the film in a liquid phase before the stretching step because then the film swells to an appropriate degree and is easily stretched.

For dying, the method described in JP2002-86554A can be used. Furthermore, as the dying method, in addition to dipping, any means such as coating or spraying of iodine or a dye solution can be used. In addition, the concentration of iodine, the temperature of a dying bath, the stretching ratio in the bath, and the method of dying the film while stirring the bathing solution in the bath that are described in JP2002-290025A may also be used.

Herein, as described in JP3145747B, a boron-based compound such as boric acid or borax may be added to the dying solution.

As other steps, a swelling step, a curing step, and a drying step may be performed. These steps are described in paragraphs "0039" to "0050" of JP2011-237580A, and the content of which is incorporated into the present specification.

[[Adhesive Layer]]

As the method for laminating the constituents such as the polarizing plate, the polarizing plate protective film, and the polarizer of the present invention, it is preferable to use an adhesive layer. In a case where the adhesive layer has pressure sensitiveness, the adhesive layer can be used by being bonded as it is, although the way the adhesive layer is used varies with the characteristics thereof. At this time, a step of improving adhesiveness such as a saponification treatment may also be performed.

[Resin Used in Adhesive Layer]

The resin used in the adhesive layer is not particularly limited as long as it is a resin which is compatible with the compound represented by Formula (I) of the present invention and has a function of bonding layers together. The way the adhesive enables adhesion is not particularly limited. The adhesive used may be a pressure sensitive adhesive having viscosity or an adhesive expressing adhesiveness through drying or a reaction. In the present invention, the adhesive layer means both of the adhesive layer and the pressure sensitive adhesive layer.

In the present invention, the adhesive layer contains a resin as a main component. Generally, the proportion of the resin in the adhesive layer is preferably equal to or greater than 60% by mass and more preferably equal to or greater than 70% by mass.

The amount of the compound represented by Formula (I) of the present invention that is contained in the adhesive layer or added to the composition is not particularly limited. However, the amount of the compound is preferably 0.01 parts by mass to 30 parts by mass, more preferably 0.01 parts by mass to 10 parts by mass, and particularly preferably 1 part by mass to 10 parts by mass, with respect to 100 parts by mass of the resin constituting the adhesive layer.

In a case where the adhesive layer contains two or more kinds of compound represented by Formula (I), the total amount there is preferably within the range described above.

The adhesive layer is formed by, for example, coating the surface of at least either the polarizing plate protective film or the polarizer with a coating solution containing an adhesive at a predetermined ratio and drying the coating solution. As the method for preparing the coating solution, any of appropriate methods can be adopted. As the coating solution, for example, a commercially available solution or dispersion, a solution obtained by adding a solvent to a commercially available solution or dispersion, or a solution obtained by dissolving or dispersing solid contents in various solvents may be used.

As the adhesive, any of adhesives having appropriate properties, forms, and adhesion mechanism can be used according to the purpose. Specific examples of the adhesive include a water-soluble adhesive, an ultraviolet curable type adhesive, an emulsion-type adhesive, a latex-type adhesive, a mastic adhesive, a multilayered adhesive, a paste-like adhesive, a foaming-type adhesive, a supported film adhesive, a thermoplastic adhesive, a thermofusion-type adhesive, a heat solidification adhesive, a hot melt adhesive, a heat activated adhesive, a heat seal adhesive, a thermosetting adhesive, a contact-type adhesive, a pressure sensitive adhesive, a polymerization-type adhesive, a solvent-type adhesive, and a solvent-activated adhesive. Among these, a water-soluble adhesive and an ultraviolet curable type adhesive are preferable. Particularly, in a case where the layer neighboring the polarizer in the polarizing plate of the present invention is an adhesive layer formed of an adhesive, among the aforementioned adhesives, a water-soluble adhesive having excellent transparency, adhesiveness, workability, and economic efficiency and resulting in good product quality is preferably used.

(A) Water-Soluble Adhesive

The water-soluble adhesive may contain, for example, at least either a natural polymer or a synthetic polymer soluble in water. Examples of the natural polymer include proteins, starch, and the like. Examples of the synthetic polymer include resol resin, a urea resin, a melamine resin, polyethylene oxide, polyacrylamide, polyvinyl pyrrolidone, a polyacrylic acid ester, a polymethacrylic acid ester, a polyvinyl alcohol-based resin, and the like. Among these, a water-soluble adhesive containing a polyvinyl alcohol-based resin is preferably used. Particularly, in the polarizing plate of the present invention, it is preferable that a layer neighboring the polarizer contains the water-soluble adhesive containing a polyvinyl alcohol-based resin, because then the layer exhibits extremely excellent adhesiveness with respect to the polarizer and the polarizing plate protective film.

The adhesive is not limited in terms of the way it enables adhesion. The adhesive used may be a pressure sensitive adhesive having viscosity, or an adhesive expressing adhesiveness through drying or a reaction.

As the pressure sensitive adhesive, any of appropriate pressure sensitive adhesives can be adopted. Specific examples of the pressure sensitive adhesive include a solvent-type pressure sensitive adhesive, a non-aqueous emulsion-type pressure sensitive adhesive, an aqueous pressure sensitive adhesive, and a hot melt pressure sensitive adhesive. Particularly, in a case where the adhesive layer is formed of a pressure sensitive adhesive, among the above adhesives, a solvent-type pressure sensitive adhesive containing an acrylic polymer as a base polymer is preferably used. This is because such a pressure sensitive adhesive exhibits appropriate pressure sensitive characteristics (for example, wettability, aggregating properties, and adhesiveness) with respect to the polarizer and the polarizing plate protective film and has excellent optical transparency, weather fastness, and heat resistance.

(Metal Compound Colloid)

The water-soluble adhesive may contain a metal compound. Particularly, from the viewpoint of improving the durability of the polarizer at a high humidity, it is preferable that the water-soluble adhesive containing a polyvinyl alcohol-based resin or the like contains a metal compound colloid. This is because the occurrence of "knicks", which are localized irregularity defects caused in the interface between the polarizer and the polarizing plate protective film, can be prevented, and water resulting from environmental humidity can be prevented from flowing into the polarizer when the polarizing plate is tested regarding durability in a highly humid environment.

For example, the metal compound colloid may be a substance in which fine metal compound particles are dispersed in a dispersion medium, or a substance which is electrostatically stabilized due to the mutual repulsion between same charges of fine particles and exhibits lasting stability. The average particle size of the fine particles forming the metal compound is not particularly limited, but is preferably within a range of 1 nm to 100 nm, more preferably within a range of 1 nm to 50 nm, and particularly preferably within a range of 2 nm to 40 nm. This is because the fine particles are uniformly dispersed in the adhesive layer, the occurrence of knicks can be more suitably prevented with securing adhesiveness, and the durability of the polarizer can be improved.

As the metal compound, any of appropriate compounds can be adopted. Specific examples of the metal compound include metal oxide such as alumina, silica, zirconia, or titania, a metal salt such as aluminum silicate, calcium carbonate, magnesium silicate, zinc carbonate, barium carbonate, or calcium phosphate, and mineral such as celite, talc, clay, or kaolin. Among these, alumina is preferable.

In a case where the metal compound (preferably the metal compound colloid) is formulated, the amount thereof formulated is preferably equal to or less than 40% by mass and more preferably 1% by mass to 30% by mass, with respect to the resin (adhesive) constituting the adhesive layer.

(Other Additives)

In the present invention, in addition to the above components, other compounds may be formulated with the adhesive layer, within a scope that does not depart from the gist of the present invention.

For example, in order to improve the adhesiveness between the adhesive layer and the film layer or the polarizer layer, a cross-linking agent such as boric acid can be formulated. It is known that, if contained in the adhesive layer, the boric acid forms a cross-linked structure with the bond of a hydroxy group in the polymer and thus improves the adhesiveness.

The compound represented by Formula (I) of the present invention also exerts an effect of accelerating bonding between the boric acid and the hydroxy group in the polymer. In a case of polarizing plate protective film whose surface has a large number of hydroxy groups due to a saponification treatment just like the cellulose acylate-based polarizing plate protective film, by the addition of the compound represented by Formula (I) of the present invention to the adhesive layer, boric acid cross-linking between the adhesive layer and the polarizer layer and between the adhesive layer and the polarizing plate protective film can be accelerated, and thus the adhesiveness can be further improved.

Even in an aspect in which the film does not contains a hydroxy group within the surface thereof just like a polyester-based resin such as polyethylene terephthalate or a cycloolefin-based resin, the film can be changed to a film having hydroxy groups through a saponification treatment as above, and hence the same effect can be obtained.

It is particularly preferable that the cross-linking agent described above and the compound represented by Formula (I) of the present invention are combined with polyvinyl alcohol or a cellulose acylate resin which are polymers having a large number of hydroxy groups.

In a case where boric acid is formulated, the amount thereof formulated is preferably 1% by mass to 1,000% by mass, and more preferably 10% by mass to 100% by mass, with respect to the compound represented by Formula (I) of the present invention.

Examples of other additives include a chain transfer agent, a sensitizer, a viscosity imparting agent, a thermoplastic resin, a filler, a fluidity adjuster, a plasticizer, an anti-foaming agent, and the like. In a case where these additives are formulated, the amount thereof formulated is preferably equal to or less than 40% by mass, and more preferably 0.1% by mass to 30% by mass, with respect to the resin (adhesive) constituting the adhesive layer.

Regarding the materials of the resin used in the adhesive layer or the matters relating to handling of the materials, it is possible to refer to paragraphs "0069" to "0138" of JP2012-014148A, paragraphs "0013" to "0020" of JP2009-244800A, paragraphs "0039" to "0086" of JP2010-230806A, paragraphs "0114" to "0119" of JP2009-139658A, and the like.

The thickness of the adhesive layer can be appropriately set according to the purpose of use, the adhesion force, or the like. Specifically, in a case where a pressure sensitive adhesive is used in the adhesive layer, the thickness of the adhesive layer is preferably within a range of 0.1 µm to 50 µm, more preferably within a range of 0.5 µm to 20 µm, even more preferably within a range of 1 µm to 15 µm, and particularly preferably within a range of 5 µm to 10 µm.

In a case where an adhesive is used in the adhesive layer, the thickness of the adhesive layer is preferably within a range of 10 nm to 500 nm, more preferably within a range of 10 nm to 400 nm, and even more preferably within a range of 20 nm to 350 nm.

(B) Ultraviolet Curable Type Adhesive

As the adhesive layer in the polarizing plate of the present invention, an ultraviolet curable type adhesive layer can also be preferably used. The use of the ultraviolet curable type adhesive enables the polarizing plate protective film and the polarizer to adhere to each other with high adhesion strength. In the present specification, the ultraviolet curable type adhesive layer refers to a layer formed by curing the ultraviolet curable type adhesive by using ultraviolet rays.

(Composition of Ultraviolet Curable Type Adhesive)

According to the curing method, the ultraviolet curable type adhesive can be classified into, for example, a radical polymerization-type adhesive and a cationic polymerization-type adhesive. Furthermore, according to the chemical species of the components of the adhesive, the ultraviolet curable type adhesive can be classified into, for example, an acrylic resin-based adhesive and an epoxy resin-based adhesive. In the present invention, any of these may be used, or a mixture of two or more kinds thereof may be used. From the viewpoint of ease of handling, the adhesion strength obtained, and the like, a cationic polymerization-type epoxy resin-based adhesive is suitably used. The epoxy resin refers to a compound or a polymer which has two or more epoxy groups on average in a molecule and is cured through a polymerization reaction using epoxy groups. In the related field, conventionally, even an epoxy monomer is also referred to as an epoxy resin.

As the epoxy resin contained in the ultraviolet curable type adhesive, from the viewpoint of weather fastness, refractive index, cationic polymerization properties, and the like, an epoxy resin not containing an aromatic ring in a molecule is suitably used. Examples of the epoxy resin not containing an aromatic ring in a molecule include a hydrogenated epoxy resin, an alicyclic epoxy resin, an aliphatic epoxy resin, and the like.

The hydrogenated epoxy resin can be obtained by causing an aromatic epoxy resin to selectively undergo a nucleus hydrogenation reaction under pressure in the presence of a catalyst. Examples of the aromatic epoxy resin include a bisphenol-type epoxy resin such as diglycidyl ether of bisphenol A, diglycidyl ether of bisphenol F, and diglycidyl ether of bisphenol S; a novolac-type epoxy resin such as a phenol novolac epoxy resin, a cresol novolac epoxy resin, and hydroxybenzaldehyde phenol novolac epoxy resin; a polyfunctional epoxy resin such as glycidyl ether of tetrahydroxyphenylmethane, glycidyl ether of tetrahydroxybenzophenone, and epoxylated polyvinyl phenol; and the like. Among these, glycidyl ether of hydrogenated bisphenol A is preferably used as the hydrogenated epoxy resin.

Examples of the aliphatic epoxy resin include polyglycidyl ether of aliphatic polyol or an alkylene oxide adduct thereof. More specifically, examples thereof include diglycidyl ether of 1,4-butanediol; diglycidyl ether of 1,6-hexanediol; triglycidyl ether of glycerin; triglycidyl ether of trimethylolpropane; diglycidyl ether of polyethylene glycol; diglycidyl ether of propylene glycol; polyglycidyl ether of polyether polyol obtained by adding one kind or two or more kinds of alkylene oxide (ethylene oxide, propylene oxide, or the like) to aliphatic polyol such as ethylene glycol, propylene glycol, or glycerin; and the like.

As the epoxy resin, the hydrogenated epoxy resin is more preferable.

In the present invention, one kind of epoxy resin may be used singly, or two or more kinds thereof may be used concurrently.

The epoxy equivalent of the epoxy resin used in the present invention is generally within a range of 30 g/equivalent to 3,000 g/equivalent, and preferably within a range of 50 g/equivalent to 1,500 g/equivalent. If the epoxy equivalent is greater than 30 g/equivalent, the cured adhesive layer becomes excellently flexible, and the adhesion strength becomes excellent. In contrast, if the epoxy equivalent is equal to or less than 3,000 g/equivalent, the epoxy resin becomes excellently compatible with other components contained in the adhesive.

In the present invention, as described above, cationic polymerization is preferably used as the curing reaction of the epoxy resin. Therefore, the ultraviolet curable type adhesive preferably contains a cationic photopolymerization initiator. The cationic photopolymerization initiator generates a cation species or Lewis acid by being irradiated with ultraviolet rays and initiates a polymerization reaction of an epoxy group. Any type of cationic polymerization initiator may be used, but from the viewpoint of workability, it is preferable to use those having latency.

The method of curing the adhesive through the irradiation of ultraviolet rays by using the cationic photopolymerization initiator is advantageous because it enables curing at normal temperature, reduces the necessity of considering the heat resistance or expansion-induced distortion of the polarizer, and enables the polarizing plate protective film and the polarizer to excellently adhere to each other. Furthermore, because the cationic photopolymerization initiator shows catalytic action due to light, even if it is mixed with the epoxy resin, the adhesive exhibits excellent storage stability and workability.

The cationic photopolymerization initiator is not particularly limited, and examples thereof include an onium salt such as an aromatic diazonium salt, an aromatic iodonium salt, or an aromatic sulfonium salt and a iron-allene complex.

One kind of cationic polymerization initiator may be used singly, or two or more kinds thereof may be used by being mixed together. Particularly, an aromatic sulfonium salt exhibits ultraviolet absorption characteristics even in a wavelength range of equal to or greater than 300 nm. Therefore, the aromatic sulfonium salt is preferably used because it has excellent curing properties and can produce a cured material having excellent mechanical strength and adhesion strength.

The amount of the cationic photopolymerization initiator formulated is generally 0.5 parts by mass to 100 parts by mass, and preferably equal to or greater than 1 part by mass, with respect to 100 parts by mass of the epoxy resin. Furthermore, the amount is preferably equal to or less than 50 parts by mass. If the amount of the cationic photopolymerization initiator is within the above range, the adhesive can be sufficiently cured, and the mechanical strength or adhesion strength is secured. In addition, it is preferable that the amount of the cationic photopolymerization initiator formulated is equal to or less than 100 parts by mass with respect to 100 parts by mass of the epoxy resin, because then the amount of ionic substances in the cured material does not easily increase, thus the hygroscopicity of the cured material does not increase too much, and the durability of the polarizing plate does not easily decrease.

In a case where the cationic photopolymerization initiator is used, if necessary, the ultraviolet curable type adhesive can further contain a photosensitizer. The use of the photosensitizer makes it possible to improve the reactivity of the cationic polymerization and improve the mechanical strength and adhesion strength of the cured material. Examples of the photosensitizer include a carbonyl compound, an organic sulfur compound, persulfide, a redox-based compound, an azo and diazo compound, a halogen compound, a photoreducing colorant, and the like. One kind of photosensitizer may be used singly, or two or more kinds thereof may be used by being mixed together. The amount of the photosensitizer contained in the ultraviolet curable type adhesive is preferably within a range of 0.1 parts by mass to 20 parts by mass with respect to 100 parts by mass of the ultraviolet curable type adhesive.

The ultraviolet curable type adhesive may further contain a compound accelerating cationic polymerization, such as oxetanes or polyols.

As long as the effects of the present invention are not impaired, the ultraviolet curable type adhesive can further contain other additives such as an ion trapping agent, an antioxidant, a chain transfer agent, a sensitizer, a viscosity imparting agent, a thermoplastic resin, a filler, a fluidity adjuster, a plasticizer, an anti-foaming agent, and the like. Examples of the ion trapping agent include a powdery inorganic compound based on bismuth, antimony, magnesium, aluminum, calcium, or titanium and a mixture of these. Examples of the antioxidant include a hindered phenol-based antioxidant.

In a case where the compound represented by Formula (I) of the present invention is used in the adhesive layer, the resin of the polarizing plate protective film is cellulose acylate, and a water-soluble adhesive (particularly a polyvinyl alcohol-based resin) is used, a water-soluble compound is preferred as the compound represented by Formula (I) of the present invention.

This is because the compound represented by Formula (I) of the present invention is easily diffused in the polarizer (layer), and the best effect is obtained in the present invention.

In contrast, in a case where the resin of the polarizing plate protective film is a synthetic resin such as an acrylic resin or a cycloolefin-based resin that does not use a natural substance as a material, and the ultraviolet curable type adhesive is used, a semi-water-soluble compound is preferred as the compound represented by Formula (I) of the present invention.

The solubility of the water-soluble compound water at 25° C. is preferably equal to or greater than 0.1 g/100 ml, more preferably equal to or greater than 1.0 g/100 ml, and even more preferably 1.0 g/100 ml to 30.0 g/100 ml. The solubility of the semi-water-soluble compound in water at 25° C. is preferably 0.01 g/100 ml to 5.0 g/100 ml, more preferably 0.05 g/100 ml to 5.0 g/100 ml, and even more preferably 0.1 g/100 ml to 5.0 g/100 ml.

(Method for Laminating Polarizer and Adhesive Layer)

The method for laminating the polarizer and the adhesive layer includes a step of laminating the polarizer and the adhesive layer, that is, the method for manufacturing a laminate of the present invention.

The compound represented by Formula (I) of the present invention may be added at any time without particular limitation as long as the compound remains contained in the final product.

The method for laminating the adhesive layer on the polarizer is not particularly limited. From the viewpoint of controlling manufacturing or efficiency, lamination performed by coating can be preferably used.

As the coating method, any of appropriate methods can be adopted. Examples of the coating method include a spin coating method, a roll coating method, a flow coating method, a dip coating method, a bar coating method, and the like.

<<Polarizing Plate>>

The polarizing plate of the present invention has at least the polarizer and the polarizing plate protective film. It is preferable that the polarizing plate of the present invention has the polarizer and the polarizing plate protective film on one surface or both surfaces of the polarizer. In the present invention, the polarizing plate is formed of the polarizing plate composition of the present invention. Therefore, the compound represented by Formula (I) of the present invention is contained in or added to at least any one of the polarizing plate protective film, the polarizer, and the adhesive layer.

The compound represented by Formula (I) of the present invention may be contained in or added to a plurality of different layers. In a case where the compound is contained in a plurality of different layers, different kinds of compound represented by Formula (I) may be used in each of the layers.

It is preferable that the polarizing plate protective film of the present invention is bonded to the polarizer such that the transmission axis of the polarizer and the slow axis of the polarizing plate protective film of the present invention are substantially orthogonal or parallel to each other or meet at an angle of 45°. In the liquid crystal display device of the present invention, it is preferable that the transmission axis of the polarizer and the slow axis of the polarizing plate protective film of the present invention are substantially orthogonal to each other. Herein, "substantially orthogonal" means that the direction of a principal refractive index nx of the polarizing plate protective film of the present invention and the direction of the transmission axis of the polarizer cross each other at an angle of 90°±10°. The angle at which they cross each other is preferably 90°±5°, and more preferably 90°±1°. If the angle is within the above range, the light leakage occurring under a polarizing plate cross nicol can be further reduced. The slow axis can be measured by any of various methods, and for example, a birefringence analyzer (trade name "KOBRA DH", manufactured by Oji Scientific Instruments Co., Ltd.) can be used.

The polarizing plate of the present invention includes not only a polarizing plate in the form of a film piece which is cut in a size enabling the film to be incorporated as it is into a liquid crystal display device but also a polarizing plate which is prepared as a long film by continuous production and wound up in the form of a roll (for example, a roll having a length of equal to or greater than 2,500 m or 3,900 m). In order to use the polarizing plate in a large-screen liquid crystal display device, it is preferable that the polarizing plate has a width of equal to or greater than 1,470 mm. Regarding the specific constitution of the polarizing plate of the present invention, any constitution can be adopted without particular limitation. For example, the constitution described in FIG. 6 of JP2008-262161A can be adopted.

<<Display Device>>

The polarizer of the present invention is preferably used for a display device.

For example, in the display device, the polarizer can be used for preventing reflection occurring in a liquid crystal display device or an organic electroluminescence display device.

Regarding the use of the polarizer in the liquid crystal display device, the liquid crystal display device of the present invention preferably includes the polarizing plate of the present invention, and more preferably includes at least a liquid crystal cell and the polarizing plate of the present invention. In a case where the liquid crystal display device of the present invention has the polarizing plate and first and second polarizing plates which will be described later, the liquid crystal display device is preferably a liquid crystal display device adopting an in-plane switching (IPS) mode, an optically compensated bend or optically compensated birefringence (OCB) mode, or a vertical alignment (VA) mode in which at least one of the polarizing plates is the polarizing plate of the present invention.

It is preferable that the liquid crystal display device of the present invention has a liquid crystal cell and polarizing plates which are laminated on both sides of the liquid crystal cell and includes a polarizing plate protective film on a surface opposite to the liquid crystal cell side. That is, it is preferable that the liquid crystal display device of the present invention has a first polarizing plate, a liquid crystal cell, and a second polarizing plate and includes the polarizing plate protective film of the present invention on a surface opposite to the polarizing plate surface interposed between each of the polarizing plates and the liquid crystal cell. The liquid crystal display device having the above constitution excellently inhibits the display unevenness and demonstrates high display performance.

Furthermore, in the liquid crystal display device of the present invention, the polarizing plate disposed on the viewing side preferably has a polarizing plate protective film, particularly, a cellulose acylate film having a hardcoat layer on the surface of the polarizing plate protective film on the viewing side. The liquid crystal display device having such a constitution demonstrates high display performance excellently inhibiting display unevenness and excellent scratch resistance and optical durability.

Figure 2:
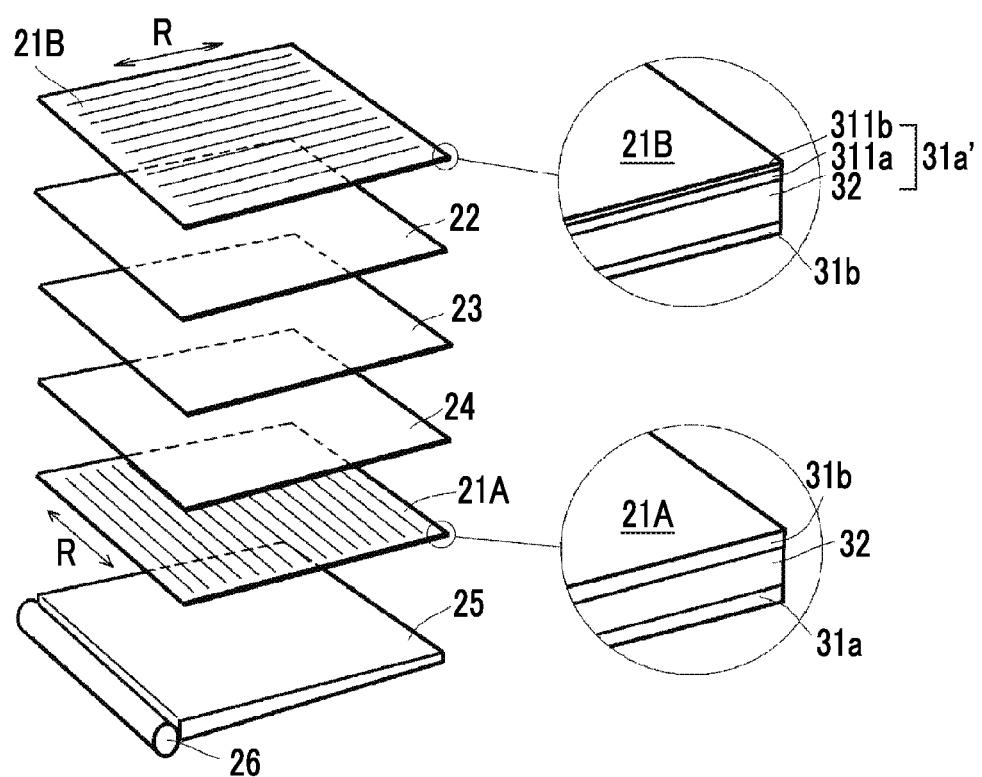
FIG. 2 is a view schematically showing an example of an internal structure of another liquid crystal display device of the present invention.

FIGS. 1 and 2 show the internal constitution of a typical liquid crystal display device as the liquid crystal display device of the present invention. FIG. 1 shows a liquid crystal display device having polarizing plates 21A and 21B in which polarizing plate protective films 31a and 31b of the present invention that is composed of cellulose acylate film are disposed on both surfaces of a polarizer 32. FIG. 2 shows a liquid crystal display device having a polarizing plate protective film 31a' in which a polarizing plate 21B disposed on the viewing side has a hardcoat layer 311b on the viewing side surface of the polarizer 32 via a cellulose acylate film 311a.

FIGS. 1 and 2 show the constitution of an example of the liquid crystal display device of the present invention. However, as the specific constitution of the liquid crystal display device of the present invention, any constitution can be adopted without particular limitation. Furthermore, the constitution described in FIG. 2 of JP2008-262161A can also be preferably adopted.

EXAMPLES

Hereinafter, the present invention will be more specifically described based on examples, but the present invention is not limited thereto.

In the following examples, the following example compounds were used.

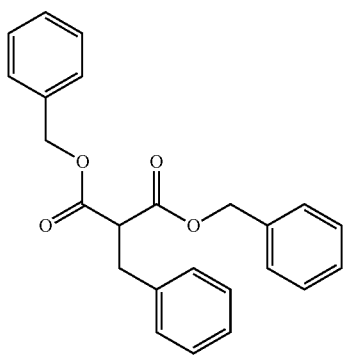

0-1

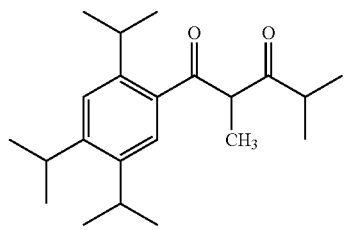

0-10

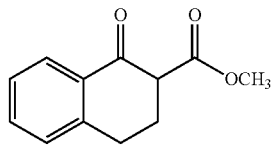

1-1

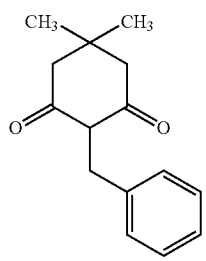

1-7

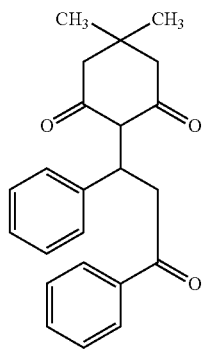

1-8

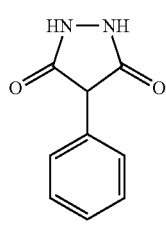

2-1

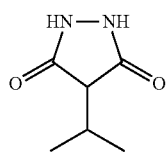

2-3

2-4

2-5
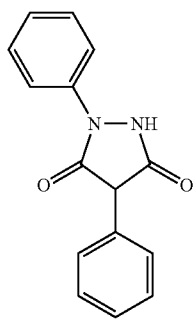
2-6
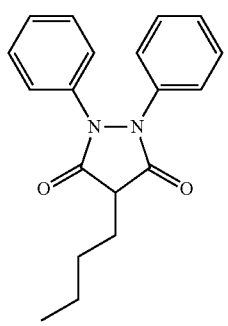
2-7
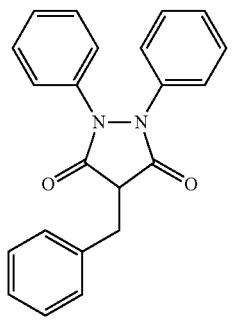
2-8
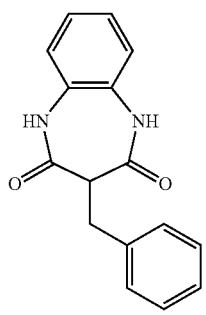
2-10
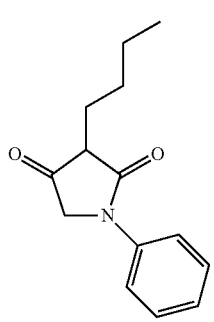
2-11
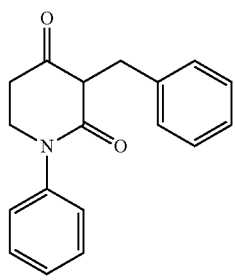
2-13
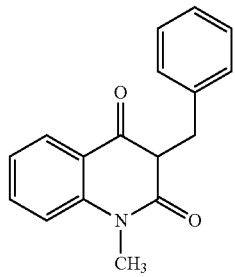
3-1
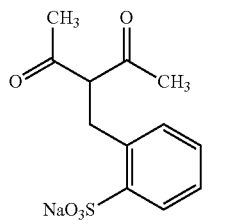
3-2
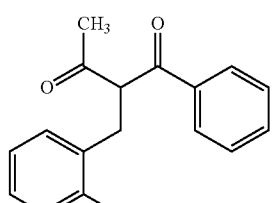
3-3
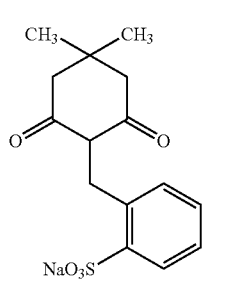
3-4
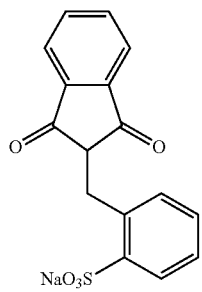

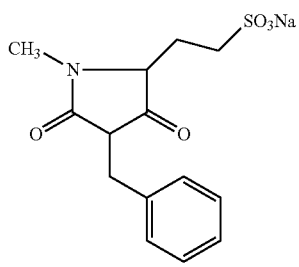
3-5
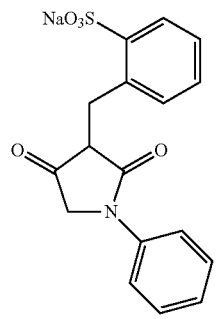
3-6
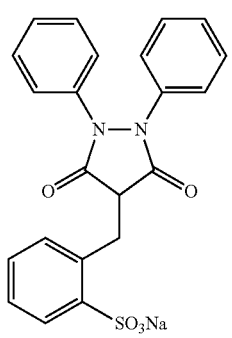
3-7
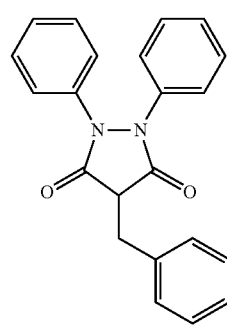
3-8
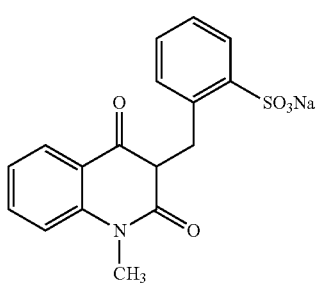
3-9
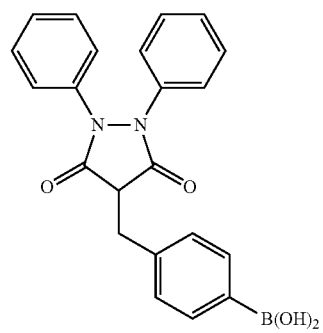
3-10
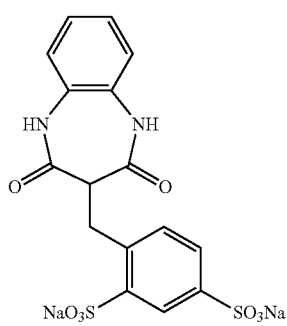
4-4
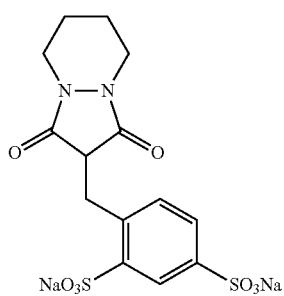
4-5
4-7
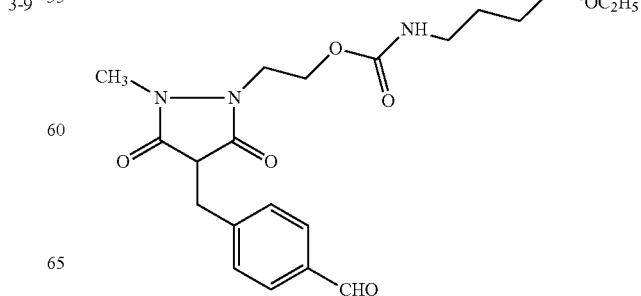

-continued

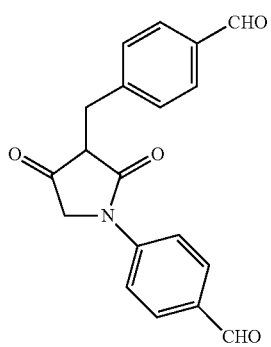

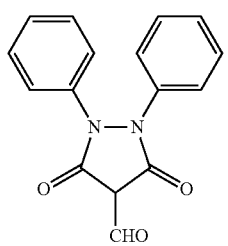

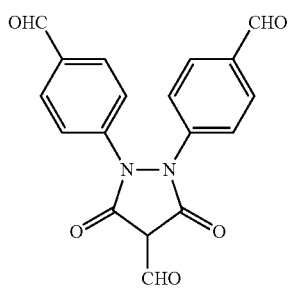

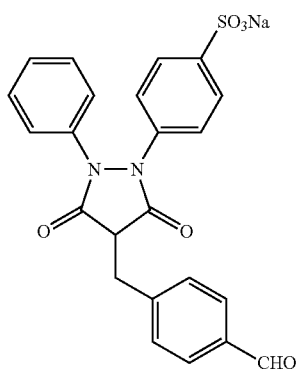

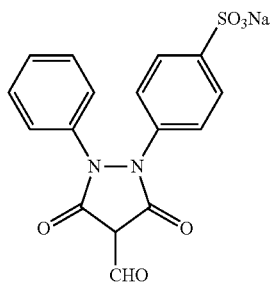

Furthermore, the following compounds were used as comparative compounds.

4-14

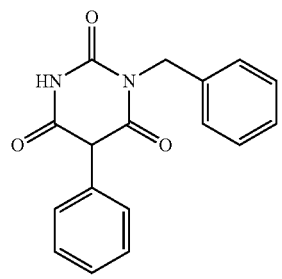

Organic acid 1

4-17

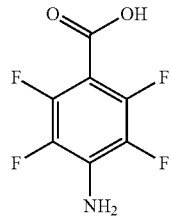

Organic acid 2

4-18

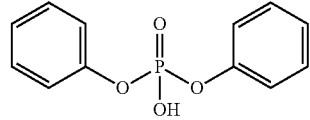

Organic acid 3

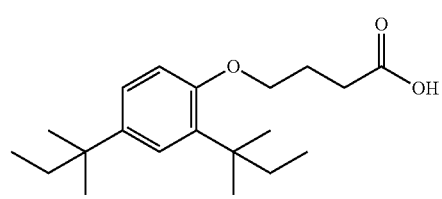

Organic acid 4

5-1

Example 1

Performance Resulting from Adding Compound to Polarizing Plate Protective Film

[Preparation of Polarizing Plate]
1. Preparation of Polarizing Plate No. 101
1) Preparation of Cellulose Acetate Resin As a catalyst, sulfuric acid (7.8 parts by mass with respect to 100 parts by mass of cellulose) was added to cellulose, acetic acid was added thereto, and an acetylation reaction of cellulose was performed at 40° C. After the acetylation, the cellulose acetate was matured at 40° C., and then low-molecular weight components of the cellulose acetate were washed off.

The obtained cellulose acetate (hereinafter, referred to as cellulose acylate as well) had a total degree of acetyl substitution (B) of 2.87 and a degree of polymerization of 370.

2) Preparation of Polarizing Plate Protective Film

The following composition using the cellulose acetate prepared as above was put into a mixing tank and stirred to dissolve each component, thereby preparing a cellulose acetate solution.

Composition of Cellulose Acetate

| | |
|---|---|
| Cellulose acetate having total degree of acetyl substitution (B) of 2.87 and degree of polymerization of 370 | 100.0 parts by mass |

| | |
|---|---|
| Example compound 2-7 | 4.0 parts by mass |
| Methylene chloride (first solvent) | 402.0 parts by mass |
| Methanol (second solvent) | 60.0 parts by mass |

The cellulose acetate solution was cast using a band casting machine and dried at 100° C. until the content of residual solvent became 40%, and then the film was peeled off. The film peeled off was further dried for 20 minutes at an atmospheric temperature of 140° C. The obtained polarizing plate protective film No. 101 had a film thickness of 25 μm.

3) Preparation of Polarizing Plate (a) Saponification Treatment of Polarizing Plate Protective Film The polarizing plate protective film No. 101 prepared as above was dipped in a 2.3 mol/L aqueous sodium hydroxide solution for 3 minutes at 55° C. The film was washed in a water washing bath at room temperature and neutralized using 0.05 mol/L sulfuric acid at 30° C. The film was then washed again in a water washing bath at room temperature and dried over hot air at 100° C.

(b) Preparation of Polarizing Plate

Iodine was adsorbed onto a stretched polyvinyl alcohol film, thereby preparing a polarizer.

By using a polyvinyl alcohol-based adhesive, the polarizing plate protective film No. 101 having undergone the saponification treatment was bonded to one side of the polarizer. A commercially available cellulose triacetate film (trade name "FUJI TAC TD80UF", manufactured by FUJI-FILM Corporation) was also subjected to the same saponification treatment as described above, and by using a polyvinyl alcohol-based adhesive, the commercially available cellulose acetate film having undergone the saponification treatment was bonded to a surface of the polarizer that was the opposite side of the side to which the polarizing plate protective film No. 101 having undergone the saponification treatment was bonded.

At this time, the polarizer and the polarizing plate protective film No. 101 having undergone the saponification treatment were disposed such that the transmission axis of the polarizer and the slow axis of the polarizing plate protective film became parallel to each other. Furthermore, the polarizer and the commercially available cellulose triacetate film having undergone the saponification treatment were disposed such that the transmission axis of the polarizer and the slow axis of the cellulose triacetate film became orthogonal to each other.

In this way, a polarizing plate No. 101 was prepared.

2. Preparation of Polarizing Plate Nos. 102 to 122 and c11 to c15.

Polarizing plate Nos. 102 to 122 and c11 to c15 were prepared in the same manner as used for preparing the polarizing plate No. 101, except that in the preparation of the polarizing plate No. 101, polarizing plate protective film Nos. 102 to 122 and c11 to c15 were prepared by changing the type of additives and the amount thereof added for making the polarizing plate protective film No. 101 as shown in the following Table 1 and by changing the thickness of the polarizing plate protective film as shown in the following Table 1, and those polarizing plate protective films were replaced with the polarizing plate protective film No. 101.

3. Preparation of Polarizing Plate No. 123

1) Preparation of Acrylic Resin Pallet 7,000 g of methyl methacrylate (MMA), 1,000 g of 2-[2'-hydroxy-5'-(methacryloyloxyethyl)phenyl]benzotriazole, 2,000 g of methyl 2-(hydroxymethyl)acrylate (MHMA), and 10,000 g of toluene were put into a 30 L reaction tank equipped with a stirring device, a temperature sensor, a cooling pipe, and a nitrogen introduction pipe, heated to 105° C. under a nitrogen gas flow, and subjected to reflux. Then, as an initiator, 10.0 g of tert-amylperoxyisononanoate (manufactured by ARKEMA Yoshitomi, Ltd., trade name: LUPASOL 570) was added thereto, and while a solution composed of 20.0 g of the initiator and 100 g of toluene was being added dropwise thereto over 4 hours, solution polymerization was performed under reflux (at about 105° C. to 110° C.). The resulting solution was then matured over 4 hours.

Then, 10 g of a mixture of stearyl phosphate/distearyl phosphate (manufactured by SAKAI CHEMICAL INDUSTRY CO., LTD., trade name: PHOSLEX A-18) was added to the obtained polymer solution, and a cyclization condensation reaction was performed for 5 hours under reflux (at about 90° C. to 110° C.). Thereafter, the polymer solution obtained as above by the cyclization condensation reaction was introduced into a vent-type double-screw extruder (Φ=29.75 mm, L/D=30), which had a barrel temperature of 260° C., a rotation frequency of 100 rpm, a degree of pressure reduction of 13.3 hPa to 400 hPa (10 mmHg to 300 mmHg), one rear bent, and four fore-vents, at a treatment rate of 2.0 kg/hour expressed in terms of the resin amount. Subsequently, the polymer solution was subjected to a cyclization condensation reaction and devolatilization in the extruder and extruded, thereby obtaining transparent lactone ring-containing acrylic resin pellets (A) (Mw=200,000).

The lactone ring-containing acrylic resin pellets (A) had a lactone ring formation rate of 97.0%.

By using a double-screw kneader, 4 parts by mass of an example compound 2-7 was mixed with 100 parts by mass of the acrylic resin pellets (A) at 230° C., thereby preparing a resin pellet No. 123.

2) Preparation of Polarizing Plate Protective Film

The obtained resin pellet No. 123 was dried at 800 Pa (6 Torr) and 100° C. for 12 hours and extruded from a T-die at a dice temperature of 290° C. by using a single-screw extruder, thereby preparing a polarizing plate protective film No. 123 having a thickness of 23 μm.

3) Preparation of Polarizing Plate

By using an ultraviolet curable type resin, the polarizing plate protective film No. 123 obtained as above and the polarizer used in the polarizing plate No. 101 were bonded together, thereby obtaining a polarizing plate No. 123.

4. Preparation of Polarizing Plate No. 124

1) Synthesis of Cycloolefin-Based Resin P 50 g of 8-methyl-8-methoxycarbonyltetracyclo[$4.4.0.1^{2,5}.1^{7,10}$]-3-dodecene, 3.6 g of 1-hexene (molecular weight adjuster), and 100 g of toluene were put into a nitrogen-purged reaction container, and the solution was heated to 80° C. Then, 0.09 ml of a toluene solution of triethyl aluminum (0.6 mol/l) as a polymerization catalyst and 0.29 ml of a toluene solution (concentration: 0.025 mol/l) of tungsten hexachloride modified with methanol were added to the solution in the reaction container, and the system was heated and stirred for 3 hours at 80° C. so as to cause a ring opening polymerization reaction, thereby obtaining a ring-opened polymer solution.

Thereafter, as a hydrogenation catalyst, RuHCl(CO)[P($C_6H_5$)$_3$]$_3$ was added thereto in an amount of 500 ppm with respect to the amount of monomer added, and a hydrogenation reaction was performed for 3 hours under conditions of a hydrogen gas pressure of 9.0 MPa to 10.0 MPa and a temperature of 160° C. to 165° C. After the reaction ended, the reaction solution was added to a large amount of isopropyl alcohol solution so as to cause precipitation, and coagulated substances were separated, recovered, and dried, thereby obtaining a norbornene-based hydrogenated ring-opened polymer. Hereinafter, the polymer is referred to as a cycloolefin-based polymer P (COP).

2) Preparation of Polarizing Plate Protective Film

The following composition using the cycloolefin-based polymer P was put into a mixing tank and stirred to dissolve each component, thereby preparing a cycloolefin-based polymer solution.

Composition of Cycloolefin-Based Polymer Solution

| | |
|---|---|
| Cycloolefin-based polymer P | 100.0 parts by mass |
| Ultraviolet absorber (C) | 2.4 parts by mass |
| Example compound 2-7 | 4.0 parts by mass |
| Methylene chloride (solvent) | 325.0 parts by mass |

Ultraviolet absorber (C)

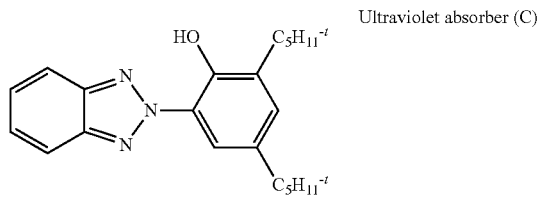

By using a band casting device, the dope (cycloolefin-based polymer solution) prepared as above was cast onto a casting support (support temperature: 22° C.) made of stainless steel. In a state where the amount of residual solvent in the dope was about 20% by mass, the film was peeled off, and both edges of the film in the width direction were gripped by a tenter. In a state where the amount of residual solvent was 5% by mass to 10% by mass, the film was dried while being stretched 1.05-fold (5% expansion) in the width direction at a temperature of 100° C. Then, the film was further dried by being transported between rolls of a thermal treatment device, thereby obtaining a cycloolefin-based film as a polarizing plate protective film No. 124. The obtained cycloolefin-based film had a thickness of 23 μm.

3) Preparation of Polarizing Plate

By using an ultraviolet curable type resin, the polarizing plate protective film No. 124 obtained as above and the polarizer used in the polarizing plate No. 101 were bonded together, thereby preparing a polarizing plate No. 124.

5. Preparation of Polarizing Plate No. 125

1) Manufacturing Polyester Film (1) Manufacturing Polyester A

An esterification reactor was heated, and then at a point in time when the temperature thereof reached 200° C., 86.4 parts by mass of terephthalic acid and 64.6 parts by mass of ethylene glycol were put into the reactor. Thereafter, while the above components were being stirred, 0.017 parts by mass of antimony trioxide as a catalyst, 0.064 parts by mass of magnesium acetate tetrahydrate, and 0.16 parts by mass of triethylamine were added thereto. Then, the above components were heated under pressure so as to perform a pressurization esterification reaction under conditions of a gauge pressure of 0.34 MPa and a temperature of 240° C. Subsequently, the pressure of the esterification reactor was reverted to normal pressure, and 0.014 parts by mass of phosphoric acid was added thereto. Furthermore, the reactor was heated to 260° C. over 15 minutes, and 0.012 parts by mass of trimethyl phosphate was added thereto. After 15 minutes, a dispersion treatment was performed using a high-pressure dispersing machine, and then after 15 minutes, the obtained product of the esterficiation reaction was moved into a polycondensation reactor and subjected to a polycondensation reaction under reduced pressure at 280° C.

After the polycondensation reaction ended, a filtration treatment was performed using a naslon filter having a 95% cutoff diameter of 5 μm, and the resultant was extruded in the form of a strand from a nozzle, cooled and solidified using cooling water having undergone a filtration treatment (pore size: equal to or less than 1 μm), and cut in the form of pellets. The obtained polyethylene terephthalate resin (A) had an intrinsic viscosity of 0.62 dl/g and substantially did not contain inactive particles and internal precipitate particles (hereinafter, the resin will be abbreviated to PET (A)).

(2) Manufacturing Polyester B 10 parts by mass of dried ultraviolet absorber (2,2'-(1,4-phenylene)bis(4H-3,1-benzoxazinone-4-one), 4 parts by mass of the example compound 2-7, and 90 parts by mass of PET (A) (intrinsic viscosity: 0.62 dl/g) not containing particles were mixed together, and from this mixture, a polyethylene terephthalate resin (B) containing an ultraviolet absorber was obtained using a kneading extruder (hereinafter, the resin will be abbreviated to PET (B)).

(3) Preparation of Adhesiveness-Modifying Coating Solution

By performing an ester exchange reaction and a polycondensation reaction according to common methods, a water dispersible sulfonic acid metal salt group-containing copolymerized polyester resin was prepared which was composed of 46 mol % (with respect to the total amount of dicarboxylic acid components) of terephthalic acid, 46 mol % of isophthalic acid, and 8 mol % of sodium 5-sulfonatoisophthalate as dicarboxylic acid components and 50 mol % (with respect to total amount of glycol components) of ethylene glycol and 50 mol % of neopentyl glycol as glycol components. Then, 51.4 parts by mass of water, 38 parts by mass of isopropyl alcohol. 5 parts by mass of n-butyl cellosolve, and 0.06 parts by mass of a nonionic surfactant were mixed together. Thereafter, the mixture was heated and stirred. At a point in time when the temperature thereof reached 77° C., 5 parts by mass of the aforementioned water dispersible sulfonic acid metal salt group-containing copolymerized polyester resin was added thereto, and the mixture was continuously stirred until lumps of the resin disappeared. Subsequently, the aqueous resin dispersion was cooled to normal temperature, thereby obtaining a uniform water dispersible copolymerized polyester resin solution with a concentration of solid contents of 5.0% by mass. Subsequently, 3 parts by mass of silica aggregate particles (manufactured by FUJI SILYSIA CHEMICAL LTD, SYLYSIA 310) were dispersed in 50 parts by mass of water, 0.54 parts by mass of the aqueous dispersion of SYLYSIA 310 was then added to 99.46 parts by mass of the water dispersible copolymerized polyester resin solution, and 20 parts by mass of water was added thereto with stirring, thereby obtaining an adhesiveness-modifying coating solution.

2) Preparation of Polarizing Plate Protective Film

As raw materials for an interlayer of a substrate film, 90 parts by mass of the PET (A) resin pellets not containing particles, an ultraviolet absorber, and 10 parts by mass of the PET (B) resin pellets containing the example compound 2-7 were dried for 6 hours at 135° C. under reduced pressure (1 Torr), and then the resultant was supplied into an extruder 2

(for an interlayer II). Furthermore, PET (A) was dried by a common method and supplied to each extruder 1 (for an outer layer I and an outer layer II) and dissolved at 285° C. Each of the two kinds of polymers was filtered through a filter medium made of sintered stainless steel (nominal filtering accuracy: cutting off 95% of 10 µm particles), subjected to lamination in a two-kind/three-layer converging block, and extruded in the form of a sheet from mouthpieces. Then, the sheet was wound around a casting drum having a surface temperature of 30° C. by using an electrostatic casting method and cooled and solidified, thereby preparing an unstretched film. At this time, the amount of the polymer ejected from each extruder was adjusted such that a thickness ratio of I layer:II layer:III layer became 10:80:10.

Thereafter, by a reverse roll method, both surfaces of the unstretched PET film were coated with the aforementioned adhesiveness-modifying coating solution such that the coating amount after drying became 0.08 g/m$^2$, and then the coating solution was dried for 20 seconds at 80° C.

The unstretched film on which coating layers were formed was directed to a tenter stretching machine. In a state where the edges of the film were being gripped by clips, the film was directed to a hot air zone with a temperature of 125° C. and stretched 4-fold in the width direction. Then, in a state of retaining the width resulting from the stretching performed in the width direction, the film was treated at 225° C. for 30 seconds and then further treated such that the film was relaxed 3% in the width direction, thereby obtaining a uniaxially oriented PET film having a film thickness of about 50 µm.

In this way, a polarizing plate protective film No. 125 was prepared.

3) Preparation of Polarizing Plate

By using an adhesive composed of the adhesiveness-modifying coating solution obtained as above, the polarizing plate protective film No. 125 obtained as above and the polarizer used in the polarizing plate No. 101 were bonded together, thereby preparing a polarizing plate No. 125.

(Performance Evaluation)

The light-fast adhesiveness of each of the polarizing plate protective films prepared as above and the durability of each of the polarizing plates were evaluated as below.

1) Durability Evaluation

The durability of the polarizing plate was tested as below by bonding the polarizing plate to glass by using an adhesive.

The polarizing plate was bonded to glass such that the polarizing plate protective film prepared as above became the air interface side. In this way, two samples (about 5 cm×5 cm) were prepared. The orthogonal transmittance of a single plate was measured in a setup in which a side of the sample film on which the polarizing plate protective film prepared as above was located faced a light source. Each of two samples was measured, and the average was taken as the orthogonal transmittance of the polarizing plate. The orthogonal transmittance of the polarizing plate was measured using an automatic polarizing film analyzer VAP-7070 manufactured by JASCO Corporation within a range of 380 nm to 780 nm, and a value measured at a wavelength of 410 nm resulting in markedly high deterioration compared to other wavelengths was adopted.

Thereafter, samples which were stored for 500 hours and 1,000 hours in an environment with a temperature of 60° C. and a relative humidity of 95% and samples which were stored for 500 hours and 1,000 hours in a dry environment with a temperature of 80° C. were prepared, and the orthogonal transmittance thereof at a wavelength of 410 nm was measured by the same method as used before the elapse of time during which the samples were stored. The change of the orthogonal transmittance before and after the elapse of time was determined, and the result was evaluated as the durability of the polarizer is a polarizing plate characteristic according to the following criteria.

The relative humidity in the environment with no humidity conditioning was within a range of 0% to 20%.

Herein, the amount of change of the orthogonal transmittance was calculated by the following equation.

Amount of change of orthogonal transmittance (%)= [orthogonal transmittance after durability test (%)−orthogonal transmittance before durability test (%)]

—Time Elapse Conditions—

In any case, those ranked A or a higher level in the durability test are desirable for practical use.

a) Polarizing Plate Protective Film Having a Thickness of 23 µm to 25 µm

Storage for 500 hours in an environment with a temperature of 60° C. and a relative humidity of 95%

A+: The amount of change of the orthogonal transmittance before and after the elapse of time was less than 0.4%.

A: The amount of change of the orthogonal transmittance before and after the elapse of time was equal to or greater than 0.4% and less than 0.6%.

B: The amount of change of the orthogonal transmittance before and after the elapse of time was equal to or greater than 0.6% and less than 0.8%.

C: The amount of change of the orthogonal transmittance before and after the elapse of time was equal to or greater than 0.8%.

Storage for 1,000 Hours in an Environment with a Temperature of 60° C. and a Relative Humidity of 95%

A+: The amount of change of the orthogonal transmittance before and after the elapse of time was less than 1.0%.

A: The amount of change of the orthogonal transmittance before and after the elapse of time was equal to or greater than 1.0% and less than 1.4%.

B: The amount of change of the orthogonal transmittance before and after the elapse of time was equal to or greater than 1.4% and less than 1.6%.

C: The amount of change of the orthogonal transmittance before and after the elapse of time was equal to or greater than 1.6%.

Storage for 500 Hours in a Dry Environment with a Temperature of 80° C.

A+: The amount of change of the orthogonal transmittance before and after the elapse of time was less than 0.1%.

A: The amount of change of the orthogonal transmittance before and after the elapse of time was equal to or greater than 0.1% and less than 0.3%.

B: The amount of change of the orthogonal transmittance before and after the elapse of time was equal to or greater than 0.3% and less than 0.5%.

C: The amount of change of the orthogonal transmittance before and after the elapse of time was equal to or greater than 0.5%.

Storage for 1,000 Hours in a Dry Environment with a Temperature of 80° C.

A+: The amount of change of the orthogonal transmittance before and after the elapse of time was less than 0.5%.

A: The amount of change of the orthogonal transmittance before and after the elapse of time was equal to or greater than 0.5% and less than 0.8%.

B: The amount of change of the orthogonal transmittance before and after the elapse of time was equal to or greater than 0.8% and less than 1.0%.

C: The amount of change of the orthogonal transmittance before and after the elapse of time was equal to or greater than 1.0%.

b) Polarizing Plate Protective Film Having a Thickness of 40 μm

Storage for 500 Hours in an Environment with a Temperature of 60° C. and a Relative Humidity of 95%

A+: The amount of change of the orthogonal transmittance before and after the elapse of time was less than 0.2%.

A: The amount of change of the orthogonal transmittance before and after the elapse of time was equal to or greater than 0.2% and less than 0.4%.

B: The amount of change of the orthogonal transmittance before and after the elapse of time was equal to or greater than 0.4% and less than 0.6%.

C: The amount of change of the orthogonal transmittance before and after the elapse of time was equal to or greater than 0.6%.

Storage for 1,000 Hours in an Environment with a Temperature of 60° C. and a Relative Humidity of 95%

A+: The amount of change of the orthogonal transmittance before and after the elapse of time was less than 0.7%.

A: The amount of change of the orthogonal transmittance before and after the elapse of time was equal to or greater than 0.7% and less than 1.0%.

B: The amount of change of the orthogonal transmittance before and after the elapse of time was equal to or greater than 1.0% and less than 1.2%.

C: The amount of change of the orthogonal transmittance before and after the elapse of time was equal to or greater than 1.2%.

Storage for 500 Hours in a Dry Environment with a Temperature of 80° C.

A+: The amount of change of the orthogonal transmittance before and after the elapse of time was less than 0.2%.

A: The amount of change of the orthogonal transmittance before and after the elapse of time was equal to or greater than 0.2% and less than 0.4%.

B: The amount of change of the orthogonal transmittance before and after the elapse of time was equal to or greater than 0.4% and less than 0.5%.

C: The amount of change of the orthogonal transmittance before and after the elapse of time was equal to or greater than 0.5%.

Storage for 1,000 Hours in a Dry Environment with a Temperature of 80° C.

A+: The amount of change of the orthogonal transmittance before and after the elapse of time was less than 0.6%.

A: The amount of change of the orthogonal transmittance before and after the elapse of time was equal to or greater than 0.6% and less than 0.8%.

B: The amount of change of the orthogonal transmittance before and after the elapse of time was equal to or greater than 0.8% and less than 1.0%.

C: The amount of change of the orthogonal transmittance before and after the elapse of time was equal to or greater than 1.0%.

c) Polarizing Plate Protective Film Having a Thickness of 50 μm

Storage for 500 Hours in an Environment with a Temperature of 60° C. and a Relative Humidity of 95%

A+: The amount of change of the orthogonal transmittance before and after the elapse of time was less than 0.2%.

A: The amount of change of the orthogonal transmittance before and after the elapse of time was equal to or greater than 0.2% and less than 0.3%.

B: The amount of change of the orthogonal transmittance before and after the elapse of time was equal to or greater than 0.3% and less than 0.4%.

C: The amount of change of the orthogonal transmittance before and after the elapse of time was equal to or greater than 0.4%.

Storage for 1,000 Hours in an Environment with a Temperature of 60° C. and a Relative Humidity of 95%

A+: The amount of change of the orthogonal transmittance before and after the elapse of time was less than 0.5%.

A: The amount of change of the orthogonal transmittance before and after the elapse of time was equal to or greater than 0.5% and less than 0.6%.

B: The amount of change of the orthogonal transmittance before and after the elapse of time was equal to or greater than 0.6% and less than 0.7%.

C: The amount of change of the orthogonal transmittance before and after the elapse of time was equal to or greater than 0.7%.

Storage for 500 Hours in a Dry Environment with a Temperature of 80° C.

A+: The amount of change of the orthogonal transmittance before and after the elapse of time was less than 0.1%.

A: The amount of change of the orthogonal transmittance before and after the elapse of time was equal to or greater than 0.1% and less than 0.2%.

B: The amount of change of the orthogonal transmittance before and after the elapse of time was equal to or greater than 0.2% and less than 0.3%.

C: The amount of change of the orthogonal transmittance before and after the elapse of time was equal to or greater than 0.3%.

Storage for 1,000 Hours in a Dry Environment with a Temperature of 80° C.

A+: The amount of change of the orthogonal transmittance before and after the elapse of time was less than 0.4%.

A: The amount of change of the orthogonal transmittance before and after the elapse of time was equal to or greater than 0.4% and less than 0.6%.

B: The amount of change of the orthogonal transmittance before and after the elapse of time was equal to or greater than 0.6% and less than 0.8%.

C: The amount of change of the orthogonal transmittance before and after the elapse of time was equal to or greater than 0.8%.

d) Polarizing Plate Protective Film Having a Thickness of 60 μm

Storage for 500 Hours in an Environment with a Temperature of 60° C. and a Relative Humidity of 95%

A+: The amount of change of the orthogonal transmittance before and after the elapse of time was less than 0.2%.

A: The amount of change of the orthogonal transmittance before and after the elapse of time was equal to or greater than 0.2% and less than 0.3%.

B: The amount of change of the orthogonal transmittance before and after the elapse of time was equal to or greater than 0.3% and less than 0.4%.

C: The amount of change of the orthogonal transmittance before and after the elapse of time was equal to or greater than 0.4%.

Storage for 1,000 Hours in an Environment with a Temperature of 60° C. and a Relative Humidity of 95%

A+: The amount of change of the orthogonal transmittance before and after the elapse of time was less than 0.4%.

A: The amount of change of the orthogonal transmittance before and after the elapse of time was equal to or greater than 0.4% and less than 0.6%.

B: The amount of change of the orthogonal transmittance before and after the elapse of time was equal to or greater than 0.6% and less than 0.8%.

C: The amount of change of the orthogonal transmittance before and after the elapse of time was equal to or greater than 0.8%.

Storage for 500 Hours in a Dry Environment with a Temperature of 80° C.

A+: The amount of change of the orthogonal transmittance before and after the elapse of time was less than 0.1%.

A: The amount of change of the orthogonal transmittance before and after the elapse of time was equal to or greater than 0.1% and less than 0.2%.

B: The amount of change of the orthogonal transmittance before and after the elapse of time was equal to or greater than 0.2% and less than 0.3%.

C: The amount of change of the orthogonal transmittance before and after the elapse of time was equal to or greater than 0.3%.

Storage for 1,000 Hours in a Dry Environment with a Temperature of 80° C.

A+: The amount of change of the orthogonal transmittance before and after the elapse of time was less than 0.3%.

A: The amount of change of the orthogonal transmittance before and after the elapse of time was equal to or greater than 0.3% and less than 0.5%.

B: The amount of change of the orthogonal transmittance before and after the elapse of time was equal to or greater than 0.5% and less than 0.6%.

C: The amount of change of the orthogonal transmittance before and after the elapse of time was equal to or greater than 0.6%.

e) Polarizing Plate Protective Film Having a Thickness of 80 μm

Storage for 500 Hours in an Environment with a Temperature of 60° C. and a Relative Humidity of 95%

A+: The amount of change of the orthogonal transmittance before and after the elapse of time was less than 0.1%.

A: The amount of change of the orthogonal transmittance before and after the elapse of time was equal to or greater than 0.1% and less than 0.2%.

B: The amount of change of the orthogonal transmittance before and after the elapse of time was equal to or greater than 0.2% and less than 0.25%.

C: The amount of change of the orthogonal transmittance before and after the elapse of time was equal to or greater than 0.25%.

Storage for 1,000 Hours in an Environment with a Temperature of 60° C. and a Relative Humidity of 95%

A+: The amount of change of the orthogonal transmittance before and after the elapse of time was less than 0.3%.

A: The amount of change of the orthogonal transmittance before and after the elapse of time was equal to or greater than 0.3% and less than 0.4%.

B: The amount of change of the orthogonal transmittance before and after the elapse of time was equal to or greater than 0.4% and less than 0.5%.

C: The amount of change of the orthogonal transmittance before and after the elapse of time was equal to or greater than 0.5%.

Storage for 500 Hours in a Dry Environment with a Temperature of 80° C.

A+: The amount of change of the orthogonal transmittance before and after the elapse of time was less than 0.07%.

A: The amount of change of the orthogonal transmittance before and after the elapse of time was equal to or greater than 0.07% and less than 0.1%.

B: The amount of change of the orthogonal transmittance before and after the elapse of time was equal to or greater than 0.1% and less than 0.2%.

C: The amount of change of the orthogonal transmittance before and after the elapse of time was equal to or greater than 0.2%.

Storage for 1,000 Hours in a Dry Environment with a Temperature of 80° C.

A+: The amount of change of the orthogonal transmittance before and after the elapse of time was less than 0.1%.

A: The amount of change of the orthogonal transmittance before and after the elapse of time was equal to or greater than 0.1% and less than 0.3%.

B: The amount of change of the orthogonal transmittance before and after the elapse of time was equal to or greater than 0.3% and less than 0.4%.

C: The amount of change of the orthogonal transmittance before and after the elapse of time was equal to or greater than 0.4%.

(Preparation of Optical Film with Hardcoat Layer)

The components described in the following table were mixed together and then filtered through a polypropylene filter having a pore size of 30 μm, thereby preparing a coating solution for a hardcoat layer.

Composition of Coating Solution for Hardcoat Layer

| | |
|---|---|
| Monomer: pentaerythritol triacrylate/pentaerythritol tetraacrylate (mixing ratio by mass: 3/2) | 53.5 parts by mass |
| Photopolymerization initiator (for ultraviolet rays): IRGACURE ™ 907 (manufactured by Ciba Specialty Chemicals, Inc) | 1.5 parts by mass |
| Ethyl acetate | 45 parts by mass |

The air-exposed surface of each of the polarizing plate protective films manufactured as above was coated with the aforementioned coating solution for a hardcoat layer by a micro-gravure coating method under the condition of a transport rate of 30 m/min, and the coating solution was dried for 150 seconds at 60° C. Then, in a state where nitrogen purging was being performed (oxygen concentration: equal to or less than 0.5%), the coating solution was irradiated with ultraviolet rays at an illuminance of 400 mW/cm$^2$ and an irradiation amount of 150 mJ/cm$^2$ by using a 160 W/cm air-cooled metal halide lamp (manufactured by EYE GRAPHICS Co., Ltd.) such that the coating layer was cured, thereby forming a hardcoat layer (thickness: 6 μm).

In this way, by forming a hardcoat layer on the air-exposed surface of each of the polarizing plate protective films, polarizing plate protective films with a hardcoat layer were prepared.

2) Evaluation of Light-Fast Adhesiveness

The light-fast adhesiveness was evaluated as below.

First, each of the polarizing plate protective films with a hardcoat layer prepared as above was irradiated with light for 96 hours in an environment with a temperature of 60° C. and a relative humidity of 50% by using a SUPER XENON WEATHER METER SX75 manufactured by Suga Test Instruments Co., Ltd.

Then each of the polarizing plate protective films with a hardcoat layer was subjected to humidity conditioning for 2 hours under the conditions of a temperature of 25° C. and a relative humidity of 60%. Within the surface on the side where the hardcoat layer was located, in a 1 cm×1 cm region of the polarizing plate protective film with a hardcoat layer, 11 cuts were made at an interval of 1 mm in each of the vertical and horizontal directions by using a cutter knife such that a checker pattern was formed. In this way, a total of 100 square cells with a size of 1 mm×1 mm were formed, and a polyester pressure sensitive tape (No. 31B) manufactured by NITTO DENKO CORPORATION was bonded onto the surface thereof. After 30 minutes, the tape was quickly peeled off in a vertical direction, the number of cells peeled off was counted, and the light-fast adhesiveness was evaluated according to the following 4 criteria. The adhesiveness was evaluated three times in the same manner, and the average was adopted. The results are shown in the following Table 1.

Evaluation Criteria

A+: The number of cells peeled off among 100 cells was equal to or less than 5.

A: The number of cells peeled off among 100 cells was 6 to 10.

B: The number of cells peeled off among 100 cells was 11 to 20.

C: The number of cells peeled off among 100 cells was 21 to 30.

The obtained results are summarized in the following Table 1.

Herein, the additive in Table 1 indicates the example compound synthesized as above.

TABLE 1

| Polarizing plate protective film No. | Polarizing plate protective film | | | | Characteristics of Polarizing plate Durability of polarizer: change of orthogonal transmittance (%) | |
|---|---|---|---|---|---|---|
| | Resin | Thickness (μm) | Additive Type | Added amount[a] | 60° C., 95%, 500 hours | 80° C., Dry, 500 hours |
| 101 | Cellulose acylate | 25 | 2-7 | 1.0 | A+ | A+ |
| 102 | Cellulose acylate | 25 | 2-7 | 2.0 | A+ | A+ |
| 103 | Cellulose acylate | 25 | 2-7 | 4.0 | A+ | A+ |
| 104 | Cellulose acylate | 25 | 2-6 | 4.0 | A+ | A+ |
| 105 | Cellulose acylate | 25 | 2-8 | 4.0 | A+ | A+ |
| 106 | Cellulose acylate | 25 | 2-10 | 4.0 | A+ | A+ |
| 107 | Cellulose acylate | 25 | 2-11 | 4.0 | A+ | A+ |
| 108 | Cellulose acylate | 25 | 2-12 | 4.0 | A+ | A+ |
| 109 | Cellulose acylate | 25 | 0-1 | 4.0 | A | A |
| 110 | Cellulose acylate | 25 | 0-10 | 4.0 | A | A |
| 111 | Cellulose acylate | 25 | 1-1 | 4.0 | A+ | A+ |
| 112 | Cellulose acylate | 25 | 1-7 | 4.0 | A+ | A+ |
| 113 | Cellulose acylate | 25 | 1-8 | 4.0 | A+ | A+ |
| 114 | Cellulose acylate | 40 | 2-7 | 4.0 | A+ | A+ |
| 115 | Cellulose acylate | 60 | 2-7 | 4.0 | A+ | A+ |
| 116 | Cellulose acylate | 80 | 2-7 | 4.0 | A+ | A+ |
| 117 | Cellulose acylate | 25 | 4-4 | 4.0 | A+ | A+ |
| 118 | Cellulose acylate | 25 | 4-5 | 4.0 | A+ | A+ |
| 119 | Cellulose acylate | 25 | 4-7 | 4.0 | A+ | A+ |
| 120 | Cellulose acylate | 25 | 4-14 | 4.0 | A+ | A+ |
| 121 | Cellulose acylate | 25 | 4-17 | 4.0 | A+ | A+ |
| 122 | Cellulose acylate | 25 | 4-18 | 4.0 | A+ | A+ |
| 123 | Acryl | 23 | 2-7 | 4.0 | A+ | A+ |
| 124 | COP | 23 | 2-7 | 4.0 | A+ | A+ |
| 125 | PET | 100 | 2-7 | 4.0 | A+ | A+ |
| c11 | Cellulose acylate | 25 | Organic acid 1 | 4.0 | A+ | A+ |
| c12 | Cellulose acylate | 25 | Organic acid 2 | 4.0 | B | B |
| c13 | Cellulose acylate | 25 | Organic acid 3 | 4.0 | B | B |
| c14 | Cellulose acylate | 25 | Organic acid 4 | 4.0 | A | A |
| c15 | Cellulose acylate | 25 | blank | — | C | C |

| Polarizing plate protective film No. | Characteristics of polarizing plate Durability of polarizer: change of orthogonal transmittance (%) | | Characteristics of polarizing plate protective film | Note |
|---|---|---|---|---|
| | 60° C., 95%, 1,000 hours | 80° C., Dry, 1,000 hours | Light-fast adhesiveness | |
| 101 | A | A | A | Present invention |
| 102 | A | A | A | Present invention |
| 103 | A+ | A+ | A+ | Present invention |
| 104 | A+ | A+ | A+ | Present invention |
| 105 | A+ | A+ | A+ | Present invention |
| 106 | A+ | A+ | A+ | Present invention |
| 107 | A+ | A+ | A+ | Present invention |
| 108 | A+ | A+ | A+ | Present invention |
| 109 | A+ | A+ | A | Present invention |

TABLE 1-continued

| | | | | |
|---|---|---|---|---|
| 110 | A+ | A+ | A+ | Present invention |
| 111 | A | A | A | Present invention |
| 112 | A | A | A | Present invention |
| 113 | A | A | A | Present invention |
| 114 | A+ | A+ | A+ | Present invention |
| 115 | A+ | A+ | A+ | Present invention |
| 116 | A+ | A+ | A+ | Present invention |
| 117 | A+ | A+ | A | Present invention |
| 118 | A+ | A+ | A | Present invention |
| 119 | A+ | A+ | A | Present invention |
| 120 | A+ | A+ | A | Present invention |
| 121 | A+ | A+ | A | Present invention |
| 122 | A+ | A+ | A | Present invention |
| 123 | A+ | A+ | A+ | Present invention |
| 124 | A+ | A+ | A+ | Present invention |
| 125 | A+ | A+ | A+ | Present invention |
| c11 | A | A | B | Comparative example |
| c12 | B | B | A | Comparative example |
| c13 | B | B | A | Comparative example |
| c14 | A | A | B | Comparative example |
| c15 | C | C | A+ | Comparative example |

*a)*Showing the added amount with respect to 100 parts by mass of the film resin
COP: cycloolefin-based resin P
PET: mixed resin of polyester A and polyester B If the compound represented by Formula (I) of the present invention is used in a polarizing plate protective film, the durability of a polarizing plate (durability of polarizer), particularly, the change of performance with the passage of time is greatly improved, and the light-fast adhesiveness is also improved. It is understood that such an effect is not obtained from the compound of the related art.

Example 2

Performance Resulting from Adding Compound to Polarizer (Preparation of Polarizer)
1. Preparation of Polarizer No. 201
200 kg of water with a temperature of 18° C. was put into a 500 L tank. In a state where the water was being stirred, 42 kg of a polyvinyl alcohol-based resin having a weight average molecular weight of 165,000 and a degree of saponification of 99.8 mol % was added thereto, followed by stirring for 15 minutes. The obtained slurry was dehydrated, thereby obtaining a polyvinyl alcohol-based resin wet cake having a moisture content of 40% by mass. 70 kg of the obtained polyvinyl alcohol-based resin wet cake (resin content: 42 kg) was put into a dissolution tank, 4.2 kg of glycerin as a plasticizer, 0.42 kg (1.0 part by mass with respect to 100 parts by mass of the polyvinyl alcohol-based resin) of an example compound A as an additive, and 10 kg of water were added thereto, and water vapor was injected into the tank from the bottom of the tank. At a point in time when the temperature of the resin in the tank reached 50° C., stirring was performed (rotation frequency: 5 rpm), and at a point in time when the temperature of the resin in the tank reached 100° C., the internal pressure of the system was reduced. The system was heated to 150° C., and then the injection of water vapor was stopped (total amount of the injected water vapor: 75 kg). The resultant was stirred for 30 minutes (rotation frequency: 20 rpm) such that it was uniformly dissolved, and then the concentration was adjusted, thereby obtaining an aqueous polyvinyl alcohol-based resin solution in which the concentration of the polyvinyl alcohol-based resin with respect to water was 23%.

Thereafter, the aqueous polyvinyl alcohol-based resin solution (solution temperature: 147° C.) was supplied into a double-screw extruder through a first gear pump, deaerated, and then discharged from a second gear pump. The discharged aqueous polyvinyl alcohol-based resin solution was cast onto a casting drum through a T-shaped slit die (straight manifold die), thereby forming a film. The film was formed by casting under the following conditions.
Diameter of casting drum: 3.200 mm
Width of casting drum: 4.3 m
Rotation speed of casting drum: 8 m/min
Surface temperature of casting drum: 90° C.
Resin temperature at the outlet of T-shaped slit die: 95° C.
The front surface and rear surface of the obtained film were dried by being alternately passed through a plurality of drying rolls under the following conditions.
Diameter of drying roll: 320 mm
Width of drying roll: 4.3 m
Number of drying rolls (n): 10
Rotation speed of drying roll: 8 m/min
Surface temperature of drying roll: 50° C.
The polyvinyl alcohol film (length: 4,000 m, width: 4 m, thickness: 50 µm) prepared as above was dipped in hot water with a temperature of 40° C. for 2 minutes, subjected to a swelling treatment, and then stretched 1.30-fold. The obtained film was dipped in an aqueous solution containing 17.2 g/L boric acid (manufactured by Società Chimica Larderello S. p. A), 0.15 g/L iodine (manufactured by Junsei Chemical Co., Ltd.), and 0.6 g/L potassium iodide (manufactured by Junsei Chemical Co., Ltd.) for 2 minutes at 30° C. so as to perform a dying treatment using iodine and iodide. While being uniaxially stretched 5.0-fold, the obtained film having undergone the dying treatment was treated for 5 minutes in an aqueous solution with a temperature of 50° C. containing 30.0 g/L boric acid. The obtained film was subjected to a drying treatment for 9 minutes at 70° C.
In this way, a polarizer No. 201 was prepared.
2. Preparation of Polarizer Nos. 202 to 215 and c21 to c25
Polarizer Nos. 202 to 215 and c21 to c25 were prepared in the same manner as used for preparing the polarizer No. 201, except that in the preparation of the polarizer No. 201, the combination of the type of additive and the amount thereof added was changed as shown in the following Table 2.

(Preparation of Polarizing Plate)

1. Preparation of Polarizing Plate No. 201

Cellulose triacetate films (FUJITAC TG40 and ZRT40) manufactured by FUJIFILM Corporation were dipped in a 2.3 mol/L aqueous sodium hydroxide solution for 3 minutes at 55° C. The films were then washed in a water washing bath at room temperature and neutralized using 0.05 mol/L sulfuric acid at 30° C. Thereafter, the films were washed again in a water washing bath at room temperature and dried over hot air with a temperature of 100° C., and a saponification treatment was performed on the surface of the polarizing plate protective films.

Each of the two kinds of polarizing plate protective film having undergone the saponification treatment was bonded to one side of the polarizer No. 201 manufactured as above by using a polyvinyl alcohol-based adhesive. At this time, the polarizer and the polarizing plate protective film were disposed such that the transmission axis of the polarizer and the slow axis of the polarizing plate protective film (cellulose triacetate film) became orthogonal to each other.

In this way, a polarizing plate No. 201 was prepared.

2. Preparation of Polarizing Plate Nos. 202 to 215 and c21 to c25

Polarizing plate Nos. 202 to 215 and c21 to c25 were prepared in the same manner as used for preparing the polarizing plate No. 201, except that in the preparation of the polarizing plate No. 201, the polarizer No. 201 was replaced with the polarizer Nos. 202 to 215 and c21 to c25, and the combination of the polarizer and the polarizing plate protective film used was changed as shown in the following Table 2.

(Performance Evaluation)

The bleed-out properties and durability of each of the polarizing plates prepared as above were evaluated as below. Furthermore, the solubilities of additives in water were compared to each other.

1) Solubility of Additive in Water

The amount of the additive dissolving in 100 ml of pure water at 25° C. was measured and evaluated according to the following criteria.

Evaluation Criteria

A+: The amount of the additive dissolving in 100 ml of pure water was equal to or greater than 5 g.

A: The amount of the additive dissolving in 100 ml of pure water was equal to or greater than 3 g and less than 5 g.

B: The amount of the additive dissolving in 100 ml of pure water was equal to or greater than 1 g and less than 3 g.

C: The amount of the additive dissolving in 100 ml of pure water was less than 1 g.

2) Bleed-Out Properties in Polarizer

The bleed-out properties were evaluated as below.

[Haze Evaluation]

The haze in each of the polarizing plates obtained as above was measured and evaluated according to the following criteria A+ to C.

The haze in each of polarizing plates was measured according to JIS K-7136 by using a haze meter "HGM-2DP" (trade name, manufactured by Suga Test Instruments Co., Ltd.).

Evaluation Criteria

A+: The haze was less than 0.3%.

A: The haze was equal to or greater than 0.3% and less than 0.5%.

B: The haze was equal to or greater than 0.5% and less than 0.7%.

C: The haze was equal to or greater than 0.7%.

3) Evaluation of Characteristics (Durability) of Polarizing Plate

The durability of the polarizing plate was tested by measuring an orthogonal transmittance and a degree of polarization as below by bonding the polarizing plate to glass through an adhesive.

The polarizing plate was bonded to glass such that the polarizing plate protective film shown in the following Table 2 became the air interface side. In this way, two samples (about 5 cm×5 cm) were prepared. The orthogonal transmittance of a single plate was measured in a setup in which a side of the sample film on which the polarizing plate protective film prepared as above was located faced a light source. Each of the two samples was measured, and the average was taken as the orthogonal transmittance of the polarizing plate.

Meanwhile, the degree of polarization as calculated by the following equation by using a parallel transmittance measured in addition to the orthogonal transmittance obtained as above.

Degree of polarization (%)=[(orthogonal transmittance−parallel transmittance)/(orthogonal transmittance+parallel transmittance)]$^{1/2}$×100

The orthogonal transmittance and the degree of polarization of the polarizing plate were measured using an automatic polarizing film analyzer VAP-7070 manufactured by JASCO Corporation within a range of 380 nm to 780 nm, and a value measured at a wavelength of 410 nm resulting in markedly high deterioration compared to other wavelengths was adopted.

Thereafter, samples which were stored for 500 hours and 1,000 hours in an environment with a temperature of 60° C. and a relative humidity of 95% and samples which were stored for 500 hours and 1,000 hours in a dry environment with a temperature of 80° C. were prepared, and the orthogonal transmittance at a wavelength of 410 nm was measured in the same manner as in the measurement performed before the elapse of time during which the samples were stored. The amount of change of the orthogonal transmittance and the amount of change of the degree of polarization before and after the elapse of time was determined, and the result was evaluated as the durability of the polarizer that was a polarizing plate characteristic according to the following criteria.

The relative humidity in the environment with no humidity conditioning was within a range of 0% to 20%.

Herein, the amount of change of the degree of polarization was calculated by the following equation.

Amount of change of degree of polarization (%)= [degree of polarization after durability test (%)− degree of polarization before durability test (%)]

—Time Elapse Conditions—

In any case, those ranked A or a higher level in the durability test are desirable for practical use.

Storage for 500 hours in an environment with a temperature of 60° C. and a relative humidity of 95%

Amount of Change of Orthogonal Transmittance (%)

A+: The amount of change of the orthogonal transmittance before and after the elapse of time was less than 0.1%.

A: The amount of change of the orthogonal transmittance before and after the elapse of time was equal to or greater than 0.1% and less than 0.4%.

B: The amount of change of the orthogonal transmittance before and after the elapse of time was equal to or greater than 0.4% and less than 0.8%.

C: The amount of change of the orthogonal transmittance before and after the elapse of time was equal to or greater than 0.8%.

Amount of Change of Degree of Polarization (%)

A+: The amount of change of the degree of polarization before and after the elapse of time was less than 0.05%.

A: The amount of change of the orthogonal transmittance before and after the elapse of time was equal to or greater than 0.05% and less than 2.0%.

B: The amount of change of the orthogonal transmittance before and after the elapse of time was equal to or greater than 2.0% and less than 3.0%.

C: The amount of change of the orthogonal transmittance before and after the elapse of time was equal to or greater than 3.0%.

Storage for 1,000 Hours in an Environment with a Temperature of 60° C. and a Relative Humidity of 95%

The amount of change of orthogonal transmittance (%)

A+: The amount of change of the orthogonal transmittance before and after the elapse of time was less than 0.5%.

A: The amount of change of the orthogonal transmittance before and after the elapse of time was equal to or greater than 0.5% and less than 1.0%.

B: The amount of change of the orthogonal transmittance before and after the elapse of time was equal to or greater than 1.0% and less than 1.6%.

C: The amount of change of the orthogonal transmittance before and after the elapse of time was equal to or greater than 1.6%.

Amount of Change of Degree of Polarization (%)

A+: The amount of change of the degree of polarization before and after the elapse of time was less than 1.0%.

A: The amount of change of the degree of polarization before and after the elapse of time was equal to or greater than 1.0% and less than 4.0%.

B: The amount of change of the degree of polarization before and after the elapse of time was equal to or greater than 4.0% and less than 6.0%.

C: The amount of change of the degree of polarization before and after the elapse of time was equal to or greater than 6.0%.

Storage for 500 Hours in a Dry Environment with a Temperature of 80° C.

The Amount of Change of Orthogonal Transmittance (%)

A+: The amount of change of the orthogonal transmittance before and after the elapse of time was less than 0.05%.

A: The amount of change of the orthogonal transmittance before and after the elapse of time was equal to or greater than 0.05% and less than 0.1%.

B: The amount of change of the orthogonal transmittance before and after the elapse of time was equal to or greater than 0.1% and less than 0.2%.

C: The amount of change of the orthogonal transmittance before and after the elapse of time was equal to or greater than 0.2%.

Amount of Change of Degree of Polarization (%)

A+: The amount of change of the degree of polarization before and after the elapse of time was less than 0.05%.

A: The amount of change of the degree of polarization before and after the elapse of time was equal to or greater than 0.05% and less than 1.0%.

B: The amount of change of the degree of polarization before and after the elapse of time was equal to or greater than 1.0% and less than 2.0%.

C: The amount of change of the degree of polarization before and after the elapse of time was equal to or greater than 2.0%.

Storage for 1,000 Hours in a Dry Environment with a Temperature of 80° C.

A+: The amount of change of the orthogonal transmittance before and after the elapse of time was less than 0.1%.

A: The amount of change of the orthogonal transmittance before and after the elapse of time was equal to or greater than 0.1% and less than 0.3%.

B: The amount of change of the orthogonal transmittance before and after the elapse of time was equal to or greater than 0.3% and less than 0.4%.

C: The amount of change of the orthogonal transmittance before and after the elapse of time was equal to or greater than 0.4%.

Amount of Change of Degree of Polarization (%)

A+: The amount of change of the degree of polarization before and after the elapse of time was less than 0.1%.

A: The amount of change of the degree of polarization before and after the elapse of time was equal to or greater than 0.1% and less than 2.0%.

B: The amount of change of the degree of polarization before and after the elapse of time was equal to or greater than 2.0% and less than 4.0%.

C: The amount of change of the degree of polarization before and after the elapse of time was equal to or greater than 4.0%.

The obtained results are summarized in the following Table 2.

Herein, the additive in Table 2 indicates the example compound synthesized as above.

TABLE 2

| | Polarizer | | | | Polarizing plate protective film | | | | Characteristics of polarizing plate Durability of polarizer: change of orthogonal transmittance (%) | |
|---|---|---|---|---|---|---|---|---|---|---|
| | | Additive | | | Glass side Film | | Air side Film | | | |
| Polarizer No. | Type | Added amount[b] | Solubility in water | Bleed out | Type | thickness (μm) | Type | thickness (μm) | 60° C., 95%, 500 hours | 80° C., Dry, 500 hours |
| 201 | 3-6 | 0.1 | A+ | A+ | F-A | 40 | F-B | 40 | A+ | A+ |
| 202 | 3-6 | 1.0 | A+ | A+ | F-A | 40 | F-B | 40 | A+ | A+ |
| 203 | 3-6 | 10.0 | A+ | A+ | F-A | 40 | F-B | 40 | A+ | A+ |

TABLE 2-continued

| | | | | | | | | | | |
|---|---|---|---|---|---|---|---|---|---|---|
| 204 | 3-5 | 1.0 | A+ | A+ | F-A | 40 | F-B | 40 | A+ | A+ |
| 205 | 2-3 | 1.0 | A | A | F-A | 40 | F-B | 40 | A+ | A+ |
| 206 | 3-7 | 1.0 | A+ | A+ | F-A | 40 | F-B | 40 | A+ | A+ |
| 207 | 2-1 | 1.0 | A | A | F-A | 40 | F-B | 40 | A+ | A+ |
| 208 | 3-2 | 1.0 | A+ | A+ | F-A | 40 | F-B | 40 | A | A |
| 209 | 3-3 | 1.0 | A+ | A+ | F-A | 40 | F-B | 40 | A+ | A+ |
| 210 | 3-4 | 1.0 | A+ | A+ | F-A | 40 | F-B | 40 | A+ | A+ |
| 211 | 3-8 | 1.0 | A+ | A+ | F-A | 40 | F-B | 40 | A+ | A+ |
| 212 | 3-9 | 1.0 | A+ | A+ | F-A | 40 | F-B | 40 | A+ | A+ |
| 213 | 3-10 | 1.0 | A+ | A+ | F-A | 40 | F-B | 40 | A+ | A+ |
| 214 | 5-1 | 1.0 | A+ | A+ | F-A | 40 | F-B | 40 | A+ | A+ |
| 215 | 5-5 | 1.0 | A+ | A+ | F-A | 40 | F-B | 40 | A+ | A+ |
| c21 | $ZnCl_2$ | 1.0 | A+ | A+ | F-A | 40 | F-A | 40 | B | A |
| c22 | $ZnSO_4 \cdot 7H_2O$ | 1.0 | A+ | A+ | F-A | 40 | F-A | 40 | B | A |
| c23 | Organic acid 1 | 1.0 | C | C | F-A | 40 | F-A | 40 | A+ | A+ |
| c24 | Organic acid 2 | 1.0 | A | A | F-A | 40 | F-A | 40 | A | A |
| c25 | blank | — | — | — | F-A | 40 | F-A | 40 | C | C |

| | Characteristics of polarizing plate | | | | | | |
|---|---|---|---|---|---|---|---|
| | Durability of polarizer: change of orthogonal transmittance (%) | | Durability of polarizer: change of degree of polarization (%) | | Durability of polarizer: change of degree of polarization (%) | | |
| Polarizer No. | 60° C., 95%, 1,000 hours | 80° C., Dry, 1,000 hours | 60° C., 95%, 500 hours | 80° C., Dry, 500 hours | 60° C., 95%, 1,000 hours | 80° C., Dry, 1,000 hours | Note |
| 201 | A+ | A+ | A+ | A+ | A+ | A+ | Present invention |
| 202 | A+ | A+ | A+ | A+ | A+ | A+ | Present invention |
| 203 | A+ | A+ | A+ | A+ | A+ | A+ | Present invention |
| 204 | A+ | A+ | A+ | A+ | A+ | A+ | Present invention |
| 205 | A+ | A+ | A+ | A+ | A+ | A+ | Present invention |
| 206 | A+ | A+ | A+ | A+ | A+ | A+ | Present invention |
| 207 | A+ | A+ | A+ | A+ | A+ | A+ | Present invention |
| 208 | A+ | A+ | A | A | A+ | A+ | Present invention |
| 209 | A | A | A+ | A+ | A | A | Present invention |
| 210 | A | A | A+ | A+ | A | A | Present invention |
| 211 | A | A | A+ | A+ | A | A | Present invention |
| 212 | A | A | A+ | A+ | A | A | Present invention |
| 213 | A+ | A+ | A+ | A+ | A+ | A+ | Present invention |
| 214 | A+ | A+ | A+ | A+ | A+ | A+ | Present invention |
| 215 | A+ | A+ | A+ | A+ | A+ | A+ | Present invention |
| c21 | B | A | B | A | B | A | Comparative example |
| c22 | B | A | B | A | B | A | Comparative example |
| c23 | B | B | A+ | A+ | B | B | Comparative example |
| c24 | B | B | A | A | B | B | Comparative example |
| c25 | C | C | C | C | C | C | Comparative example |

[b]Showing the added amount with respect to 100 parts by mass of polyvinyl alcohol resin
F-A: FUJITAC ZRT40
F-B: FUJITAC TG40

If the compound represented by Formula (I) of the present invention is used in a polarizer, the durability of a polarizing plate (durability of the polarizer), particularly, the change of performance with the elapse of time is reduced, the amount of change of the orthogonal transmittance and the amount of change of the degree of polarization are small, and the durability of the polarizing plate is greatly improved.

The amount of change of the degree of polarization is more easily affected by the amount of change with the elapse of time. However, in the polarizing plate in which the compound represented by Formula (I) of the present invention is used in a polarizer, the amount of change could be more effectively reduced than in a polarizing plate in which the compound of the comparative example was used in a polarizer. From the above results, it is understood that the compound represented by Formula (I) of the present invention effectively acts by being contained in the polarizer layer.

It is also understood that such an effect is not obtained from the compound of the related art.

Example 3

Performance Resulting from Adding Compound to Adhesive Layer (Preparation of Adhesive Layer)
1. Preparation of Water-Soluble Adhesive of Adhesive Layer No. 301

A water-soluble adhesive containing a polyvinyl alcohol-based resin which contains an example compound B and a metal compound colloid was prepared according to the following method.

100 parts by mass of an acetoacetyl group-containing polyvinyl alcohol-based resin (manufactured by Nippon Synthetic Chemical Industry Co., Ltd., trade name "GOHSEFIMER Z200", average degree of polymerization: 1,200, degree of saponification: 98.5 mol %, degree of acetoacetylation: 5 mol %) and 50 parts by mass of methylol melamine were dissolved in pure water under a temperature condition of 30° C., there by obtaining an aqueous solution in which the concentration of solid contents was adjusted to be 3.7%. 18 parts by mass of an aqueous alumina colloid solution (average particle size: 15 nm, concentration of solid contents: 10%, positively charged) and 0.1 parts by mass of an example compound A as an additive were added to 100 parts by mass of the aqueous solution, thereby preparing a water-soluble adhesive.

2. Preparation of Water-Soluble Adhesives of Adhesive Layer Nos. 302 to 315 and c31 to c35

Water-soluble adhesives of adhesive layer Nos. 302 to 315 and c31 to c35 were prepared in the same manner as used for preparing the adhesive layer No. 301, except that in the preparation of the water-soluble adhesive of the adhesive layer No. 301, the type of the additive and the amount thereof added were changed as shown in the following Table 3.

(Preparation of Polarizing Plate)
1. Preparation of Polarizing Plate No. 301

Cellulose triacetate films (FUJITAC TG40 and ZRT40) manufactured by FUJIFILM Corporation were dipped in a 2.3 mol/L aqueous sodium hydroxide solution for 3 minutes at 55° C. The films were then washed in a water washing bath at room temperature and neutralized using 0.05 mol/L sulfuric acid at 30° C. Thereafter, the films were washed again in a water washing bath at room temperature and dried over hot air with a temperature of 100° C. In this way, a saponification treatment was performed on the surface of the polarizing plate protective films.

Iodine was adsorbed onto a stretched polyvinyl alcohol film, thereby preparing a polarizer.

Each of the two kinds of polarizing plate protective film having undergone the saponification treatment was coated with the polyvinyl alcohol-based adhesive of the adhesive layer No. 301 prepared as above such that the thickness of the adhesive layer became 5 µm, and each of the films were bonded to one side of the polarizer. At this time, the polarizer and the polarizing plate protective film (cellulose triacetate film) were disposed such that the transmission axis of the polarizer and the slow axis of the polarizing plate protective film became orthogonal to each other. The polarizing plate obtained in this way was dried for 5 minutes in an oven with a temperature of 60° C. to 90° C. After drying, the polarizing plate was subjected to a heating treatment (annealing treatment) by being passed through an oven with a temperature of 80° C. over 10 minutes, thereby preparing a polarizing plate No. 301.

2. Preparation of Polarizing Plate Nos. 302 to 315 and c31 to c35

Polarizing plate Nos. 302 to 315 and c31 to c35 were prepared in the same manner as used for preparing the polarizing plate No. 301, except that in the preparation of the polarizing plate No. 301, the water-soluble adhesive of the adhesive layer No. 301 was replaced with the water-soluble adhesive Nos. 302 to 315 and c31 to c35, and the film thickness was changed as shown in the following Table 3.

(Performance Evaluation)
The bleed-out properties and durability of each of the polarizing plates prepared as above were evaluated as below.
1) Bleed-Out Properties in Adhesive Layer
The bleed-out properties were evaluated as below.
[Haze Evaluation]
The haze in each of the polarizing plates obtained as above was measured and evaluated according to the following criteria A+ to C.

The haze in each of polarizing plates was measured according to JIS K-7136 by using a haze meter "HGM-2DP" (trade name, manufactured by Suga Test Instruments Co., Ltd.).

Evaluation Criteria
A+: The haze was less than 0.3%.
A: The haze was equal to or greater than 0.3% and less than 0.5%.
B: The haze was equal to or greater than 0.5% and less than 0.7%.
C: The haze was equal to or greater than 0.7%.

2) Evaluation of Durability
The durability of the polarizing plate was tested by bonding the polarizing plate to glass through an adhesive.

The polarizing plate was bonded to glass such that the polarizing plate protective film prepared as above became the air interface side. In this way, two samples (about 5 cm×5 cm) were prepared. The orthogonal transmittance of a single plate was measured in a setup in which a side of the sample film on which the polarizing plate protective film prepared as above was located faced a light source. The orthogonal transmittance and the degree of polarization of the polarizing plate were determined through measurement performed in the same manner as in Example 2.

Then, samples which were stored for 500 hours and 1,000 hours in an environment with a temperature of 60° C. and a relative humidity of 95% and samples which were stored for 500 hours and 1,000 hours in a dry environment with a temperature of 80° C. were prepared, and the orthogonal transmittance at a wavelength of 410 nm and the degree of polarization were measured by the same method as used before the elapse of time during which the samples were stored. The amount of change of the orthogonal transmittance and the amount of change of the degree of polarization before and after the elapse of time were determined, and the result was evaluated as the polarizer durability which is a polarizing plate characteristic according to the following criteria.

Herein, the relative humidity in the environment with no humidity conditioning was within a range of 0% to 20%.

—Time Elapse Conditions—

In any case, those ranked A or a higher level in the durability test are desirable for practical use.

Storage for 500 hours in an environment with a temperature of 60° C. and a relative humidity of 95%

Amount of Change of Orthogonal Transmittance (%)

A+: The amount of change of the orthogonal transmittance before and after the elapse of time was less than 0.1%.

A: The amount of change of the orthogonal transmittance before and after the elapse of time was equal to or greater than 0.1% and less than 0.4%.

B: The amount of change of the orthogonal transmittance before and after the elapse of time was equal to or greater than 0.4% and less than 0.8%.

C: The amount of change of the orthogonal transmittance before and after the elapse of time was equal to or greater than 0.8%.

Amount of Change of Degree of Polarization (%)

A+: The amount of change of the degree of polarization before and after the elapse of time was less than 0.05%.

A: The amount of change of the degree of polarization before and after the elapse of time was equal to or greater than 0.05% and less than 2.0%.

B: The amount of change of the degree of polarization before and after the elapse of time was equal to or greater than 2.0% and less than 3.0%.

C: The amount of change of the degree of polarization before and after the elapse of time was equal to or greater than 3.0%.

Storage for 1,000 Hours in an Environment with a Temperature of 60° C. and a Relative Humidity of 95%

Amount of Change of Orthogonal Transmittance (%)

A+: The amount of change of the orthogonal transmittance before and after the elapse of time was less than 0.5%.

A: The amount of change of the orthogonal transmittance before and after the elapse of time was equal to or greater than 0.5% and less than 1.0%.

B: The amount of change of the orthogonal transmittance before and after the elapse of time was equal to or greater than 1.0% and less than 1.6%.

C: The amount of change of the orthogonal transmittance before and after the elapse of time was equal to or greater than 1.6%.

Amount of Change of Degree of Polarization (%)

A+: The amount of change of the degree of polarization before and after the elapse of time was less than 1.0%.

A: The amount of change of the degree of polarization before and after the elapse of time was equal to or greater than 1.0% and less than 4.0%.

B: The amount of change of the degree of polarization before and after the elapse of time was equal to or greater than 4.0% and less than 6.0%.

C: The amount of change of the degree of polarization before and after the elapse of time was equal to or greater than 6.0%.

Storage for 500 Hours in a Dry Environment with a Temperature of 80° C.

Amount of Change of Orthogonal Transmittance (%)

A+: The amount of change of the orthogonal transmittance before and after the elapse of time was less than 0.05%.

A: The amount of change of the orthogonal transmittance before and after the elapse of time was equal to or greater than 0.05% and less than 0.1%.

B: The amount of change of the orthogonal transmittance before and after the elapse of time was equal to or greater than 0.1% and less than 0.2%.

C: The amount of change of the orthogonal transmittance before and after the elapse of time was equal to or greater than 0.2%.

Amount of Change of Degree of Polarization (%)

A+: The amount of change of the degree of polarization before and after the elapse of time was less than 0.05%.

A: The amount of change of the degree of polarization before and after the elapse of time was equal to or greater than 0.05% and less than 1.0%.

B: The amount of change of the degree of polarization before and after the elapse of time was equal to or greater than 1.0% and less than 2.0%.

C: The amount of change of the degree of polarization before and after the elapse of time was equal to or greater than 2.0%.

Storage for 1,000 Hours in a Dry Environment with a Temperature of 80° C.

Amount of Change of Orthogonal Transmittance (%)

A+: The amount of change of the orthogonal transmittance before and after the elapse of time was less than 0.1%.

A: The amount of change of the orthogonal transmittance before and after the elapse of time was equal to or greater than 0.1% and less than 0.3%.

B: The amount of change of the orthogonal transmittance before and after the elapse of time was equal to or greater than 0.3% and less than 0.4%.

C: The amount of change of the orthogonal transmittance before and after the elapse of time was equal to or greater than 0.4%.

Amount of Change of Degree of Polarization (%)

A+: The amount of change of the degree of polarization before and after the elapse of time was less than 0.1%.

A: The amount of change of the degree of polarization before and after the elapse of time was equal to or greater than 0.1% and less than 2.0%.

B: The amount of change of the degree of polarization before and after the elapse of time was equal to or greater than 2.0% and less than 4.0%.

C: The amount of change of the degree of polarization before and after the elapse of time was equal to or greater than 4.0%.

The obtained results are summarized in the following Table 3.

Herein, the additive in Table 3 indicates the example compound synthesized as above.

TABLE 3

| | | | | | | Characteristics of polarizing plate | |
| --- | --- | --- | --- | --- | --- | --- | --- |
| | Adhesive layer | | | | | Durability of polarizer: change of orthogonal transmittance (%) | |
| Adhesive layer No. | Additive | Additive Added amount[c] | Coating amount | Film thickness (μm) | Bleed out | 60° C., 95%, 500 hours | 80° C., Dry, 500 hours |
| 301 | 3-6 | 1.0 | 0.089 | 5 | A+ | A+ | A+ |
| 302 | 3-6 | 10.0 | 0.089 | 5 | A+ | A+ | A+ |
| 303 | 3-6 | 20.0 | 0.089 | 10 | A+ | A+ | A+ |

TABLE 3-continued

| | | | | | | | |
|---|---|---|---|---|---|---|---|
| 304 | 3-5 | 10.0 | 0.089 | 5 | A+ | A+ | A+ |
| 305 | 2-3 | 10.0 | 0.089 | 5 | A | A+ | A+ |
| 306 | 3-7 | 10.0 | 0.089 | 5 | A+ | A+ | A+ |
| 307 | 2-5 | 10.0 | 0.089 | 5 | A | A+ | A+ |
| 308 | 3-1 | 10.0 | 0.089 | 5 | A+ | A | A |
| 309 | 3-2 | 10.0 | 0.089 | 5 | A+ | A+ | A+ |
| 310 | 3-7 | 10.0 | 0.089 | 5 | A+ | A+ | A+ |
| 311 | 3-8 | 10.0 | 0.089 | 5 | A+ | A+ | A+ |
| 312 | 3-9 | 10.0 | 0.089 | 5 | A+ | A+ | A+ |
| 313 | 3-10 | 10.0 | 0.089 | 5 | A+ | A+ | A+ |
| 314 | 5-1 | 10.0 | 0.089 | 5 | A+ | A+ | A+ |
| 315 | 5-5 | 10.0 | 0.089 | 5 | A+ | A+ | A+ |
| c31 | $ZnCl_2$ | 10.0 | 0.089 | 5 | A+ | B | A |
| c32 | $ZnSO_4 \cdot 7H_2O$ | 10.0 | 0.089 | 5 | A+ | B | A |
| c33 | Organic acid 1 | 10.0 | 0.089 | 5 | C | A+ | A+ |
| c34 | Organic acid 2 | 10.0 | 0.089 | 5 | A | A | A |
| c35 | blank | — | — | 5 | — | C | C |

| | Characteristics of polarizing plate | | | | | | |
|---|---|---|---|---|---|---|---|
| | Durability of polarizer: change of orthogonal transmittance (%) | | Durability of polarizer: change of degree of polarization (%) | | Durability of polarizer: change of degree of polarization (%) | | |
| Adhesive layer No. | 60° C., 95%, 1,000 hours | 80° C., Dry, 1,000 hours | 60° C., 95%, 500 hours | 80° C., Dry, 500 hours | 60° C., 95%, 1,000 hours | 80° C., Dry, 1,000 hours | Note |
| 301 | A+ | A+ | A+ | A+ | A+ | A+ | Present invention |
| 302 | A+ | A+ | A+ | A+ | A+ | A+ | Present invention |
| 303 | A+ | A+ | A+ | A+ | A+ | A+ | Present invention |
| 304 | A+ | A+ | A+ | A+ | A+ | A+ | Present invention |
| 305 | A+ | A+ | A+ | A+ | A+ | A+ | Present invention |
| 306 | A+ | A+ | A+ | A+ | A+ | A+ | Present invention |
| 307 | A+ | A+ | A+ | A+ | A+ | A+ | Present invention |
| 308 | A+ | A+ | A | A | A+ | A+ | Present invention |
| 309 | A | A | A+ | A+ | A | A | Present invention |
| 310 | A | A | A+ | A+ | A | A | Present invention |
| 311 | A | A | A+ | A+ | A | A | Present invention |
| 312 | A | A | A+ | A+ | A | A | Present invention |
| 313 | A+ | A+ | A+ | A+ | A+ | A+ | Present invention |
| 314 | A+ | A+ | A+ | A+ | A+ | A+ | Present invention |
| 315 | A+ | A+ | A+ | A+ | A+ | A+ | Present invention |
| c31 | B | A | B | A | B | A | Comparative example |
| c32 | B | A | B | A | B | A | Comparative example |
| c33 | A | A | A+ | A+ | A | A | Comparative example |
| c34 | B | B | A | A | B | B | Comparative example |
| c35 | C | C | C | C | C | C | Comparative example |

*)Showing the added amount with respect to 100 parts by mass of the adhesive resin If the compound represented by Formula (I) of the present invention is used in an adhesive layer, the durability of a polarizing plate (durability of the polarizer), particularly, the change of performance with the elapse of time is reduced, the amount of change of the orthogonal transmittance and the amount of change of the degree of polarization are small, and the durability of the polarizing plate is greatly improved.

The amount of change of the degree of polarization is more easily affected by the amount of change with the elapse of time. However, in the polarizing plate in which the compound represented by Formula (I) of the present invention is used in a polarizer, the amount of change could be more effectively reduced than in a polarizing plate in which the compound of the comparative example was used in a polarizer. From the above results, it is understood that the compound represented by Formula (I) of the present invention effectively acts by being contained in the polarizer layer.

It is also understood that such an effect is not obtained from the compound of the related art.

As is evident from the results of Examples 1 to 3, if the polarizing plate composition of the present invention is used, a liquid crystal display device having excellent performance as described above can be prepared.

Hitherto, the present invention and preferred embodiments thereof have been described. However, unless otherwise specified, the present invention is not limited to any of the details of the description. The present inventors consider that the present invention should be interpreted in a broader sense within a range that does not depart from the gist and scope of the present invention shown in the accompanying claims.

EXPLANATION OF REFERENCES 21A, 21B polarizing plate
22 color filter substrate
23 liquid crystal layer (liquid crystal cell)
24 array substrate
25 light guide plate
26 light source
31a, 31a', 31b polarizing plate protective film
311a polarizing plate protective film
311b hardcoat layer
32 polarizer
R polarization direction

What is claimed is:

1. A polarizing plate composition comprising a compound represented by the following Formula (II),

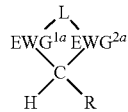

Formula (II)

in Formula (II), R represents a substituent which is not a group containing a phenolic hydroxyl group or an aromatic amino group; each of $EWG^{1a}$ and $EWG^{2a}$ independently represents a divalent electron-withdrawing group; and L represents a single bond or a divalent linking group.

2. The polarizing plate composition according to claim 1, wherein each of $EWG^{1a}$ and $EWG^{2a}$ is a substituent having a Hammett's σp value of equal to or greater than 0.20.

3. The polarizing plate composition according to claim 1, wherein each of $EWG^{1a}$ and $EWG^{2a}$ is —C(=O)—, —SO$_2$—, —SO—, or *—P(=O)(ORb)O— in which * represents a position of bonding to a carbon atom to which R is bonded; and Rb represents a substituent.

4. The polarizing plate composition according to claim 1, wherein an atom of L bonded to $EWG^{1a}$ and $EWG^{2a}$ is —C($R^{x1}$)($R^{x2}$)—, —N(Ra)—, —O—, or —S—, each of $R^{x1}$ and $R^{x2}$ is independently a hydrogen atom or a substituent, and Ra is a hydrogen atom or a substituent.

5. The polarizing plate composition according to claim 1, wherein the compound represented by Formula (II) is represented by the following Formula (III),

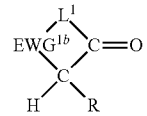

Formula (III)

in Formula (III), R has the same definition as R in Formula (II); $EWG^{1b}$ represents —C(=O)—, —SO$_2$—, —SO—, or *—P(=O)(ORb)O—; * represents a position of bonding to a carbon atom substituted with R; Rb represents a substituent; and $L^1$ represents a divalent linking group.

6. The polarizing plate composition according to claim 1, wherein R is an alkyl group, an alkenyl group, a cycloalkyl group, a cycloalkenyl group, an aryl group, or a heterocyclic group.

7. The polarizing plate composition according to claim 1, wherein the compound represented by Formula (II) is represented by the following Formula (IV),

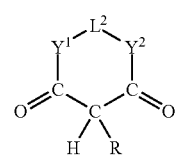

Formula (IV)

in Formula (IV), R has the same definition as R in Formula (II); each of $Y^1$ and $Y^2$ independently represents —C($R^{x1}$)($R^{x2}$)—, —N(Ra)—, —O—, or —S—; each of $R^{x1}$ and $R^{x2}$ independently represents a hydrogen atom or a substituent; Ra represents a hydrogen atom or a substituent; $L^2$ represents a single bond or a divalent linking group bonding $Y^1$ and $Y^2$ to each other through 1 to 3 atoms; and $Y^1$ and $Y^2$, $Y^1$ and $L^2$, or $Y^2$ and $L^2$ may form a ring by being bonded to each other.

8. The polarizing plate composition according to claim 1, further comprising cellulose acylate, polyvinyl alcohol, or acylated or ketalized polyvinyl alcohol.

9. The polarizing plate composition according to claim 8, wherein provided that the total degree of acyl substitution of the cellulose acylate is denoted by A, A of the cellulose acylate satisfies the following expression $1.5 \leq A \leq 3.0$.

10. The polarizing plate composition according to claim 8, wherein provided that an acyl group of the cellulose acylate is an acetyl group, and the total degree of acetyl substitution of the cellulose acylate is denoted by B, B of the cellulose acylate satisfies the following expression $2.0 \leq B \leq 3.0$.

11. The polarizing plate composition according to claim 1, further comprising:
polyvinyl alcohol or acylated or ketalized polyvinyl alcohol; and
a metal compound colloid.

12. The polarizing plate composition according to claim 1, further comprising:
polyvinyl alcohol or acylated or ketalized polyvinyl alcohol; and
a dichroic colorant.

13. A polarizing plate protective film composed of the polarizing plate composition according to claim 1.

14. A polarizer composed of the polarizing plate composition according to claim 1.

15. A polarizing plate comprising an adhesive layer or a pressure sensitive adhesive layer composed of the polarizing plate composition according to claim 1.

16. A polarizing plate comprising the polarizing plate protective film according to claim 13.

17. A polarizing plate comprising the polarizer according to claim 14.

18. A liquid crystal display device comprising the polarizing plate according to claim 15.

* * * * *